United States Patent [19]

Newhouse et al.

[11] Patent Number: 5,091,092
[45] Date of Patent: Feb. 25, 1992

[54] SINGLE-LOOP CHROMATOGRAPHY SYSTEM AND METHOD

[75] Inventors: Daniel L. Newhouse, Harrisburg; Leemer Cernohlavek, Fulton; Philip D. Lochhaas, Ashland, all of Mo.

[73] Assignee: Analytical Bio-Chemistry Laboratories, Inc., Columbia, Mo.

[21] Appl. No.: 347,519

[22] Filed: May 3, 1989

[51] Int. Cl.⁵ .................... B01D 35/08; G01N 25/06
[52] U.S. Cl. ..................... 210/635; 210/198.2; 210/656; 73/864.22
[58] Field of Search .......... 210/198.2, 635, 656; 73/61.1 C, 864.21, 864.22, 864.23, 864.24, 864.25; 436/47

[56] References Cited

U.S. PATENT DOCUMENTS

| | | | |
|---|---|---|---|
| 2,846,121 | 8/1958 | Ronnebeck | 73/23.42 |
| 3,677,091 | 7/1972 | Guigan | 73/864.22 |
| 3,744,219 | 7/1973 | Tindle et al. | 55/162 |
| 3,912,456 | 10/1975 | Young | 73/864.22 |
| 3,925,207 | 12/1975 | Scriba | 210/198.2 |
| 4,042,499 | 8/1977 | Ramstad et al. | 210/198.2 |
| 4,108,602 | 8/1978 | Hanson et al. | 73/864.22 |
| 4,217,223 | 8/1980 | Baba et al. | 218/198.2 |
| 4,478,095 | 10/1984 | Bradley et al. | 73/864.21 |
| 4,604,363 | 8/1986 | Newhouse et al. | 159/47.1 |
| 4,674,323 | 6/1987 | Rulf et al. | 364/497 |

*Primary Examiner*—Stanley S. Silverman
*Assistant Examiner*—Cynthia L. Nessler
*Attorney, Agent, or Firm*—Epstein, Edell & Retzer

[57] ABSTRACT

Automated gel permeation chromatography of multiple individual samples is effected with high precision and high speed utilizing a common sample sizing loop into which each sample is placed prior to its injection into the chromatography column, thereby eliminating the need for precisely matched sample loops. Each sample is pre-stored in its own container, the containers being automatically sequentially accessed to feed a portion of the contained sample medium to the common sample sizing loop. The common sample flow path, including the sample sizing loop is automatically cleaned with rinse solvent between loading of successive samples into the sizing loop. Multiple programs may be employed to control the processing times for different types of sample fluid. A sample container closure member having a unique sealing insert member is provided to preclude leakage of fluid from the sample storage container when the container is pressurized.

21 Claims, 47 Drawing Sheets

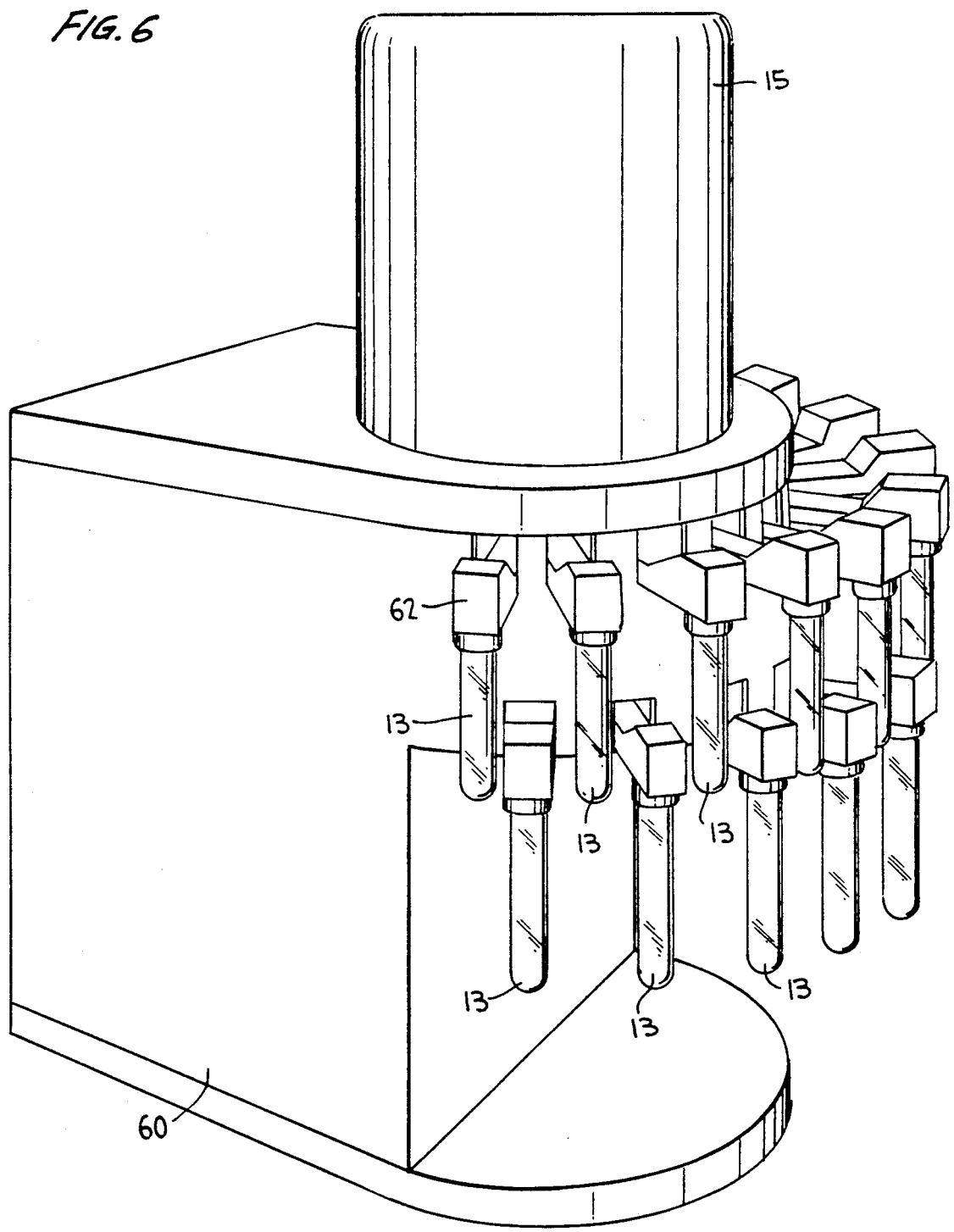

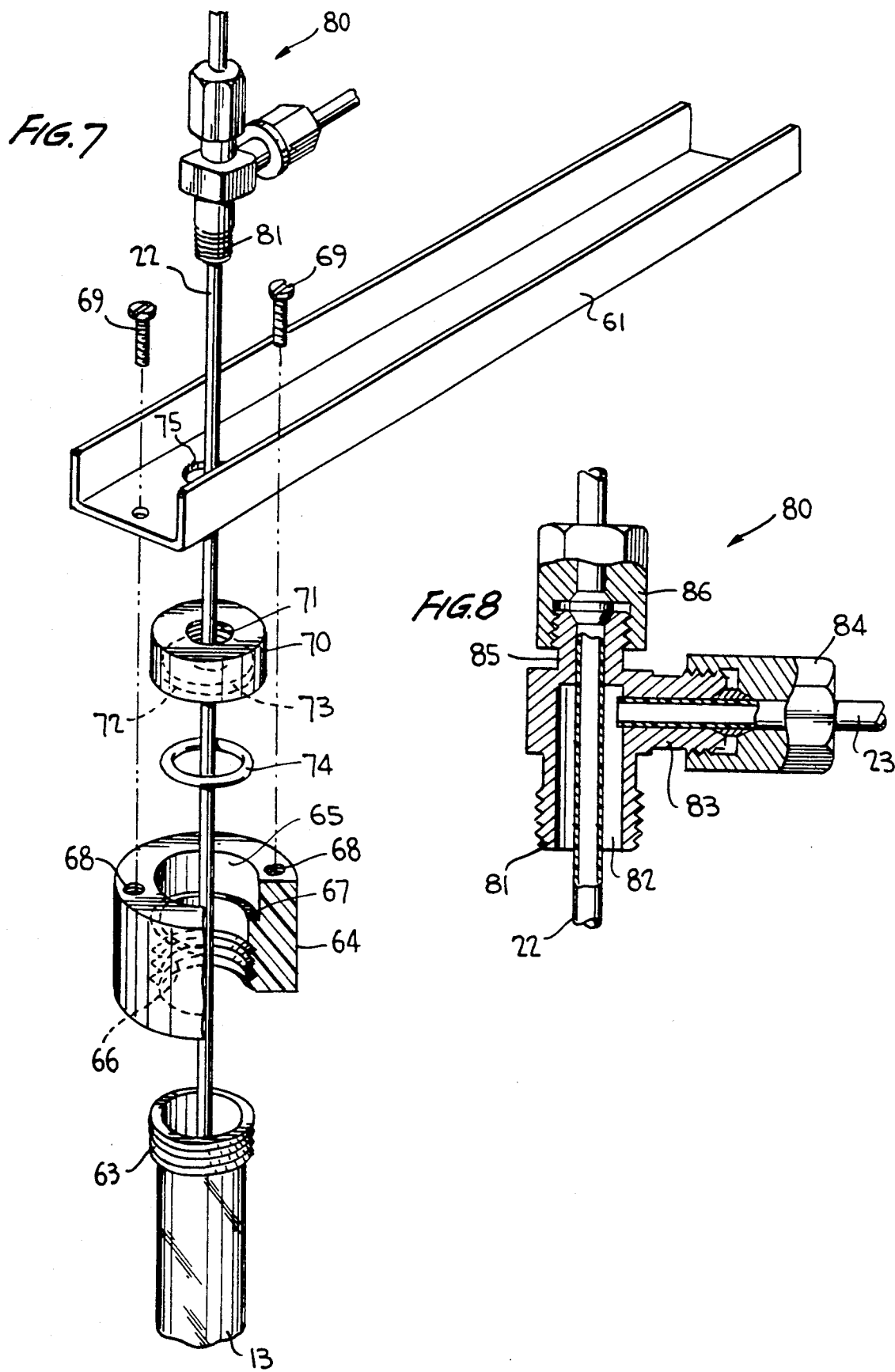

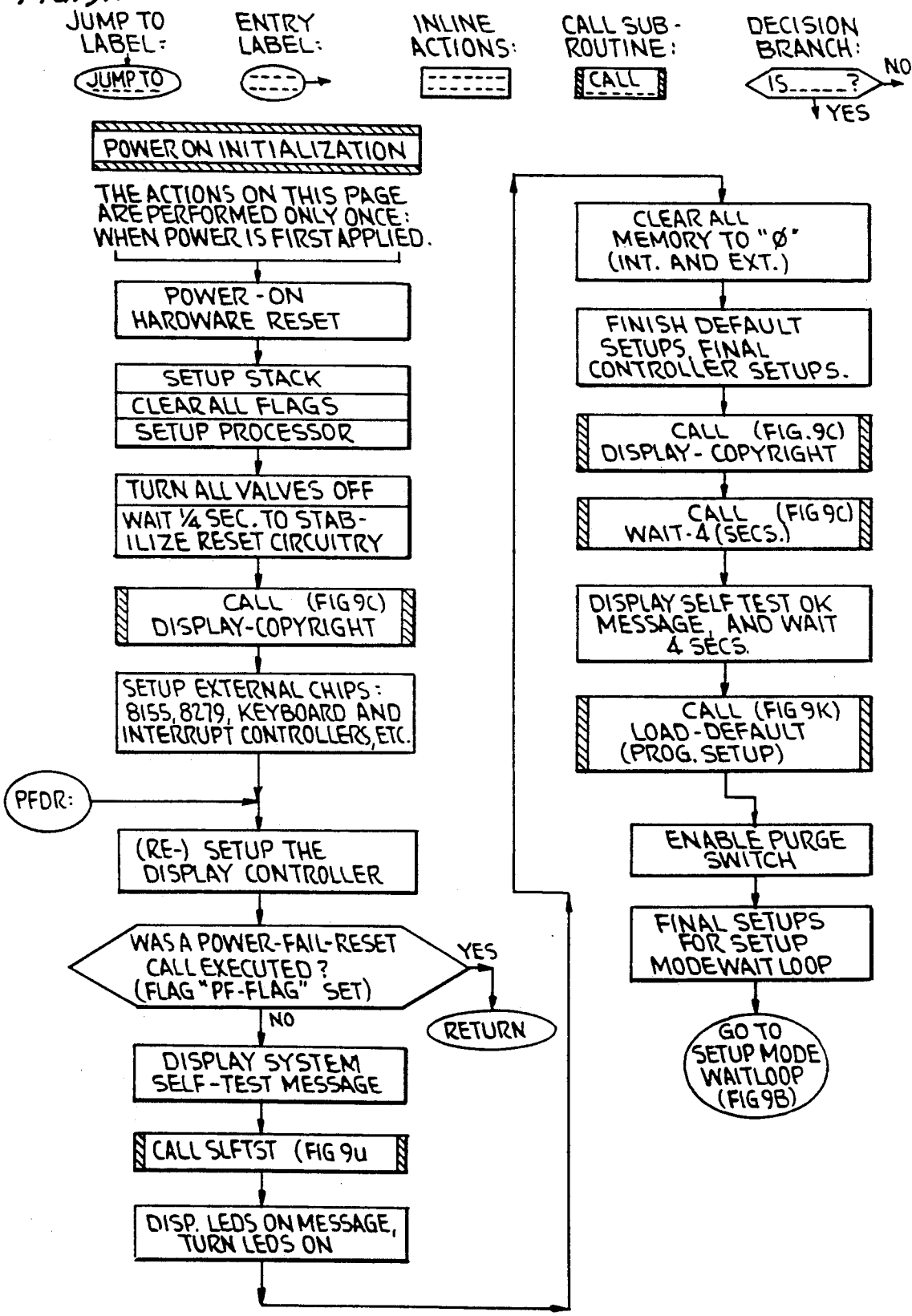

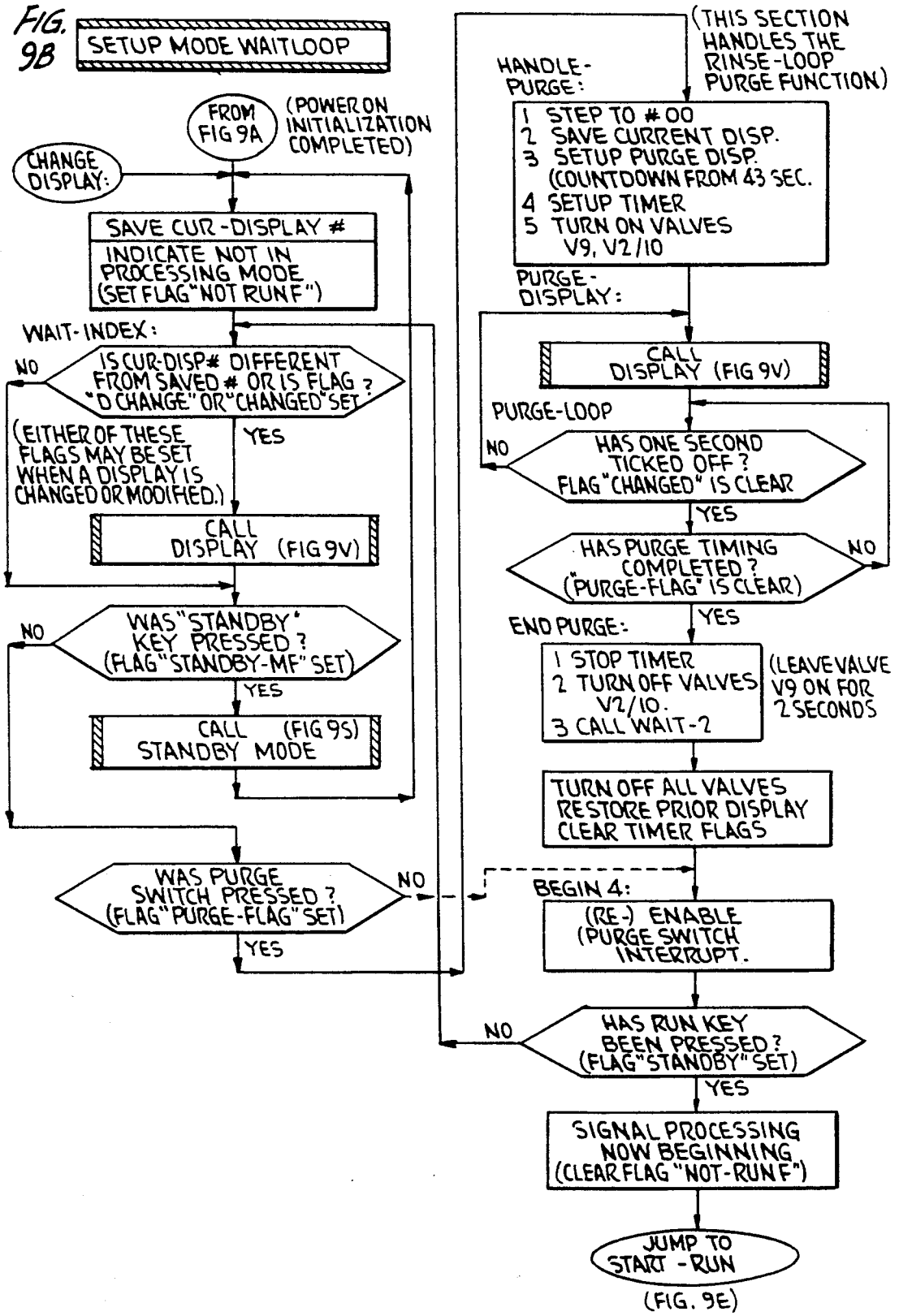

FIG. 9E
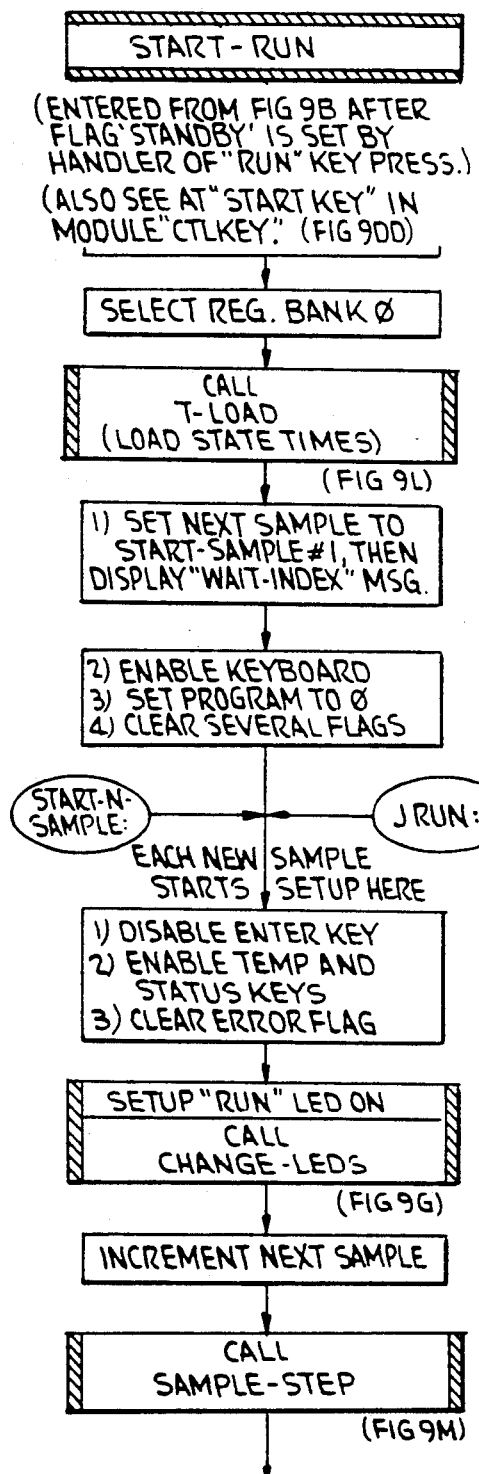
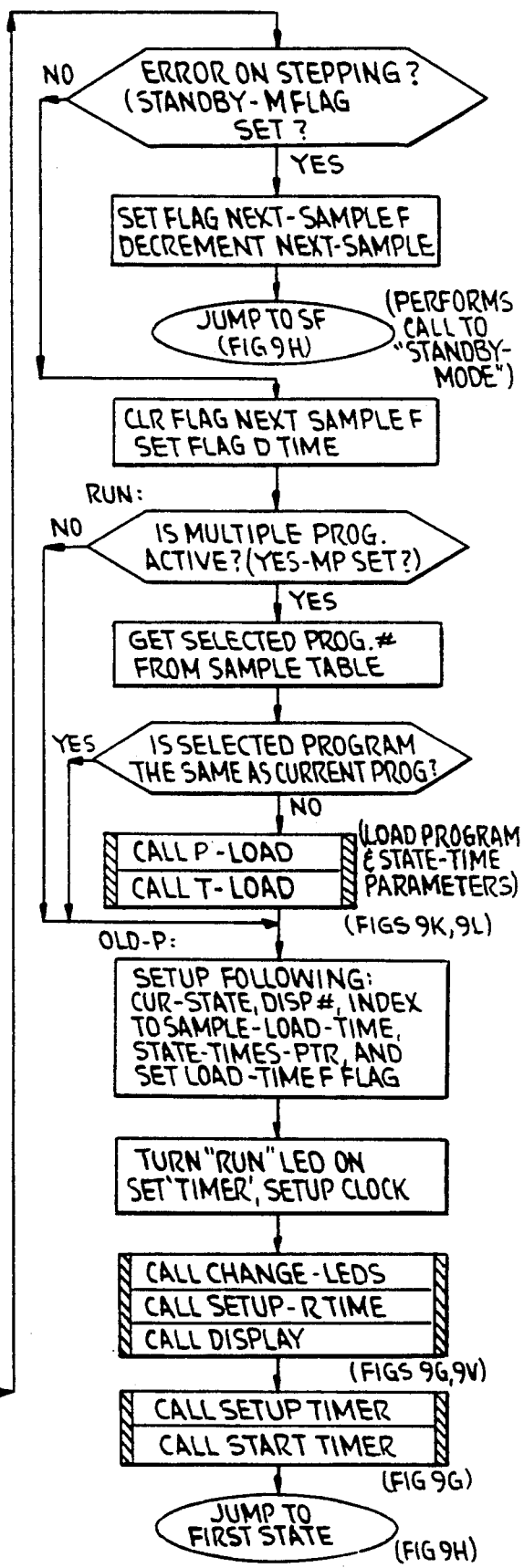

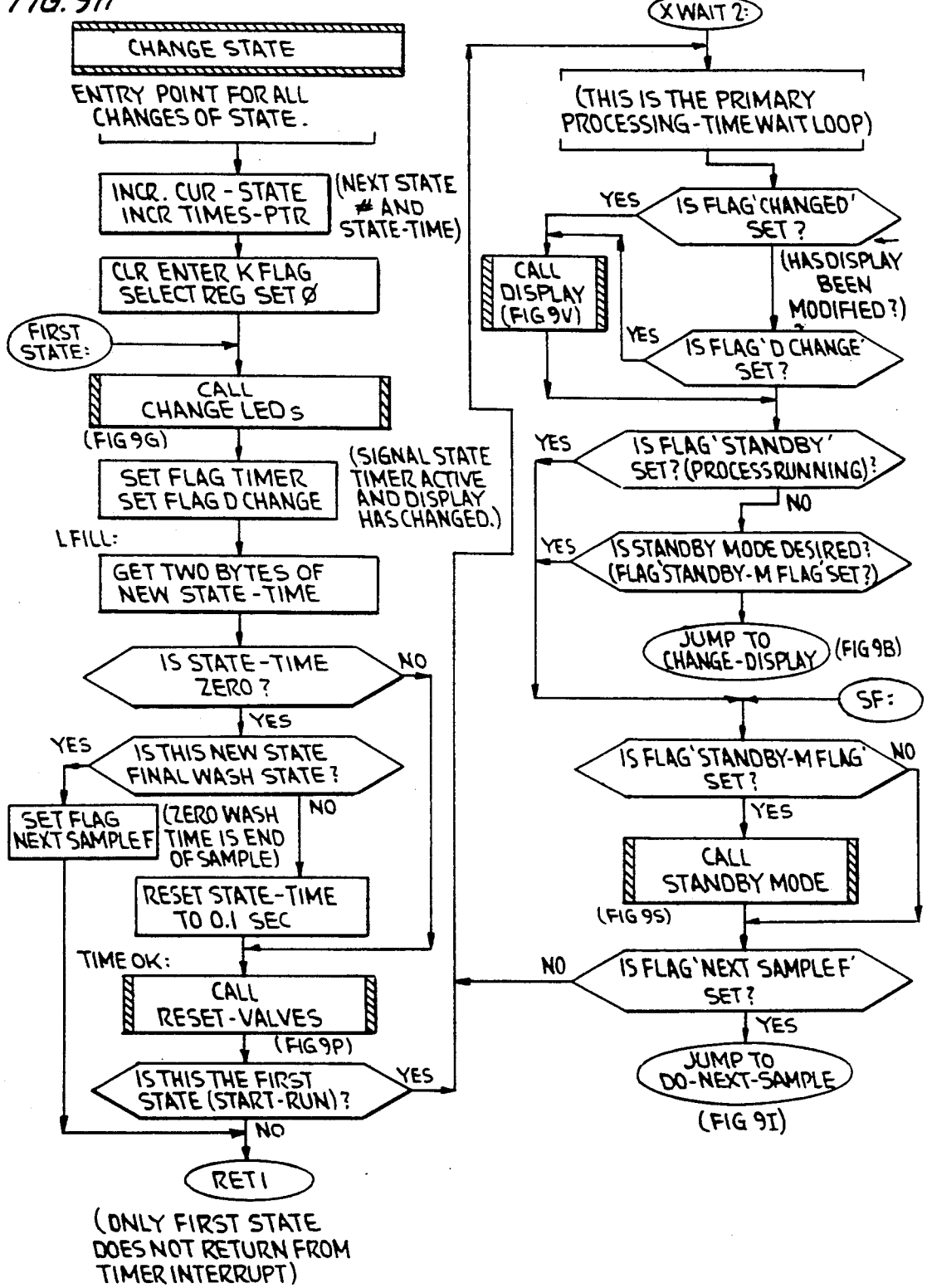

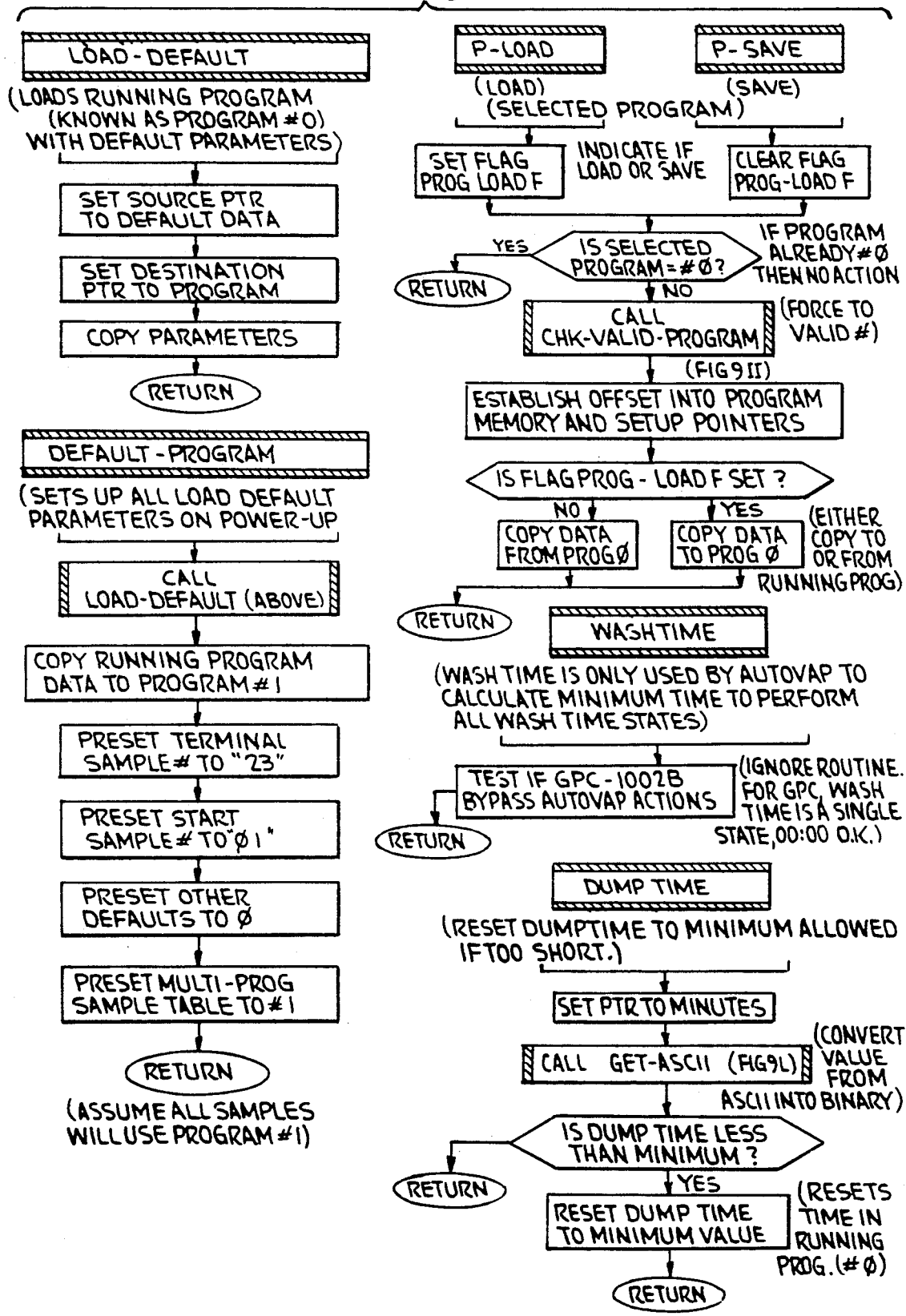

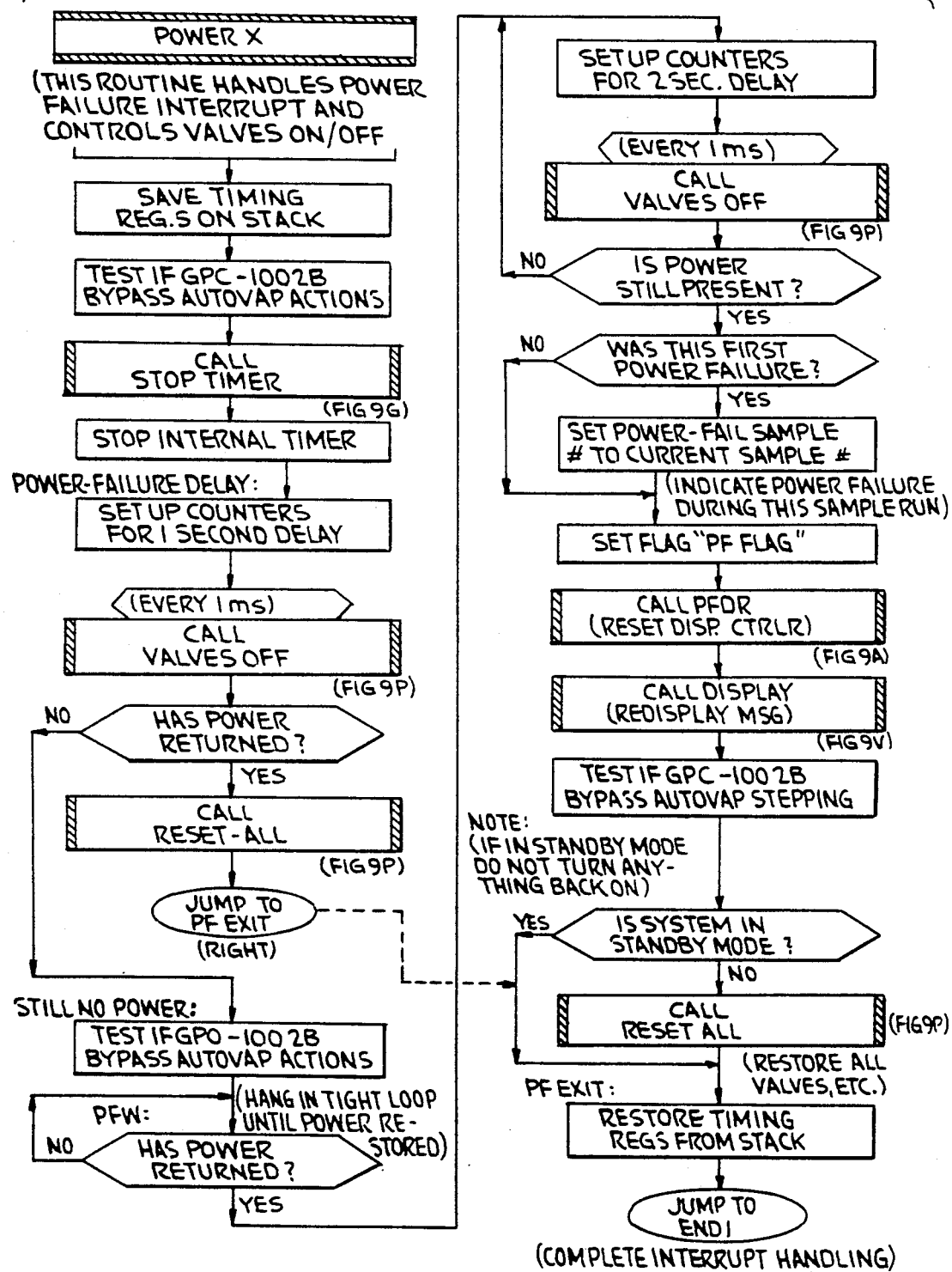

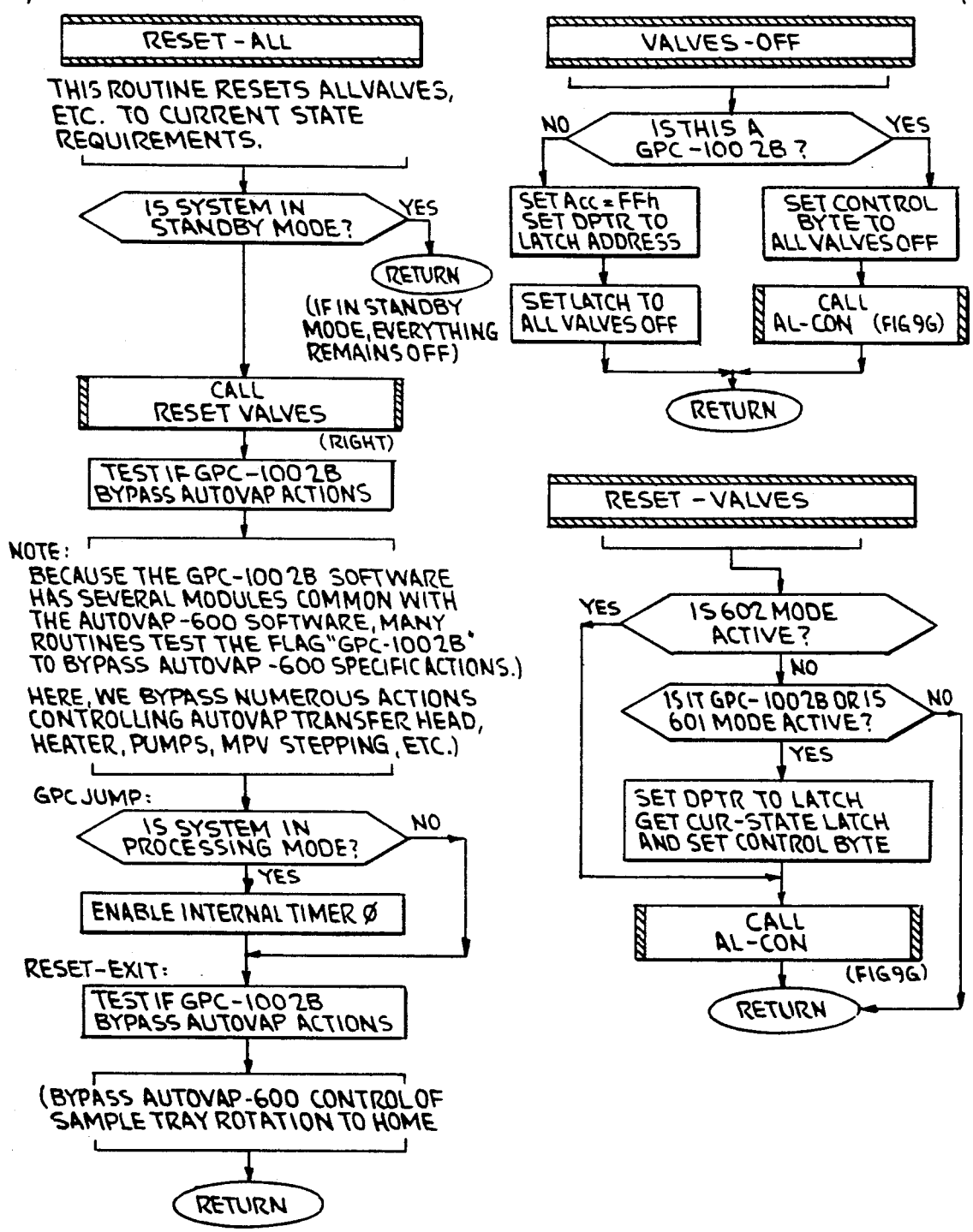

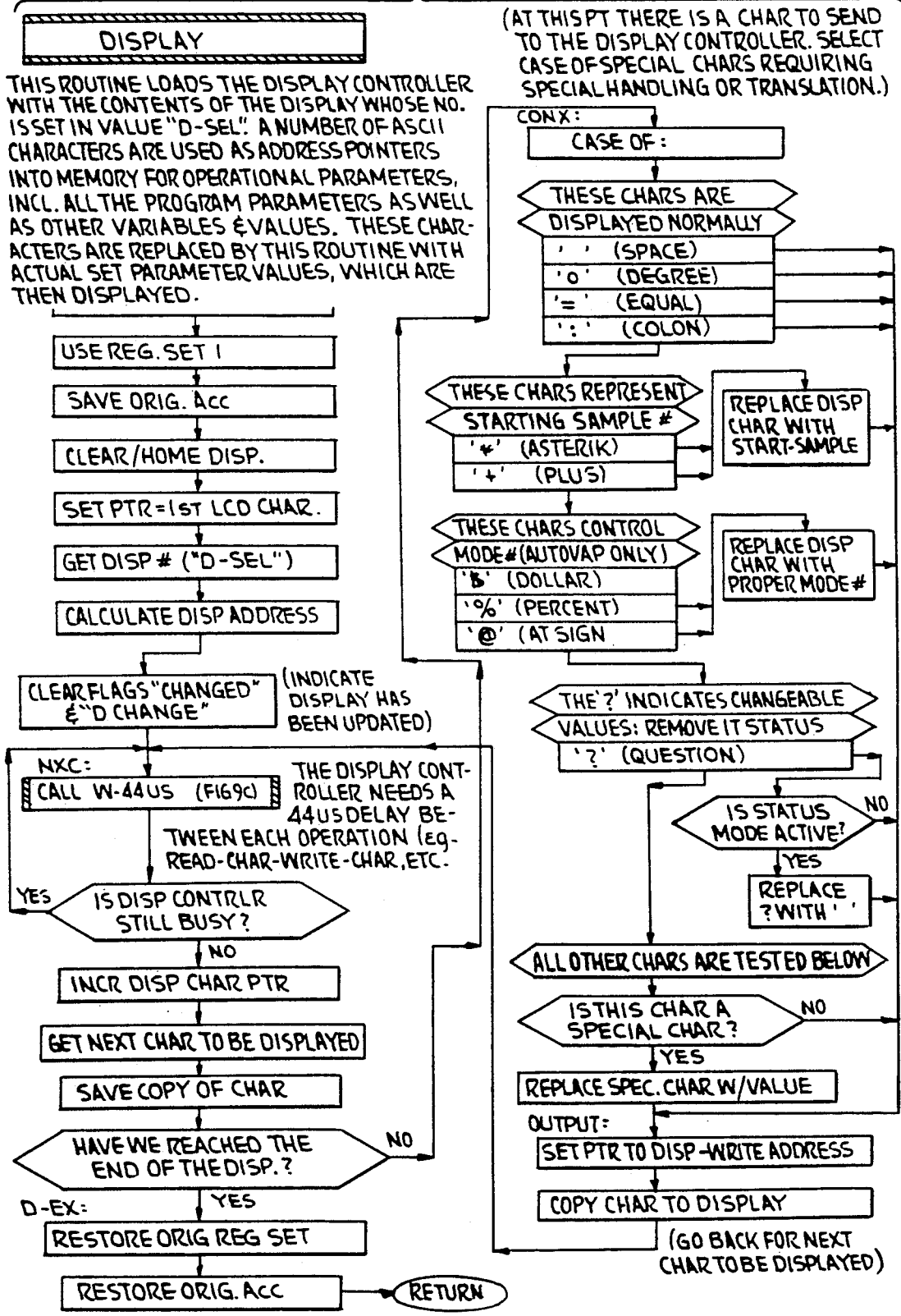

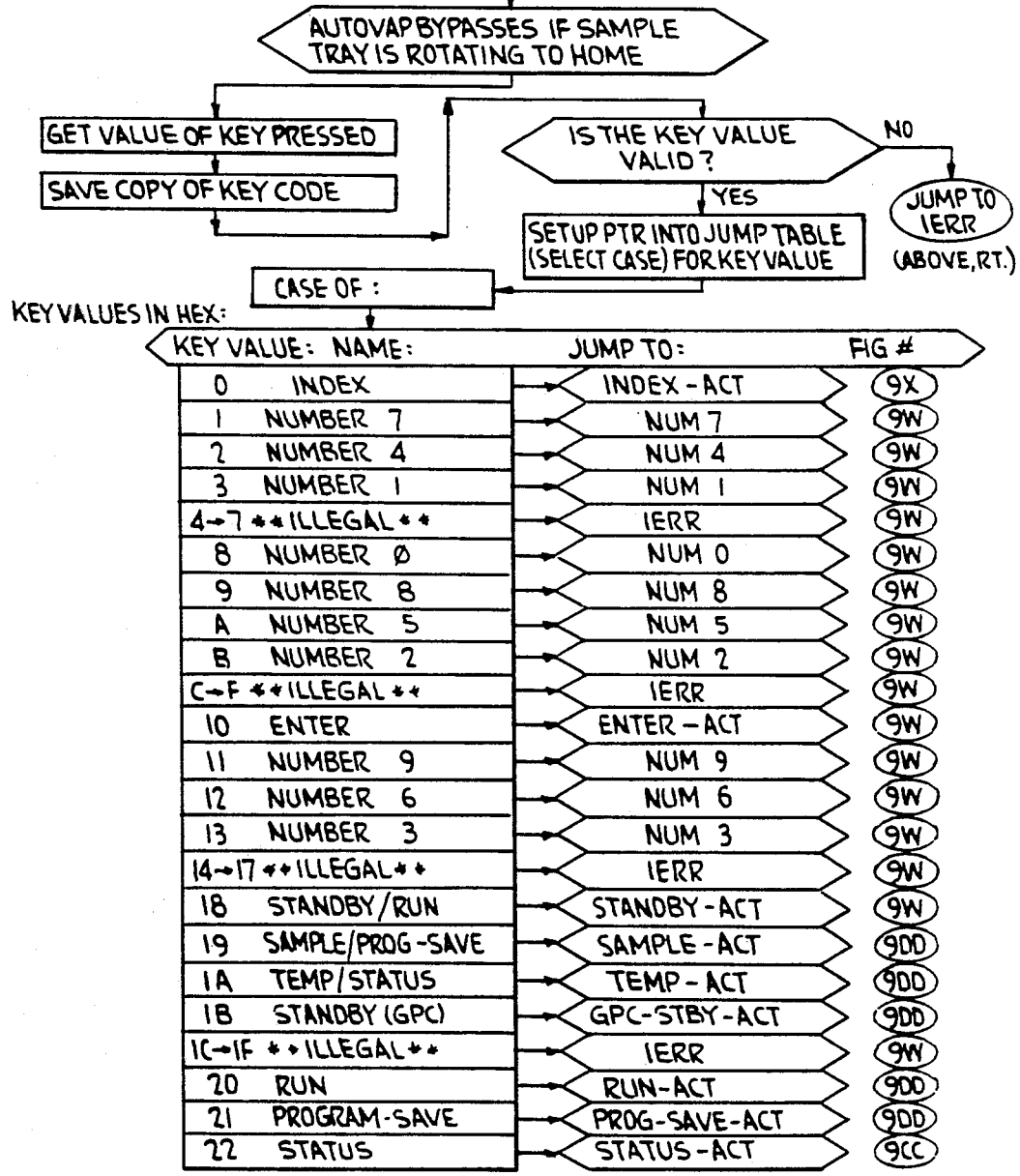

FIG. 9X (CONTINUED)
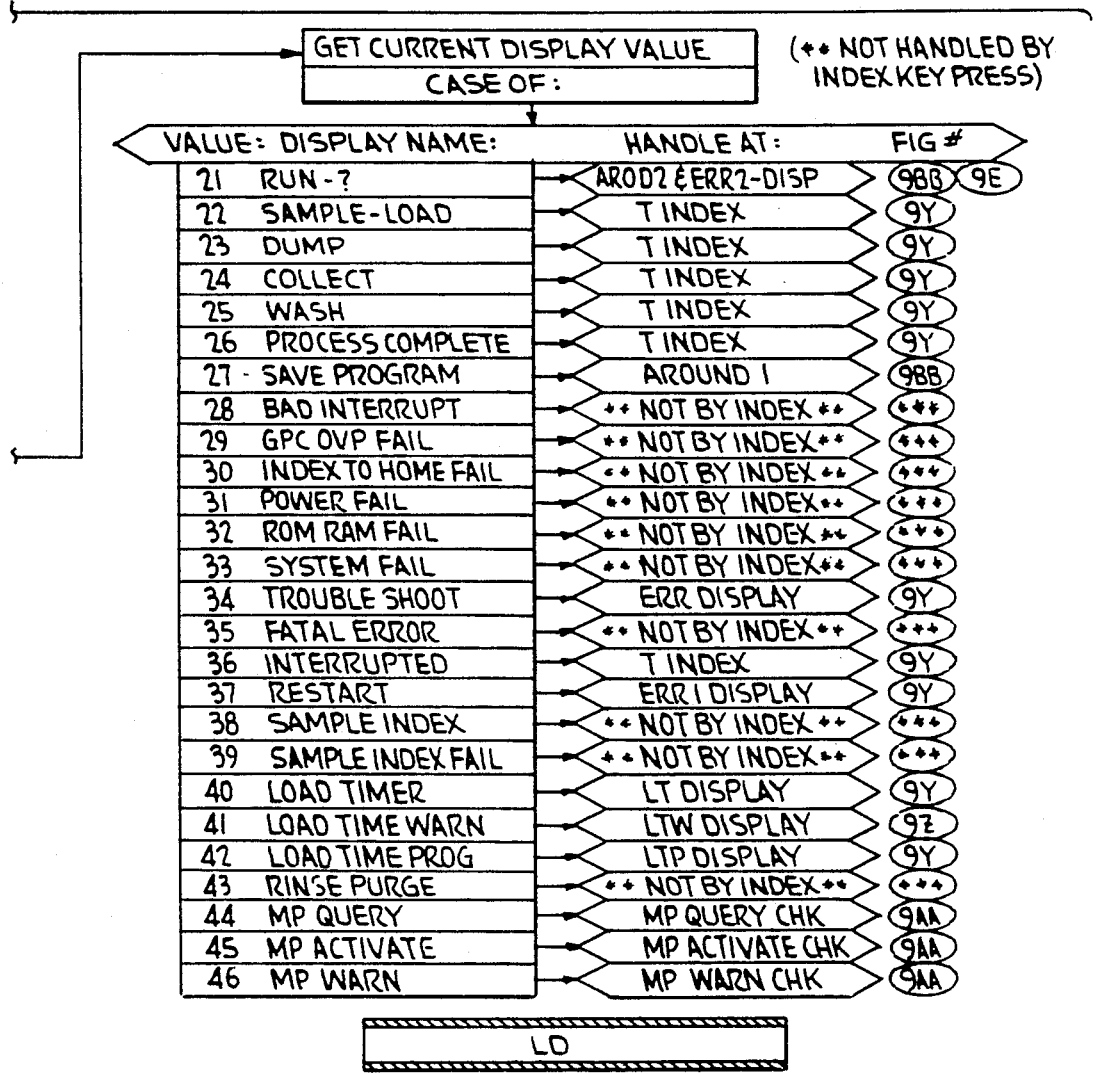
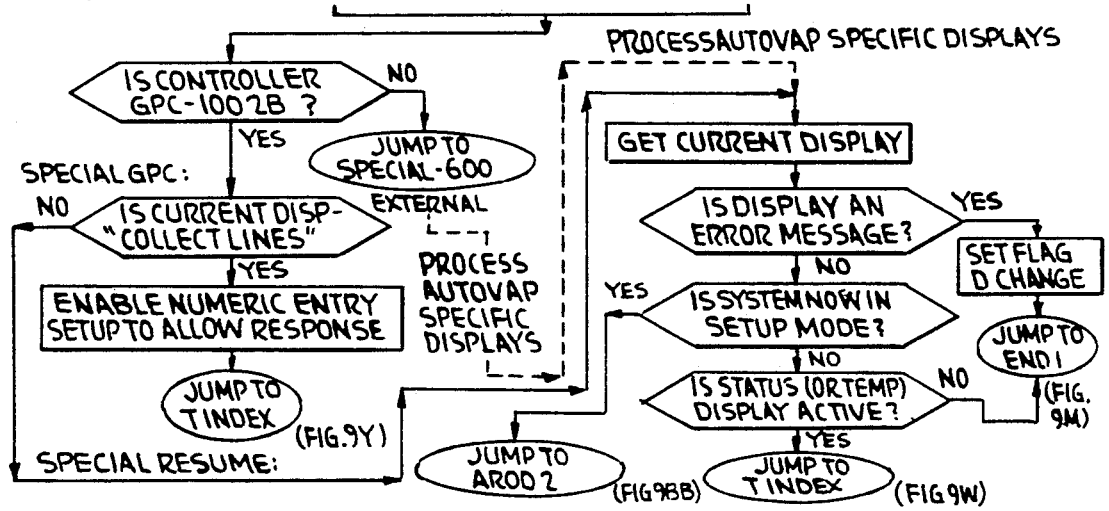

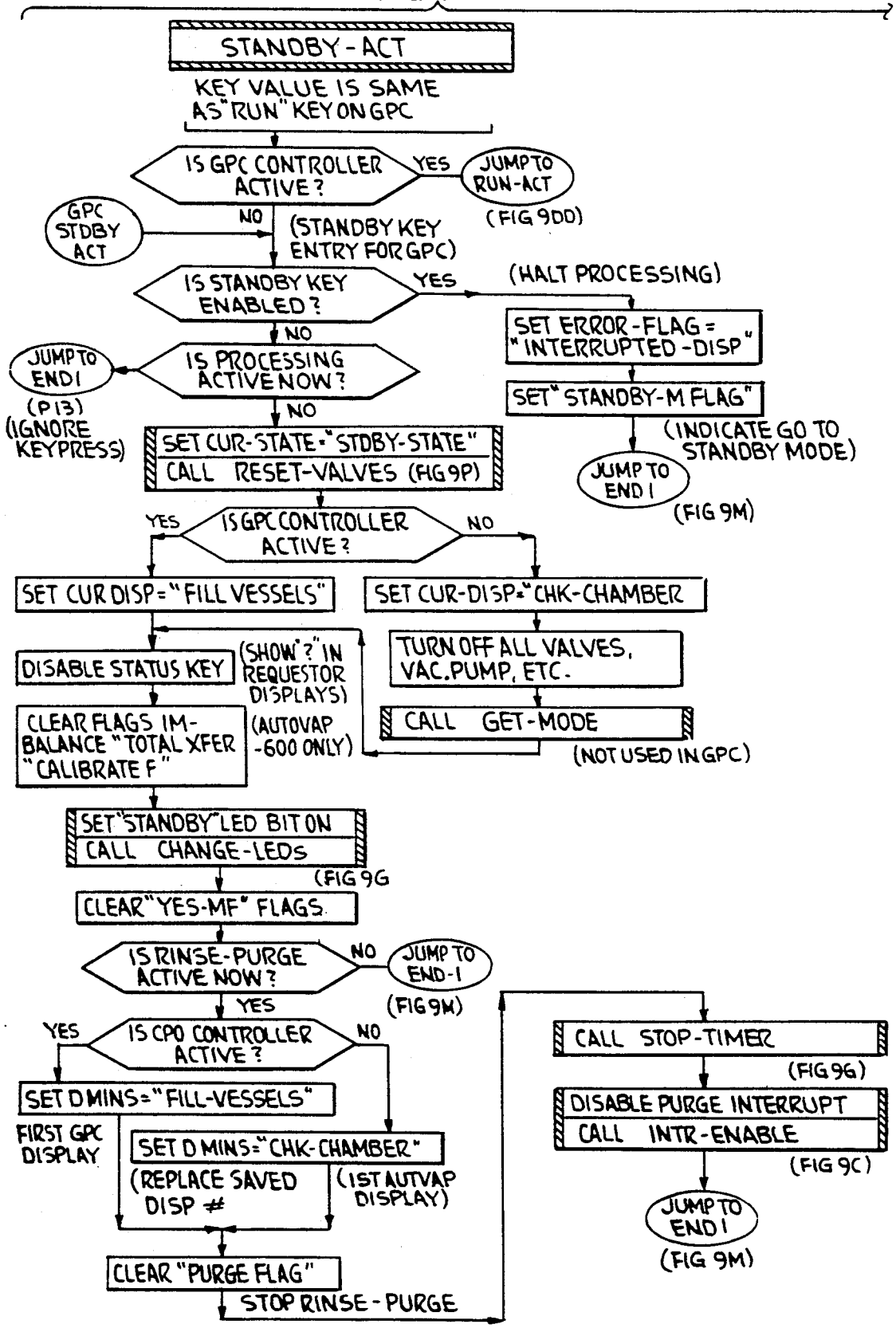

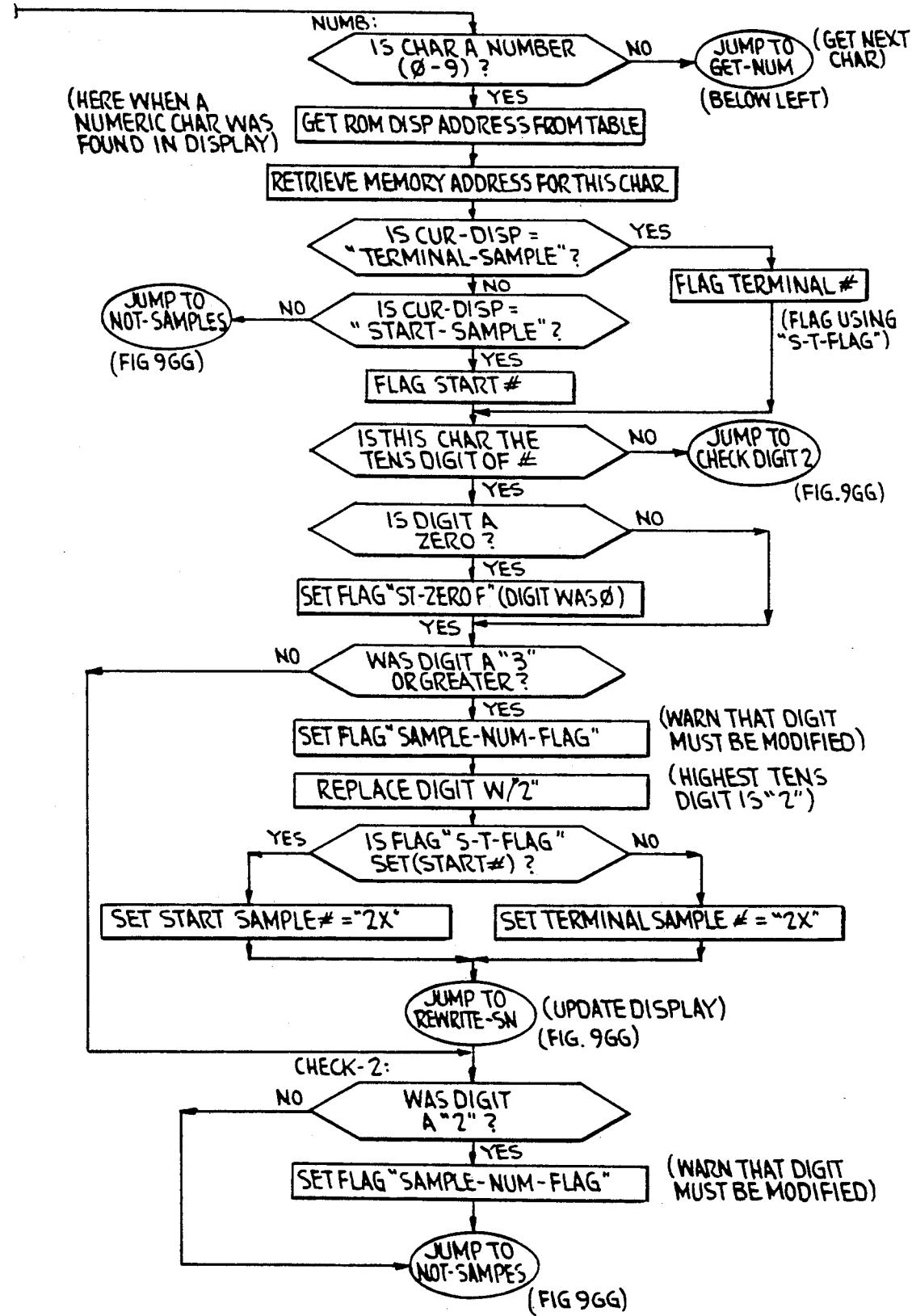

SINGLE-LOOP CHROMATOGRAPHY SYSTEM AND METHOD

BACKGROUND OF THE INVENTION

1. Technical Field

The present invention relates to improvements in automated chromatography systems.

2. Discussion of the Prior Art

Gel permeation chromatography is a well known technique for separating and retaining selected residue components from lipids, sludges, soil, etc. An automated liquid chromatography system employing gel permeation is disclosed in U.S. Pat. No. 3,744,219 (Tindle et al). In the Tindle et al system up to twenty-three individual sample loops or containers are filled with crude sample media, and each sample is sequentially injected into a gel permeation column. As an injected sample is forced through the column, the larger molecules, which are usually the unwanted components of the sample, exit from the column first and are discarded. The smaller molecules to be eluted travel through the gel pores and thereby follow a relatively long and tortuous path to exit from the column after the unwanted larger molecules which are excluded from the pores and therefore travel a more direct path through the column.

Although the Tindle et al automated system represents a significant improvement over prior manually-operated systems, it nevertheless has certain inherent disadvantages and drawbacks. For example, each sample must be loaded into a separate respective sample sizing loop. Since subsequent analysis and processing are greatly simplified if all samples have the same volume, the twenty-three loops must have volumes that are precisely matched within one percent. In addition, the process of loading samples into the respective sample loops is relatively time-consuming, particularly in the case of viscous sample fluids. Further some samples, while awaiting processing, tend to crystallize or otherwise fall out of solution in their respective loops, resulting in flow restrictions in the system flow path and/or loss of sample material. Moreover, after each loop has been filled with sample fluid by a common syringe, the flow paths, leading to the remaining loops, including the loading syringe, must be manually cleansed, thereby increasing the total time required for sample loading.

Another limitation of the Tindle et al system resides in the fact that once the system is placed in the automatic operation mode, no further samples may be added for processing. All of the samples to be processed must be loaded in sequence, starting with the first sample loop, prior to the initiation of automatic processing. Moreover, all samples must be similar in composition.

In systems of the type described herein, wherein sample fluid is transported between different locations by purge gas or other pressurized fluid, there is a tendency for sample storage containers to leak under the relatively high pressure of the purge gas. Apart from aesthetic considerations, the loss of sample fluid by leakage can result in inaccurate processing by causing variations from the standard volume in any given sample.

OBJECTS AND SUMMARY OF THE INVENTION

It is therefore an object of the present invention to provide a method and apparatus for performing automated gel permeation chromatography wherein the aforementioned drawbacks and disadvantages are substantially eliminated.

In accordance with the present invention a single or common sample sizing container or loop is provided. Each sample is placed in the common sample loop immediately prior to injection of that sample into the chromatography column, thereby eliminating the requirement for multiple precisely matched sample loops. Since a common sample loop is used to size each sample, the volume is identical for each sample injected into the chromatography column. Before sizing, each sample is stored in its own storage flask, the flasks being automatically sequentially accessed to directly feed a portion of the contained sample medium to the common sample sizing loop. Accordingly, the present invention eliminates the need for a common loading flask that must be carefully cleaned between sample loadings in the Tindle et al system. The overall result is a greatly reduced total sample loading time.

In order to assure that each sample injected into the chromatography column has the same volume, the common sample sizing loop must be filled with each sample. To assure that the loop is filled, the total loading flow path between valves located upstream of the sample sizing loop must be filled during loading of the loop. This tends to be wasteful of sample fluid since fluid remaining in the flow path but outside the sizing loop must be purged from the system after the sample is injected into the chromatography column and before the next sample is loaded. Accordingly, one aspect of the present invention includes minimizing the total volume of the loading flow path by employing the minimum possible length of tubing between the valves used to control sample loading.

By introducing each sample into the common sample sizing loop immediately prior to injecting that sample into the chromatography column, the possibility of crystallization of the sample in the loop is substantially eliminated. Moreover, rinsing of the entire loading flow path, from the sample storage flask to the common sample loop, may be effected automatically in a very short period of time.

The system may begin processing with any selected one of twenty-three samples, rather than being limited to begin with the first sample. Further, processing of a sample may begin before all of the sample storage flasks have been filled. The samples may also be selectively grouped such that samples in different groups are processed under the control of different respective timing programs.

Each sample storage flask is suspended from a respective support arm extending outwardly from the chromatographic unit housing. A container closure member is secured flush against the underside of the support arm and has a vertical bore defined entirely through its axial length. The bottom portion of the insert bore is of smaller diameter and is threaded to receive the upper end of its storage flask in a threaded fit engagement. The upper end of the insert bore is of shorter length and larger diameter, thereby defining an upwardly facing annular shoulder at the juncture of the two bore sections. A closure insert fits flush within the upper bore section and has an axially-extending bore defined therein in concentric alignment with the closure member bore. The bottom section of the insert bore is relatively short and has a slightly larger diameter than the diameter of the upper bore section in the closure member. An O-ring is disposed in the bottom section of the insert bore and is urged against the annular shoulder in the closure member bore when the insert member is properly seated in the closure member. The upper insert bore section is threaded to receive a threaded bottom leg of a hollow connector disposed above the support arm in registration with an access hole defined in the support arm and aligned with the insert and closure member bores. A sample pick-up tube extends through the connector, the access hole and the concentric bores in the insert and closure members into the flask. A second tube for selectively delivering solvent and purge gas to the flask terminates at the connector so as to deliver its fluid to the hollow connector interior. The delivered fluid flows in an annular path surrounding the pick-up tube into the flask via the concentric bores in the insert and closure members. The closure member is secured against the underside of the support arm by means of screws so as to tightly engage the insert member in its seated position in the closure member bore.

BRIEF DESCRIPTION OF THE DRAWINGS

These and other objects, features and many of the attendant advantages of the present invention will be appreciated more readily as they become better understood from a reading of the following description considered in connection with the accompanying drawings wherein like parts in each of the several figures are identified by the same reference characters, and wherein:

FIG. 6 is a view in perspective of the chromatography module housing of the system of FIG. 1;

FIG. 7 is an exploded view in perspective of a typical support arm extending from the housing of FIG. 6;

FIG. 8 is a view in vertical section of a connector employed in the support arm assembly of FIG. 7.

DESCRIPTION OF THE PREFERRED EMBODIMENT

Figure 1:
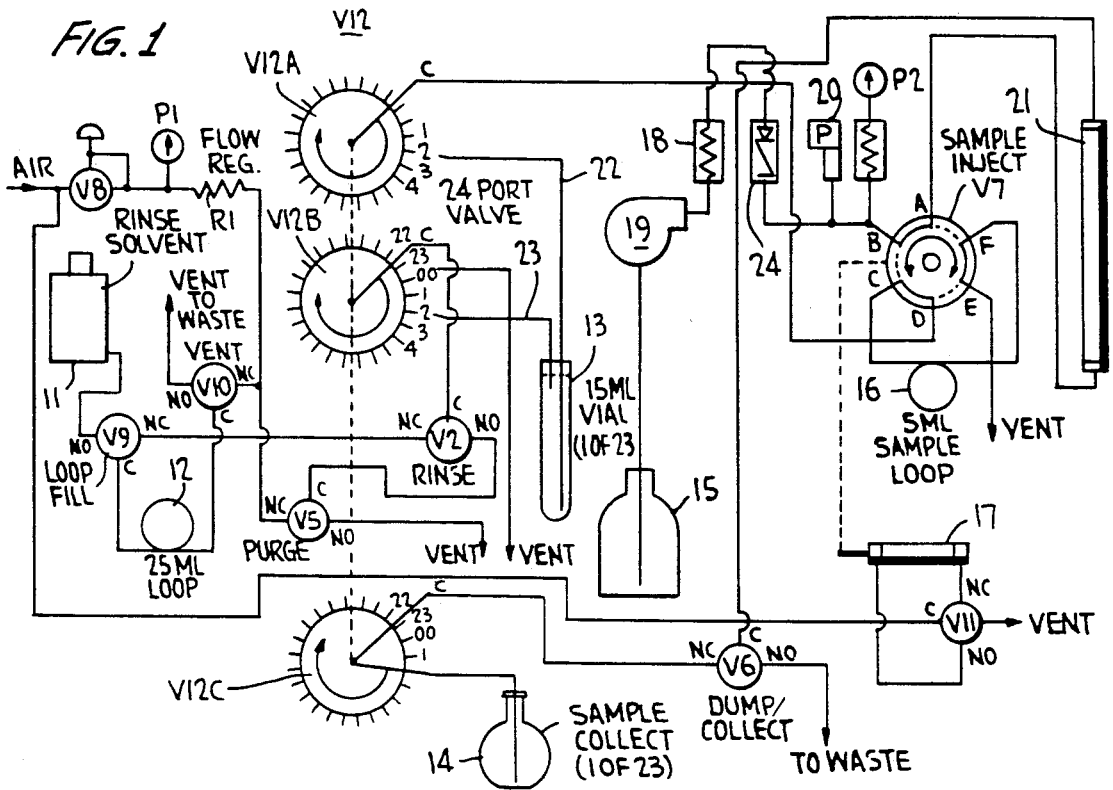
FIG. 1 is a flow schematic diagram of a preferred embodiment of the chromatography system of the present invention.

Reference is initially made to FIG. 1 of the accompanying drawings which is a flow diagram of a preferred embodiment of the chromatography system of the present invention. A chromatography column 21 is utilized to separate components from sample fluids passed therethrough in a conventional manner. In the preferred embodiment, column 21 is typically made of glass with teflon fittings and packed with spherical beads of styrene divinyl benzene three percent cross-linked polymer. Smaller molecules enter and exit from the gel pores following a longer path through the column and elute later than larger molecules that are excluded from the pores and travel a more direct path to the top of the column. The bottom or input end of the column 21 is connected by a fluid conduit to a port A of the sample inject valve V7 which is a six-port, two-position valve such as the type disclosed in U.S. Pat. No. 2,846,121. In one position of valve V7 (i.e., the load position shown in solid lines), ports A and B are in flow communication, ports C and D are in flow communication and ports E and F are in flow communication. When valve V7 is in the run position, ports A and F are in flow communication, ports D and E are in flow communication and ports B and C are in flow communication. Port E is permanently connected to a vent or waste container. Operation of the sample inject valve V7 is controlled by an air cylinder 17, the piston in which is moved under the control of a piston control valve V11. Valve V11 has a common port C, a normally closed port NC, a normally open port NO and a vented port. When valve V11 is unactuated, the normally closed port is in flow communication with the vented port while the common port is in flow communication with the normally open port. Upon actuation of valve V11, its common port is in flow communication with the normally closed port while the normally open port is in flow communication with the vent port.

A common sample sizing loop 16 is connected between ports C and F of the sample inject valve V7. In the preferred embodiment sample loop 16 has a five milliliter volume, although this is not a limiting characteristic of the present invention. The volume of sample loop 16 must be sufficient to permit the sample contained therein to be properly processed through column 21. Sample loop 16 serves as a common sizing container for sample material to be analyzed and, in this regard, may take the form of any suitable container. It should be noted, however, that a loop of fluid-conducting tubing is particularly useful as a sizing container in the present invention.

Multiple sample storage containers 13 (only one of which is illustrated in FIG. 1 to facilitate understanding of the invention) take the form of respective test tubes or flasks in which sample material to be analyzed is stored. The outer surface of each container 13 is threaded at its upper end to be engaged by a suitable respective threaded closure member. A respective sample pick-up tube 22 extends from the bottom of each container 13 to a respective individually accessible port of a first wafer or section V12A of a multiple port sample selection valve V12. The length to which the pick-up tube 22 extends in container 13 may be adjustable. Valve V12 has three simultaneously actuable and substantially identical sections V12A, V12B and V12C, each section having a common port C that is selectively placed in flow communication with twenty-four individually accessible ports numbered "00" through "23". The twenty-four individually accessible ports at each section correspond to one more than the number of sample storage containers 13 with the "00" port serving as a neutral position for valve V12. In the flow diagram of FIG. 1 the single sample storage container 13 is shown with its pick-up tube 22 connected to individually accessible port "2" of valve section V12A. The common port of valve section V12A is connected to port D of sample inject valve V7 so that sample fluid from the sample storage container 13 selected by valve V12 can pass through the common port of valve section V12A to port D of the sample inject valve where, in the load position of valve V7, the sample passes from port C of the valve into the sample loop 16.

Each sample storage container 13 is provided with a fluid delivery tube 23 extending from the upper portion of the container to a corresponding individually accessible port of valve section V12B. In particular, the individually accessible port at V12B to which delivery tube 23 is connected corresponds to the individually accessible port in valve section V12A to which the pick-up tube 22 for the corresponding sample storage container 13 is connected. The common port C for valve section V12B is connected to receive either purge gas or rinse liquid in a manner described below.

From the foregoing it will be seen that valve sections V12A and V12B are used to provide sample selection. Valve section 12A connects each of the twenty-three sample pick-up tubes 22 to either the sample loop 16 or to vent, depending upon the position of sample inject valve V7. Valve section V12B connects each of the twenty-three delivery tubes 23 to the supply line for purge gas or rinse liquid. The "00" port of valve section V12B is connected to vent.

The third valve section V12C has its individually accessible ports connected to respective sample collection containers 14, there being twenty-three such sample collection containers but only one is illustrated in FIG. 1 to facilitate understanding of the system. The common port C for valve section V12C is connected to a normally closed port of a dump/collect valve V6. Valve V6 also has a common port which is connected to the normally closed port when the valve is actuated, and a normally open port to which the common port is connected when the valve is unactuated. The normally open port of valve V6 is connected to waste or vent. The common port of valve V6 is connected to the upper end of the chromatography column 21. It will be appreciated, therefore, that valve section V12C connects each of the twenty-three sample collection containers 14 to the dump/collect valve V6 in order to permit the eluted component of the processed sample to be collected from column 21. As each sample is selected for processing, valve V12 is stepped by means of a solenoid in all three valve sections simultaneously. Sample position feedback is provided to the controller unit in a manner described below.

A reservoir 15 for sample solvent material has solvent material selectively drawn therefrom by means of a solvent pump 19 that is selectively actuable. Solvent pump 19 is a positive displacement piston pump having an adjustable flow rate. Typically the sample solvent reservoir 15 has an eight liter capacity. The sample solvent fluid is used to drive the sized sample in sample loop 16 through the chromatography column 21. In this regard, the outflow from sample solvent pump 19 is directed to port B of the sample inject valve V7. The flow path between pump 19 and port B of valve V7 includes a snubber 18, and a check valve 24. A pressure gauge P2 measures the pressure at the outflow side of check valve 24, and an over-pressure switch 20 monitors the pressure at the same location. If the monitored pressure exceeds a predetermined maximum (e.g., 20 psi), over-pressure switch 20 is actuated to provide a signal to the system controller which responds by terminating processing and shutting off the solvent pump 19. Snubber 18 serves to protect the pressure gauge P2 and prevent fluctuations of the gauge indicator.

The common port C for sample select valve section V12B is connected to the common port C of rinse valve V2. Rinse valve V2 is the same type of valve described above in relation to valve V6 and has its normally open port connected to the common port of a purge valve V5 also of the same general type. The normally closed port of rinse valve V2 is connected to the normally closed port of a loop fill valve V9, also of the same general type. Purge valve V5 has its normally open port vented while its normally closed port is connected to receive a supply of purge gas under pressure. The purge gas is supplied through a pressure and flow regulation path including a pressure regulator valve V8 and a flow restrictor R1. A pressure gauge P1 monitors the pressure of the purge gas downstream of pressure regulator valve V8. The normally closed port of vent valve V10 is also connected to receive the regulated pressurized purge gas, the normally open port of that valve being vented.

A rinse solvent reservoir 11 is connected so that outflow therefrom is delivered to the normally open port of loop fill valve V9. The common port of loop fill valve V9 is connected to one side of a rinse loop 12 which, in the preferred embodiment, is a length of tubing having a volume of 25 milliliters. When it is desired to deliver rinse solvent from loop 12 to the common flow path, valves V2, V9 and V10 are actuated, thereby permitting the pressurized purge gas to force the rinse solvent from the rinse loop 12. When these valves are unactuated, the rinse loop is gravity filled with rinse solvent from reservoir 11.

Operation of the flow components illustrated in FIG. 1 proceeds in timed relation under the control of the programmed system microprocessor described subsequently. For a broad overview of system operation, the following description is presented.

Solvent pump 19 is actuated prior to sample processing until the solvent pressure and flow rate, as measured at the output of check valve 24, stabilize at the desired levels. During this time sample solvent is pumped from solvent reservoir 15 through snubber 18, check valve 24 and sample inject valve V7 (port B), out through port A of valve V7 and through the column 21 to a waste container via valve V6. The pressure of the solvent is indicated by pressure gauge P2. If the system pressure exceeds a predetermined maximum (e.g., 20 psi) at any time during solvent pump operation, the over pressure switch 20 generates a signal to the system controller which halts operation by de-energizing pump 19 and displaying an error indication for the operator.

Sample processing is initiated by actuation of the "run" key (described below). The sample select valve V12 is actuated to the position corresponding to the first sample to be processed as pre-programmed by the operator. Gas purge valve V5 is energized to allow the purge gas to flow through unactuated rinse valve V2 and into the selected sample container 13 via the appropriate individually accessible port in section V12B of the sample select valve. The purge gas enters the top of the sample container 13 via delivery tube 23 and forces sample fluid out of the container via pick-up tube 22. The sample fluid flows through valve section V12A and ports D and C of sample inject valve V7 into the common sample sizing loop 16. Purge gas flow rate and sample load time are calibrated prior to sample processing to assure that a small portion of the sample flows through the sample loop to vent, leaving the sample loop completely filled with sample fluid. A small amount of sample fluid is also left in the tube connecting the common port of valve section V12A with port D of the sample inject valve V7. This tube is maintained as short as possible in order to minimize the amount of sample fluid retained therein since that retained fluid is ultimately discarded.

At the end of the sample load time the piston control valve V11 is energized to actuate air piston 17, thereby switching the sample inject valve V7 from its load position (i.e., solid lines in FIG. 1) to its run position (i.e., dashed lines in FIG. 1). The programmable dump interval is initiated at this time. Purge valve V5 remains actuated briefly after the dump interval commences in order to drive out to vent any sample fluid remaining in container 13 and pick-up tube 22, and in the tubing between the common port of valve section V12A and port D of valve V7. Solvent fluid is pumped from the sample solvent reservoir 15, through the sample inject valve V7 to ports B and C, through sample loop 16 and into the bottom of column 21 via ports F and A. The sample solvent from reservoir 15 thus drives the sample fluid previously loaded into the common sample loop 16 through column 21. The dump/collect valve V6 is not actuated at this time so that the initial column effluent (i.e., from the top of the column) is directed to a waste container.

The initiation of the dump interval also results in rinse solvent fluid from rinse loop 12 being driven through the path taken by the previously loaded sample. In particular, loop fill valve V9, vent valve V10 and rinse valve V2 are energized, thereby permitting purge gas to force rinse solvent from loop 12, through valves V10 and V2 and valve section V12B into the selected sample container 13. The rinse solvent rinses container 13 and is forced through pick-up tube 22, valve section V12A, and ports D and E of the sample inject valve V7 to waste. This results in a rinsing or cleansing of the common line between section V12A of the sample select valve and port D of sample inject valve V7 through which the next selected sample must pass when loaded into the common sample sizing loop 16.

After an appropriate time interval to effect cleansing, vent valve V10 and rinse valve V2 are de-energized, while loop fill valve V9 is permitted to remain energized briefly to aid in refilling the gravity-filled rinse loop 12. Purge valve V5 is energized to force the remainder of the rinse solvent fluid out to the waste container at port E of sample inject valve V7. Rinsing thus takes place during the dump interval resulting in a minimization of the dump interval (i.e., typically on the order of ninety seconds). At the end of the rinsing portion of the interval, purge valve V5 is de-energized. Rinsing can also be initiated during various servicing and maintenance prompts by actuating an appropriate rinse purge switch described subsequently.

At the end of the dump interval, dump/collect valve V6 is energized to permit the effluent from column 21 to be directed through section V12C of the sample select valve and into the appropriate sample collection container 14. At the termination of the prescribed collection interval, dump/collect valve V6 is de-energized so that the column effluent may be directed to a waste container for the duration of the wash interval. At the termination of the wash interval, or at the termination of the collect interval if the wash interval is selected to be zero, processing continues with the next sample in the manner described above. If no further samples are to be processed, the solvent pump 19 is de-energized and processing is terminated.

Operation of the flow components during the system calibration mode is identical to normal run operation described above until the end of the collect interval. Instead of proceeding to a wash interval, the collect interval is reset to the programmed value, the sample select valve V12 is stepped to the next position, the dump/collect valve V6 remains energized, and sample collection continues with the next sample in sequence. The process continues in the manner described until all samples are collected and processed.

Figure 2:
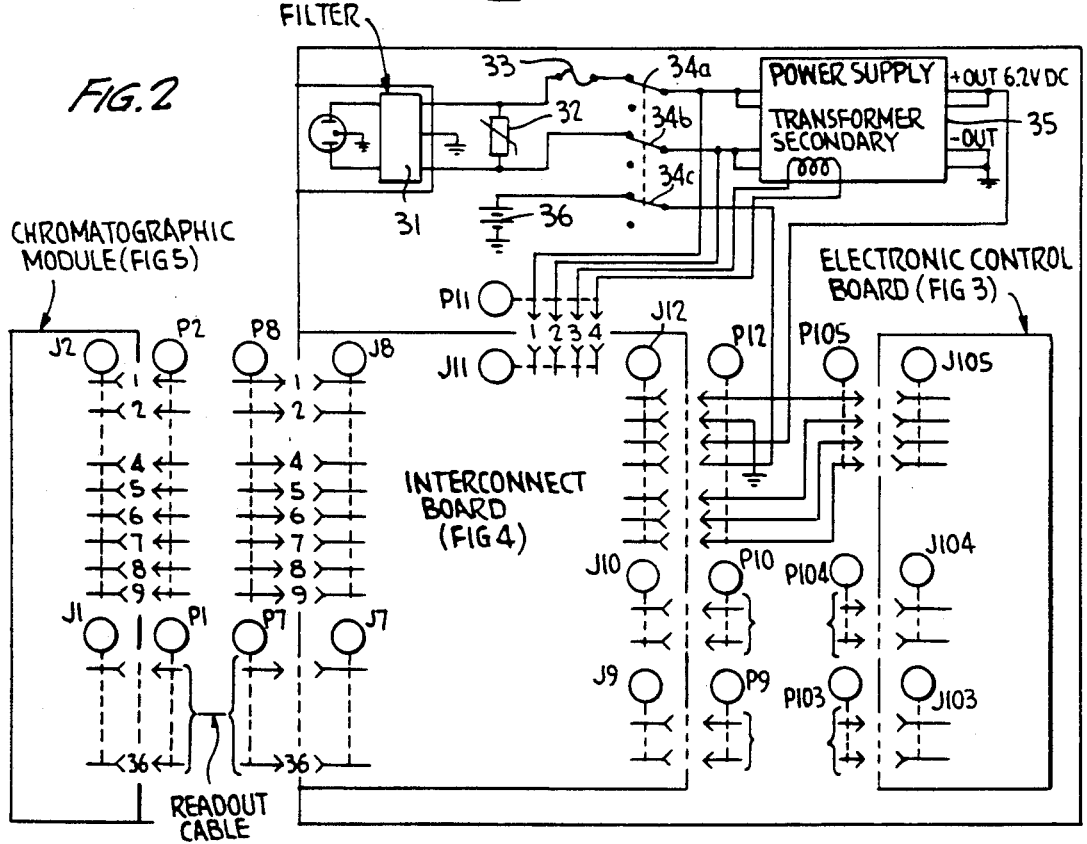
FIG. 2 is an electrical block diagram of the system for FIG. 1.
Figure 4:
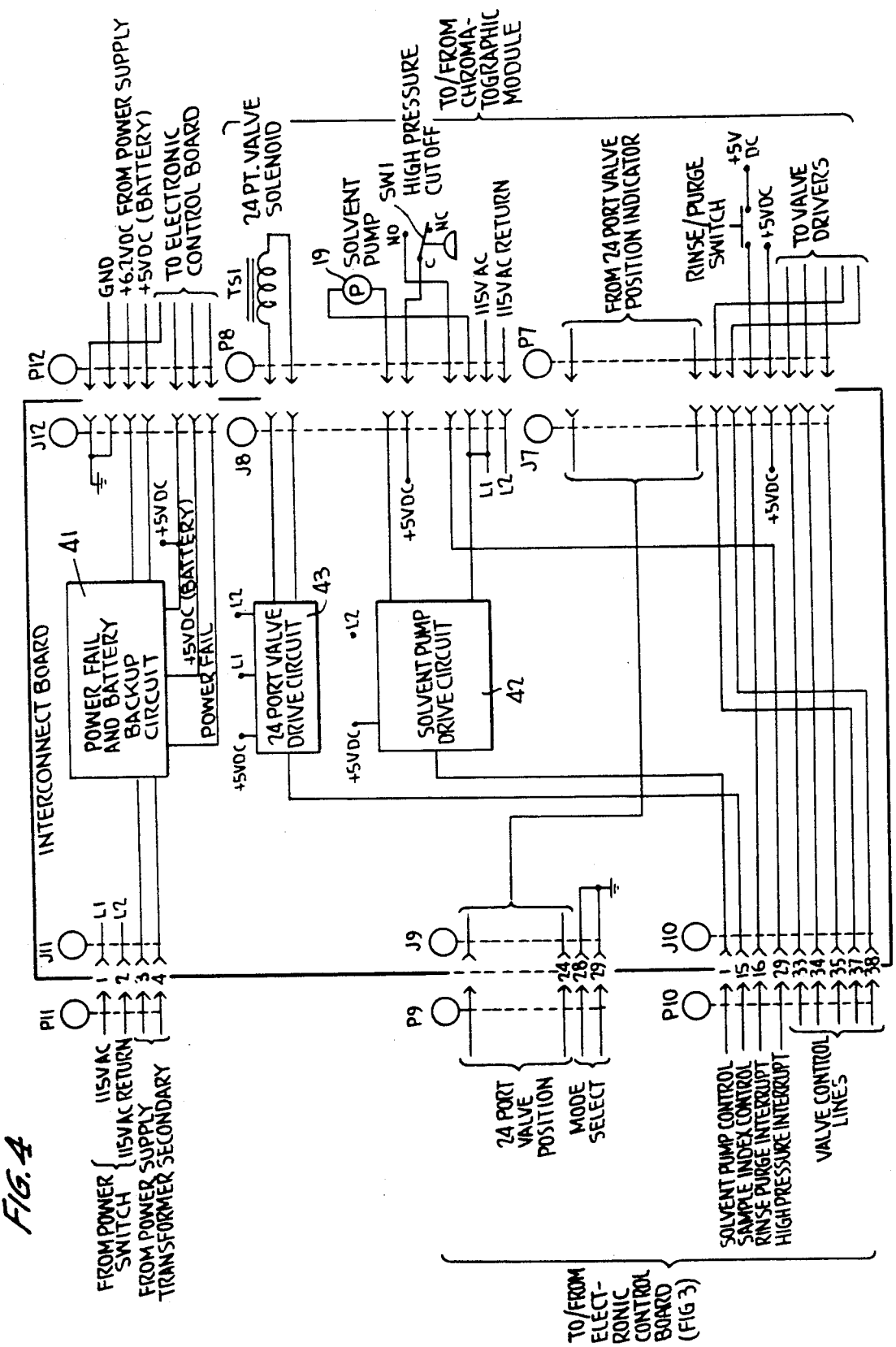
FIG. 4 is an electrical block diagram of the interconnect board portion of the system of FIG. 1.
Figure 5:
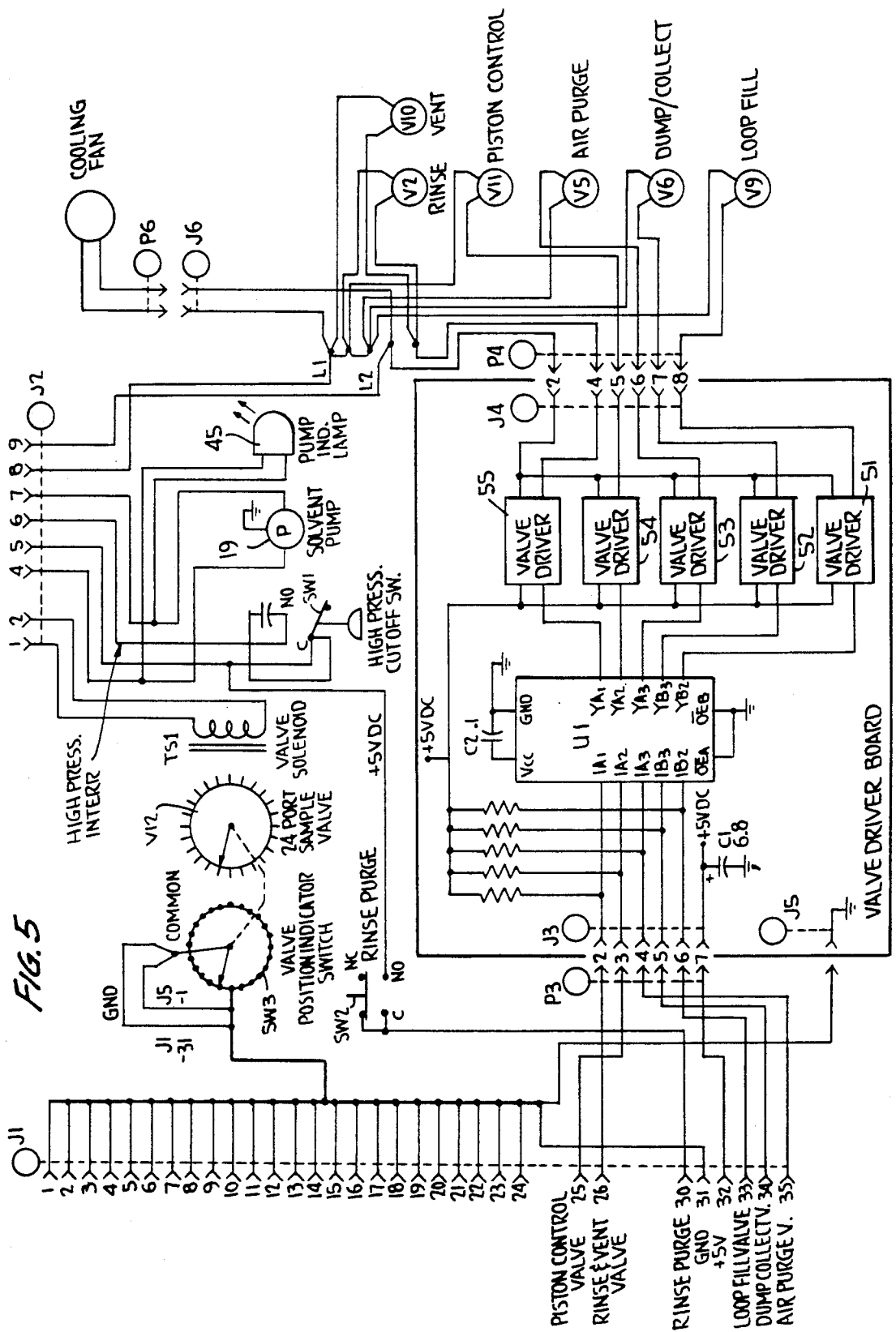
FIG. 5 is an electrical schematic diagram of the chromatography module portion of the system of FIG. 1.

FIG. 2 is an electrical block diagram of the chromatography system and is illustrative of the major electrical components in the system. In particular, FIG. 2 shows an electronic control board, an interconnect board, a chromatographic module and a controller. A detailed schematic diagram of the electronic control board is provided in FIG. 3. A detailed schematic diagram of the interconnect board is illustrated in FIG. 4. A detailed schematic diagram of the chromatographic module is illustrated in FIG. 5. Portions of the controller are illustrated in each of FIGS. 3, 4 and 5, as well as in FIG. 2 which illustrates how the primary power is employed to derive the various voltages utilized in the other electronic components. In particular, primary power, typically 115 VAC, is filtered in a filter unit 31 and applied across a varistor 32. One of the power lines is connected through a fuse 33 to a normally open contact of pole 34a of a three-pole two-position power switch. The other filtered power line, taken from the opposite side of varistor 32, is passed through the normally open contact of a second pole 34b of the power switch. The two power lines are passed from their respective power switch poles to a power supply unit 35 where the primary power is utilized to derive the various voltages required by the system. One output voltage is 6.2 VDC utilized at the interconnect board in the power failure and battery back-up circuit. Specifically, the 6.2 VDC line is employed to charge the back-up batteries and to provide a +5 VDC voltage to the electronics control board and the chromatographic module. Another voltage provided by power supply 35 is derived from the secondary winding of a step-down transformer and is utilized at the interconnect board to derive the power failure signal.

A back-up battery 36 provides 5 VDC through pole 34c of the power switch to the interconnect board for use in the event of a power failure.

Apart from schematically illustrating the power supply components, FIG. 2 serves primarily to illustrate the various interconnections between the circuit boards. In this regard, multi-pin jacks J1 and J2 at the chromatographic module engage respective plugs P1 and P2 that terminate respective cables running from the interconnect board. These cables terminate at the interconnect board in respective plugs P7 and P8 that, in turn, engage jacks J7 and J8 at the interconnect board. Multi-pin jacks J103, J104 and J105 at the electronic control board engage respective plugs P103, P104 and P105 that terminate respective cables leading to the interconnect board. The other end of those cables are terminated by plugs P9, P10 and P12 which correspondingly engage jacks J9, J10 and J12 at the interconnect board. A cable between the interconnect board and the controller terminates at plug P11 which engages jack J11 at the interconnect board.

Figure 3A:
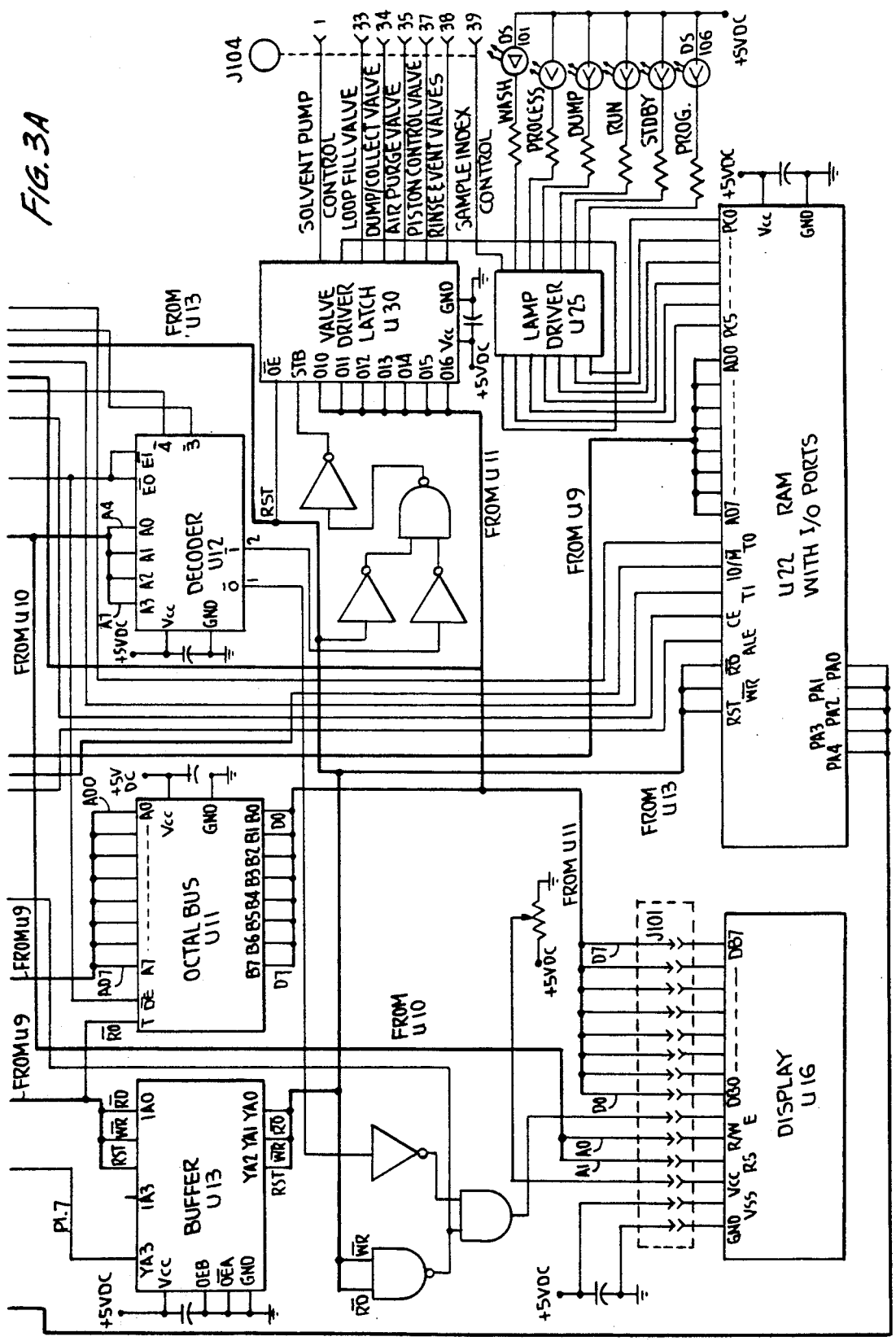
FIGS. 3 and 3B are an electrical schematic diagram of the control electronics portion of the system of FIG. 1.
Figure 3B:
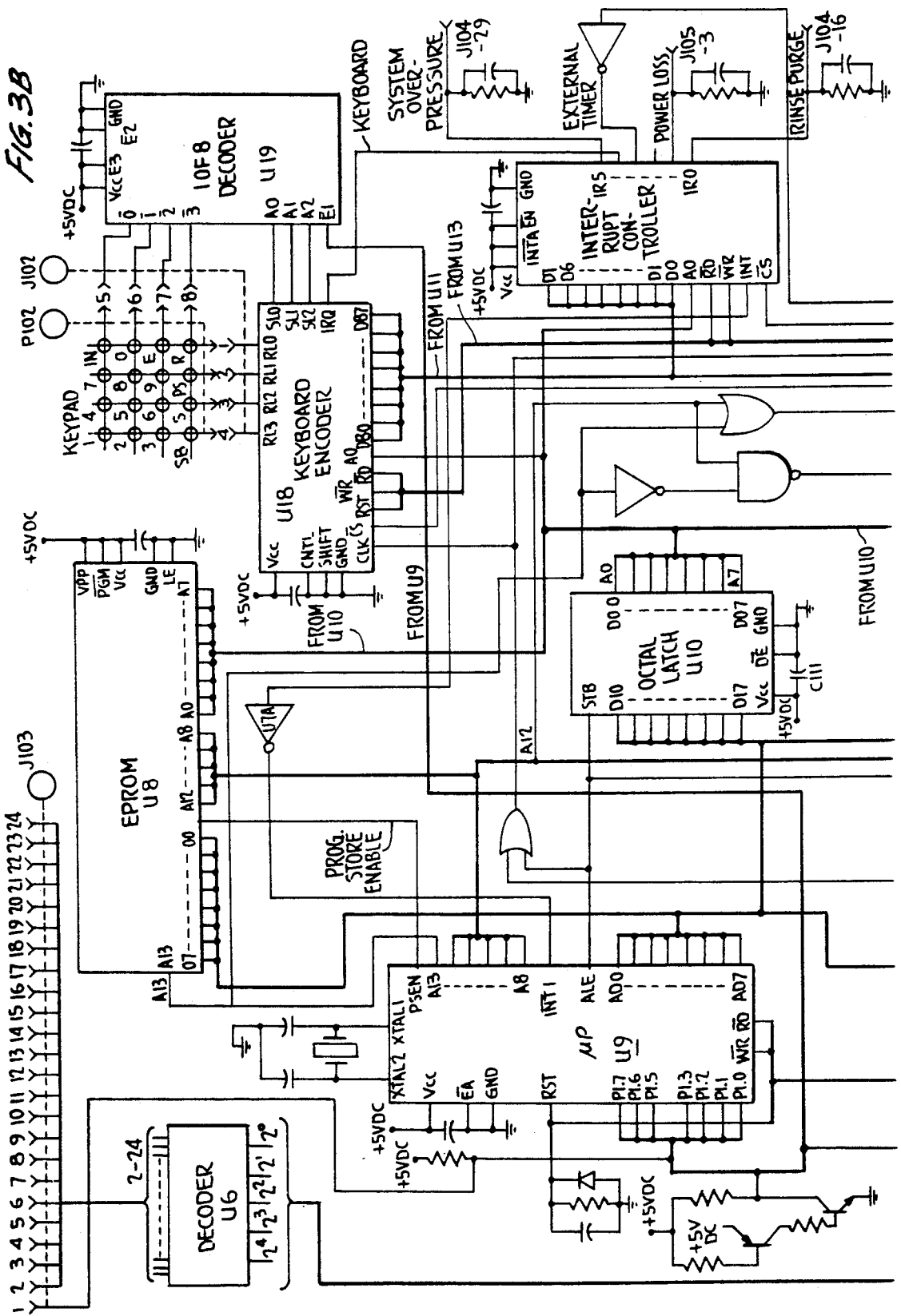

Referring now to FIGS. 3A and 3B of the accompanying drawings, the schematic diagram of the electronics control board should be considered with the bottom edge of FIG. 3B placed immediately adjacent the top edge of FIG. 3A. The electronic control board includes a microprocessor U9 which, in the preferred embodiment is a model 8031 (Intel) single-chip microprocessor including a central processing unit, two hundred fiftysix bytes of random access memory with one hundred twenty-eight eight-bit special function registers, four programmable input/output ports of eight lines each, two sixteen-bit timer/event counters, a serial I/O port, five interrupt input terminals, four banks of registers with eight registers per bank, and internal oscillator and timing circuitry. The microprocessor can address up to 64K bytes of external program memory (when its EA terminal is tied low) in addition to 64K bytes of external data memory. Read (RD), write (WR) and reset (RST) signals derived at the microprocessor are distributed to other units via a buffer U13. The microprocessor is programmed in the manner described subsequently herein to effect the automatic loading and run operations described above in relation to FIG. 1.

An EPROM U8 serves as a program memory for microprocessor U9 and, in the preferred embodiment of the present invention, is a model 2764 (Intel) ultra-violet erasable and electronically programmable read-only memory. When accessing external memory, microprocessor U9 provides the upper byte of the memory address from output terminals A8 through A13 and the lower byte and data model 8282 (Intel) latch, demultiplexes the low order address/data and supplies the low order address bits via a common bus to EPROM U8. The high order address lines are connected directly between microprocessor U9 and EPROM U8. The address latch enable (ALE) output signal from microprocessor U9 is employed to latch the low order address lines at octal latch U10. The program strobe enable (PSEN) output signal from microprocessor U9 enables the EPROM output signals A0 through A7 so that they may be read by the microprocessor.

A random access memory (RAM) with I/O port U22 is preferably a model 8155 (Intel) and is a 2048-bit static RAM organized as 256×8 bits with I/O ports and a 14-bit binary counter/timer. The I/O ports consist of two eight-bit programmable I/O ports and a programmable six-bit I/O port. For port A, terminals PA0 through PA4 are programmed as inputs to read the current sample position at the twenty-four port valve V12. Ports PC0 through PC5 are programmed as output terminals for controlling the Program (DS106), Standby (DS105), Run (DS104), Dump (DS103), Process (DS102) and Wash (DS101) status LED's, respectively, via lamp driver U25.

The octal bus U11 is typically a model 8286 (Intel) octal bus transceiver and is utilized to interface the microprocessor local bus to the system bus. The octal bus transceiver U11 can provide data from the processor to the system (bits A0 through A7 to B0 through B7) or from the system bus to the microprocessor (bits B0 through B7 to A0 through A7). The direction of the data flow is controlled by the microprocessor read line (RD). The transceiver lines are tri-stated (i.e., a high impedance state) when the transceiver is not enabled.

The octal latch U10, as described above, is employed to demultiplex the address and data from microprocessor terminals AD0 through AD7. The lower address byte (A0 through A7) is latched by the address latch enable (ALE) signal from the microprocessor. This latched address is employed by EPROM U8 and is also utilized along with a decoder to enable peripheral chips as required.

A keyboard encoder U18 is typically a model 8279 (Intel) programmable keyboard/display encoder and interfaces the microprocessor to the keyboard. The Keyboard is scanned via a one-of-eight U19. Keyboard encoder U18 return lines are connected to the scan lines when a key is depressed. Keyboard entries are debounced and strobed into an eight-character deep, first-in-first-out (FIFO) buffer. Individual key entries set the interrupt output signal (IRQ) applied to the interrupt controller U20 which, in turn, generates an interrupt signal for use at the microprocessor U9. The keyboard encoder U18 is programmed by the microprocessor to operate in scanned mode with a two-key lockout.

A display unit U16 is a one-line by forty character liquid crystal display. The display is interfaced to the microprocessor by the system bus.

The interrupt controller U20 is typically a model 8259 interrupt controller (Intel) and handles interrupts from five different sources. These interrupts are: rinse purge, power loss, external timer, keyboard and system overpressure which are connected to terminals IR0, IR1, IR3, IR4 and IR5, respectively of the interrupt controller. The interrupt controller is programmed by microprocessor U9 to operate in a polled mode. When one of the input signals to the interrupt controller changes from a low level to a high level, the interrupt controller generates an interrupt request that is applied to the microprocessor. The microprocessor responds by reading a status word from the interrupt controller to indicate which of the interrupt input signals has caused the interrupt request. Upon reading the source of the interrupt request, the microprocessor then takes appropriate action to service that interrupt.

A valve driver latch U30 is typically a model 8282 (Intel) valve driver latch and provides the control signals to actuate the rinse valve V2, vent valve V10, piston control valve V11, purge valve V5, dump/collect valve V6 and loop fill valve V9. Latch U30 also provides control signals for the controller interconnect board circuitry to actuate the solvent pump 19 and the twenty-four port sample select valve V12, the latter being effected in response to control signals from the micro-processor decoded at a decoder unit U12.

Referring now to FIG. 4 of the accompanying drawings, the interconnect board provides connections between the electronics control board, the power supply and the chromatography module. When input power is lost, the power failure and battery back-up circuit 41 provides a "power fail" signal to the electronics control board where it is received as a "power loss" signal at the interrupt controller U20. The +5 VDC (battery) line is also provided at the control board through the power failure and battery back-up circuit 41. Circuit 41 also includes a trickle charge circuit for continuously charging the back-up battery in the absence of a power failure.

A solvent pump drive circuit 42 responds to the solvent pump control signal from the electronics control board to provide power to the solvent pump 19.

A 24-port valve drive circuit 43 utilizes the ac line voltage to provide a full-wave rectified and regulated voltage to drive the sample select valve V7 via its drive solenoid TS1. When a control pulse is received on the sample index control line, circuit 43 responds by providing the regulated voltage across solenoid TS1 to stop the valve wafers V12A, V12B and V12C.

Referring to the schematic diagram of the chromatography module in FIG. 5, the solenoid TS1 for the 24-port sample valve V12 is actuated under control of the microprocessor U9 (FIG. 3B) by drive circuit 43 (FIG. 4). Specifically, drive circuit 43, in response to a control pulse applied thereto, provides a signal that results in a stepping pulse applied across solenoid TS1, thereby switching valve V12 to its next sequential position. A twenty-four position switch SW3 is actuated along with valve V12 to assume a position corresponding to the valve position. Switch SW3 includes a common grounded contact connected to one of twenty-four lines that are, in turn, connected to the twenty-four selectable switch contacts, respectively. For simplicity of illustration, only one contact is shown connected to a corresponding pin of connector jack J1, but it will be appreciated that each switch contact is connected to a respective jack pin. Accordingly, only one of the twenty-four pins is grounded at any time, that pin corresponding to the sample container 13 (FIG. 1) currently be accessed by valve V12. These pins are connected via plug P1 and the readout cable (FIG. 2), plus P7, jack J7, the interconnect board, jack J9 and plug P9 (FIG. 4) to the electronics control board wherein the switch position number is decoded by a decoder U6 (FIG. 3A) into a plural-bit binary number that is read by the microprocessor U9 via RAM with I/O ports U22 (FIG. 3B).

The high pressure cut-off switch SW1 is the electrical switch corresponding to over-pressure sensor P2 (FIG. 1) and is automatically closed when the pressure in the line between sample solvent pump 19 and port B of the sample select valve V7 exceeds a pre-established maximum value. Upon closure of switch SW1, +5 VDC appearing at its common terminal is applied to its normally open terminal to become the high pressure interrupt signal transmitted to the interrupt controller U20 (FIG. 3B) via jack J2, plug P2, plug P8, jack J8, the interconnect board (FIG. 4), jack J10, plug P10, plug P104 and jack J104.

Sample solvent pump 19 is actuated by the sample pump drive circuit 42 (FIG. 4) under the control of the sample pump control signal provided by the system microprocessor U9 (FIG. 3B) via valve drive latch U30. A pump indicator lamp 45 is electrically connected in parallel with the pump motor and is energized whenever the pump is operating.

Rinse purge switch SW1 has +5 VDC connected to its normally opened contact. When the switch is closed, typically during servicing of the equipment, a rinse purge signal is provided at the common contact of the switch and applied as an interrupt signal to the interrupt controller U20 (FIG. 3B). The rinsing process can thereby be initiated manually.

The solenoid actuation signal for loop fill valve V9, dump/collect valve V6, air purge valve V5, piston control valve V11 and the rinse and vent valves V2 and V10 are applied from the valve driver latch U30 (FIG. 3A) to individual signal buffers U1. The buffers, in turn, drive individual valve drivers 51, 52, 53, 54 and 55 which are solid state relays connected to drive the solenoids for the corresponding valves.

Referring now to FIGS. 6, 7 and 8, the chromatography unit includes a housing 60 at the top of which is located the sample solvent reservoir 15. Each of the sample storage containers 13 is suspended outwardly from housing 60 by a respective support arm 61 having a cover 62. It will be noted that covers 62 preclude viewing the support arms 61 in FIG. 6, and that the cover 62 is removed from the single support arm illustrated in FIG. 7. Each sample storage container 13 has its upper end externally threaded at 63 to permit it to be engaged by a closure member 64. Closure member 64 preferably has a cylindrical configuration and is made of a suitable plastic material. A closure member bore extends axially between the top and bottom surfaces of the closure member and includes a top section 65 and a threaded bottom section 66. Top bore section 65 is diametrically enlarged relative to bottom bore section 66 which is threaded so as to engage the threaded top portion 63 of container 13. An annular shoulder 67 faces upwardly and demarks the transition between bore sections 65 and 66. Two tapped holes 68 are defined in the top surface of closure member 64 to permit the closure member to be secured to the underside of support arm 61 by means of screws 69 extending through suitably provided mounting holes in support arm 61. When thusly mounted, the top surface of the closure member 64 is flush against the underside of support arm 61.

A closure insert 70 has a generally cylindrical periphery sized to be snugly received in top bore section 65 in closure member 64. When thusly secured, the top surface of closure insert 70 is flush with the top surface of closure member 64. More specifically, the axial length of insert 70 is substantially equal to the axial length of top bore section 65. Closure insert 70 also has an axial bore defined therethrough. The closure insert bore includes an upper threaded portion 71 of relatively small diameter, and a shorter lower portion of somewhat larger diameter. The two bore portions 71 and 72 meet at a downwardly facing annular shoulder 73. An O-ring 74 is disposed in lower insert bore portion 72 and is contained between annular shoulders 73 and 67 when insert member 70 is fully inserted into the upper section 65 of the closure bore.

Support arm 61 has an access hole 75 defined therein in substantial axial alignment with the closure and insert bores, thereby permitting pick-up tube 22 to be extended through access hole 75, insert 71 and closure member 64 into the sample storage container 13. Pick-up tube 22, which extends from the sample storage container interior to a respective accessible port at section V12A of the twenty-four port valve, also extends through a connector 80. The connector includes a bottom male fitting 81 threaded to be engaged by the threaded upper portion 71 of the insert bore. In this regard, fitting 81 projects through access hole 75 in support arm 61 into the insert member 70 in fluid sealing relation. The fluid seal may be enhanced by wrapping suitable sealing tape about the threaded portion of fitting 81 before engaging the fitting in threaded bore section 71. The interior of connector 80 is hollow and diametrically larger than pick-up tube 22 so that an annular space 82 surrounds tube 22 and communicates with the top of container 13 via the bores in insert 70 and closure member 64.

Delivery tube 23, described above as alternatively supplying purge gas and rinse fluid to the sample storage containers 13, extends radially into annular space 82 through a side fitting 83 in which tube 23 is frictionally engaged. Side fitting 83 is externally threaded to be engaged in a locking sleeve 84 through which delivery tube 23 also extends. Sleeve 84 serves to engage fitting 83 in fluid sealing relation. A top fitting 85 of connector 80 receives pick-up tube 22 in frictional engagement and is externally threaded to be engaged by a locking sleeve 86 through which pick-up tube 22 also extends. Sleeve 86 engages top fitting 85 in fluid sealing relation.

It will be appreciated that delivery of purge gas into the annular space 82 in connector 80 via delivery tube 23 results in pressurization at the top of sample storage container 13. This pressurization by the purge gas is applied to the surface of the sample fluid in container 13 and forces fluid up through the pick-up tube to the appropriate accessible port at valve section V12A. The use of insert member 70 in connection with O-ring 74 at the upper end of the closure member bore has proven to be exceedingly effective in eliminating leakage of fluid under pressure from the juncture of the sample storage container 13 and closure member 64.

The support arm 61 is configured in the form of a channel adapted to receive the pick-up tube 22 and delivery tube 23 extending from connector 80 back into housing 60. Cover member 62 is configured to enclose both tubes 22 and 23 and connector 80 within the space defined by the channel-shaped support arm 61 and its cover 62.

Referring again to FIG. 3B of the accompanying drawings, the keypad for permitting manual entry of information into the system permits an operator to select the various operating modes and the sample load, dump, collect and wash time intervals. In addition, the number of samples to be processed and the program to be employed to process each sample may be selected from the keypad. The keypad includes individual keys for respective numerals 0 through 9 which may be used to enter various parameters including time intervals for the sample load, dump, collect and wash time programs; starting and ending samples; and the number of a particular program to be used for a given sample. The numerical keys may also be employed to respond to program prompts and to identify saved programs. The index key (IN) permits sequencing through display messages during service prompts and entry of program parameters. The enter key (E) permits entry of data into a temporary memory to change program values. These values may be "locked in" with the program save (PS) key. The enter key is also employed to start and stop a timer when measuring sample load times using the sample load auto-timing function.

The run key (R) permits an operator to start or restart sample processing. The status key (S) causes display of "run" parameters during sample processing and allows the operator to review multi-program sample group to program set-ups.

The program save (PS) key permits the saving of program parameters, that are altered with the enter key, in various program memory areas. The standby key (SB) permits interruption of sample processing or returns the display to the first prompt during service prompts and programming.

In FIG. 3A there are illustrated six lamps DS101 through DS106. The standby lamp DS105 is actuated when sample processing is terminated at the end of processing or during service prompts. The program lamp DS106 is actuated during programming prompts. The run lamp DS104 is energized, in addition to the dump process, collect or wash lamps, during sample processing. The dump lamp DS103 is energized during sample processing dump time. The wash lamp DS101 is energized during sample processing wash time. The process lamp DS102 is actuated during sample processing.

The system described above is operated under the control of a program stored in microprocessor U9 (FIG. 3B). A typical program for this purpose is represented by the flowchart illustrated in FIGS. 9A through 9II. The flowchart is sufficiently detailed to enable a full understanding of its operation without any accompanying discussion. However, various aspects of the software are described below in relation to the flowchart in order to amplify certain aspects of the present invention.

Figure 9C:
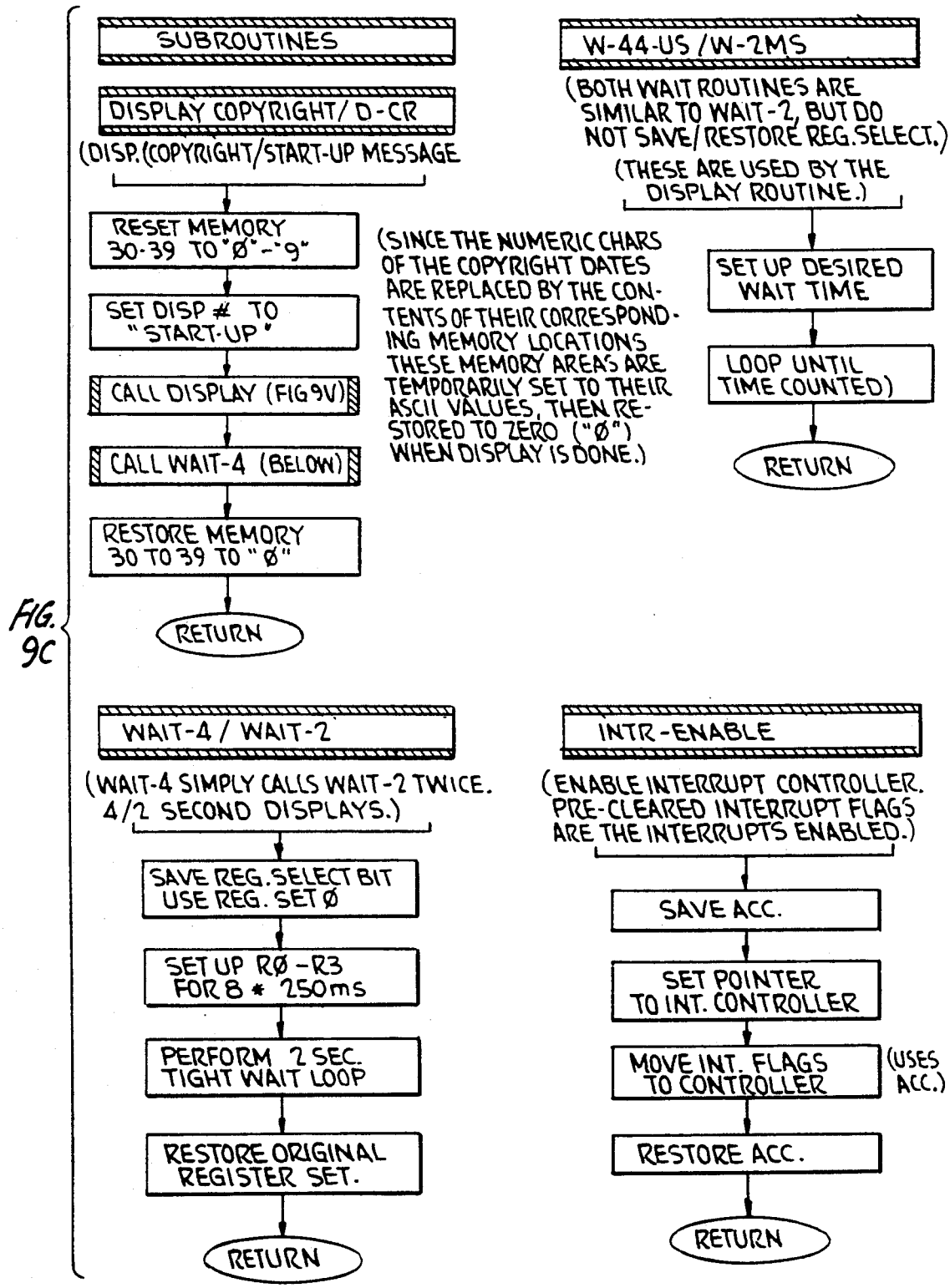
FIGS. 9 through 9II constitute a flow chart of the software employed to control the system of FIG. 1.
Figure 9D:
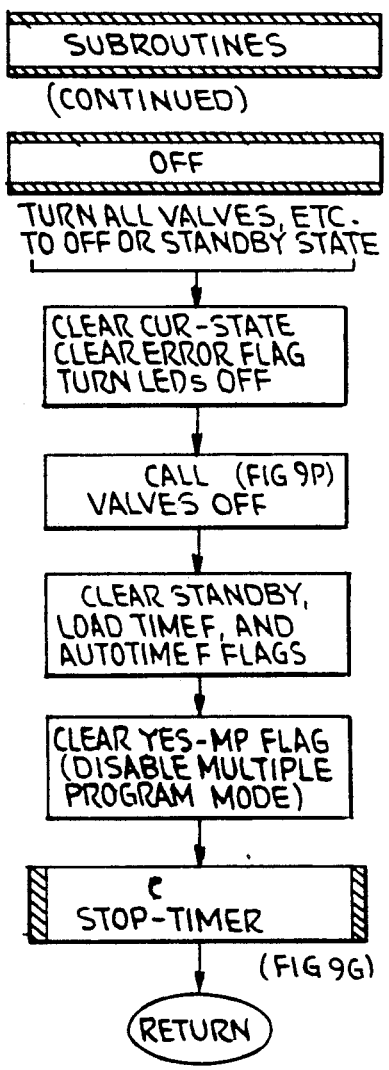
Figure 9I:
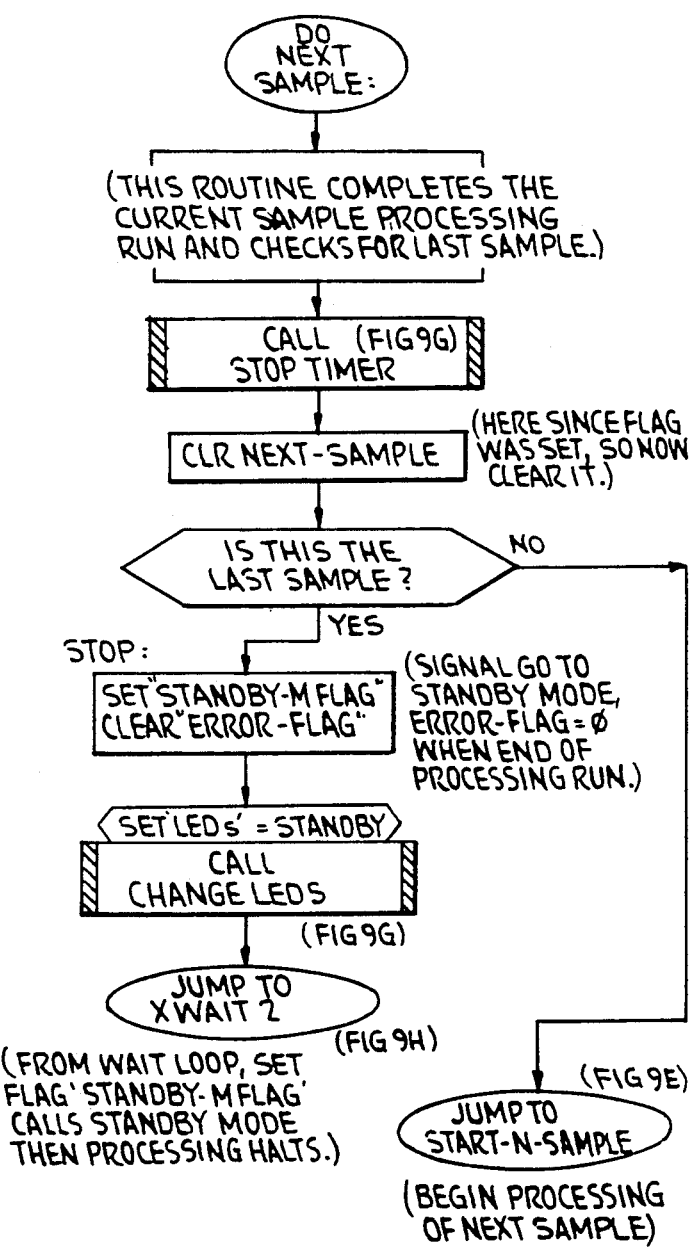
Figure 9F:
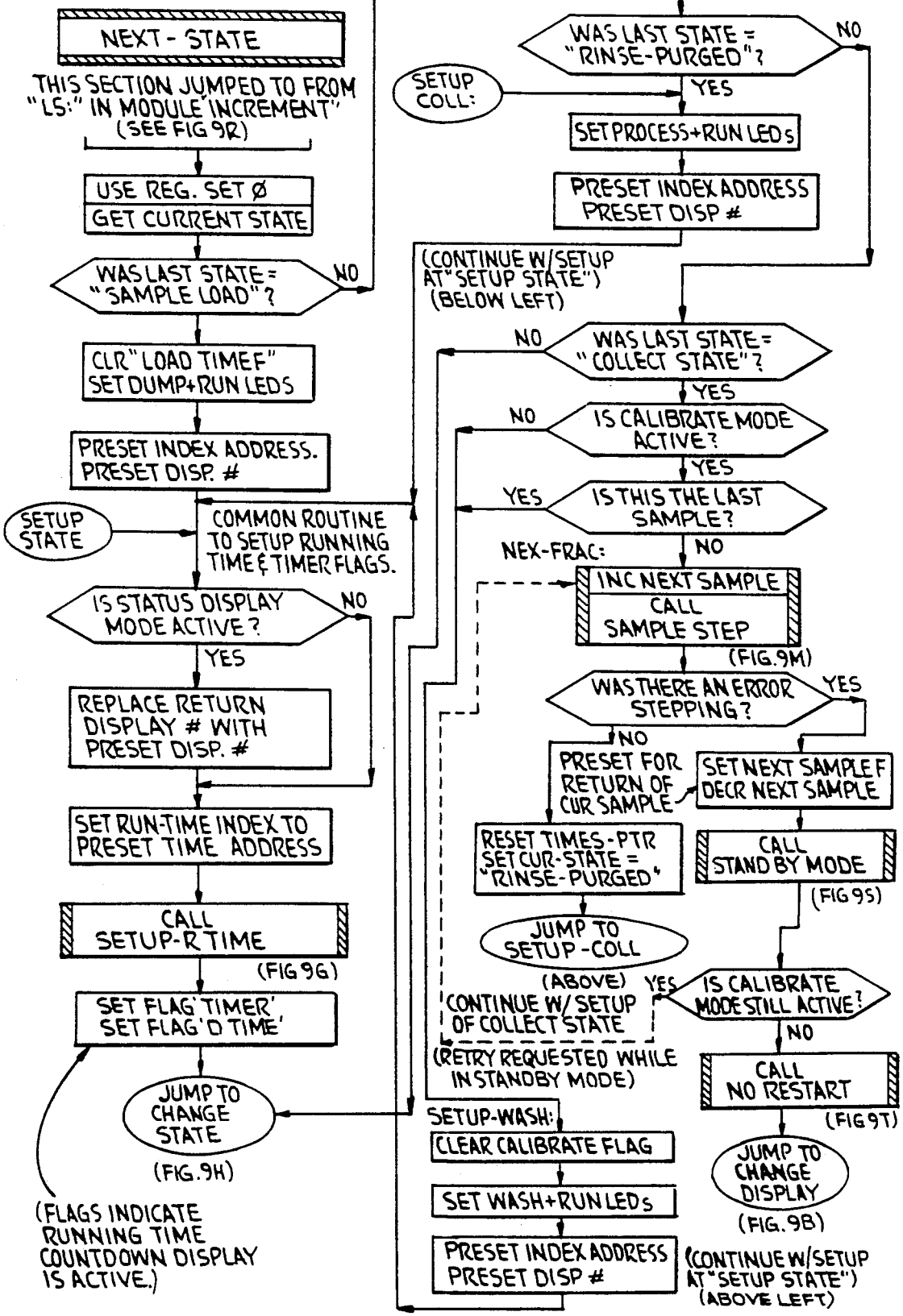
Figure 9G:
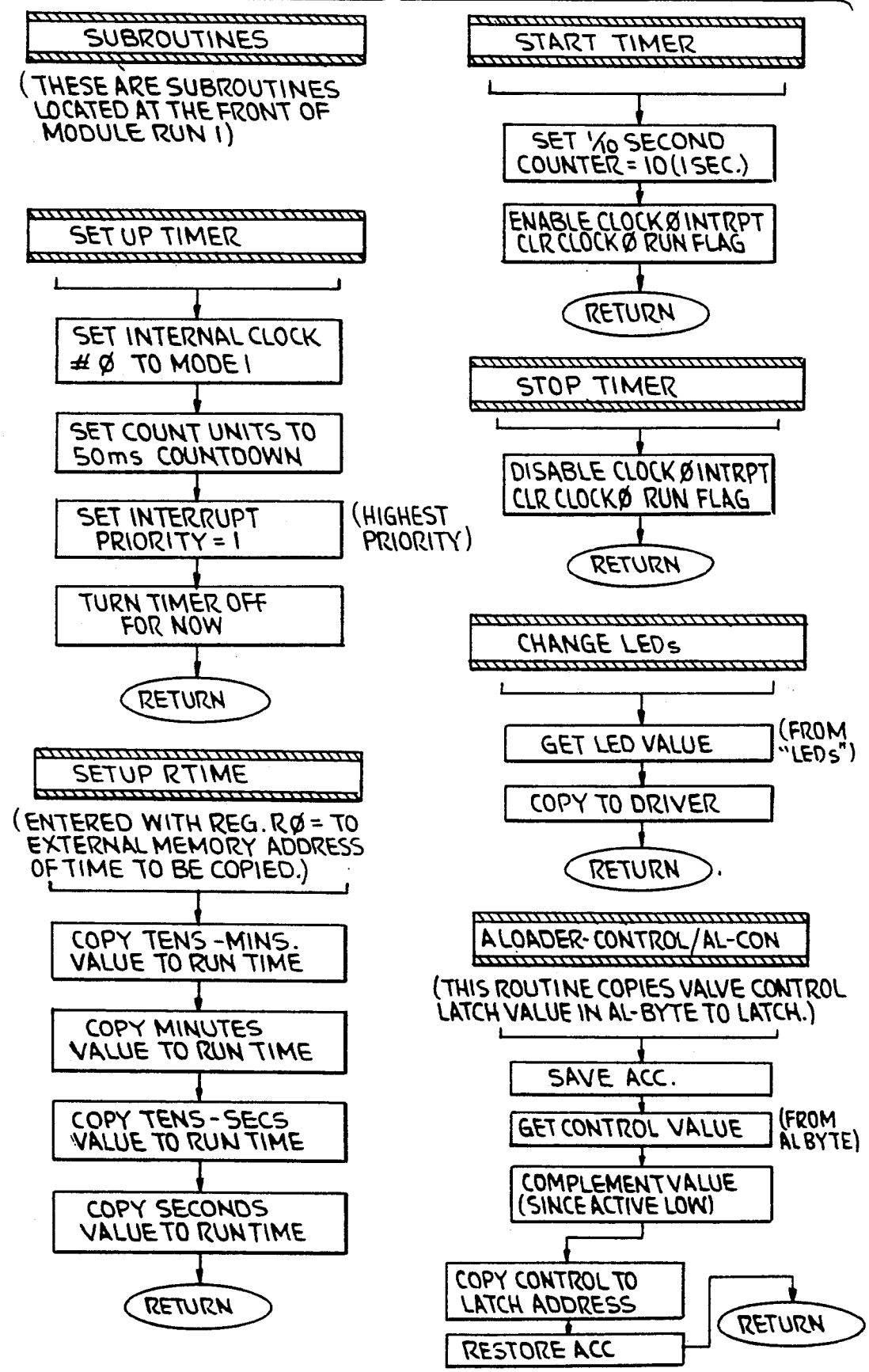
Figure 9J:
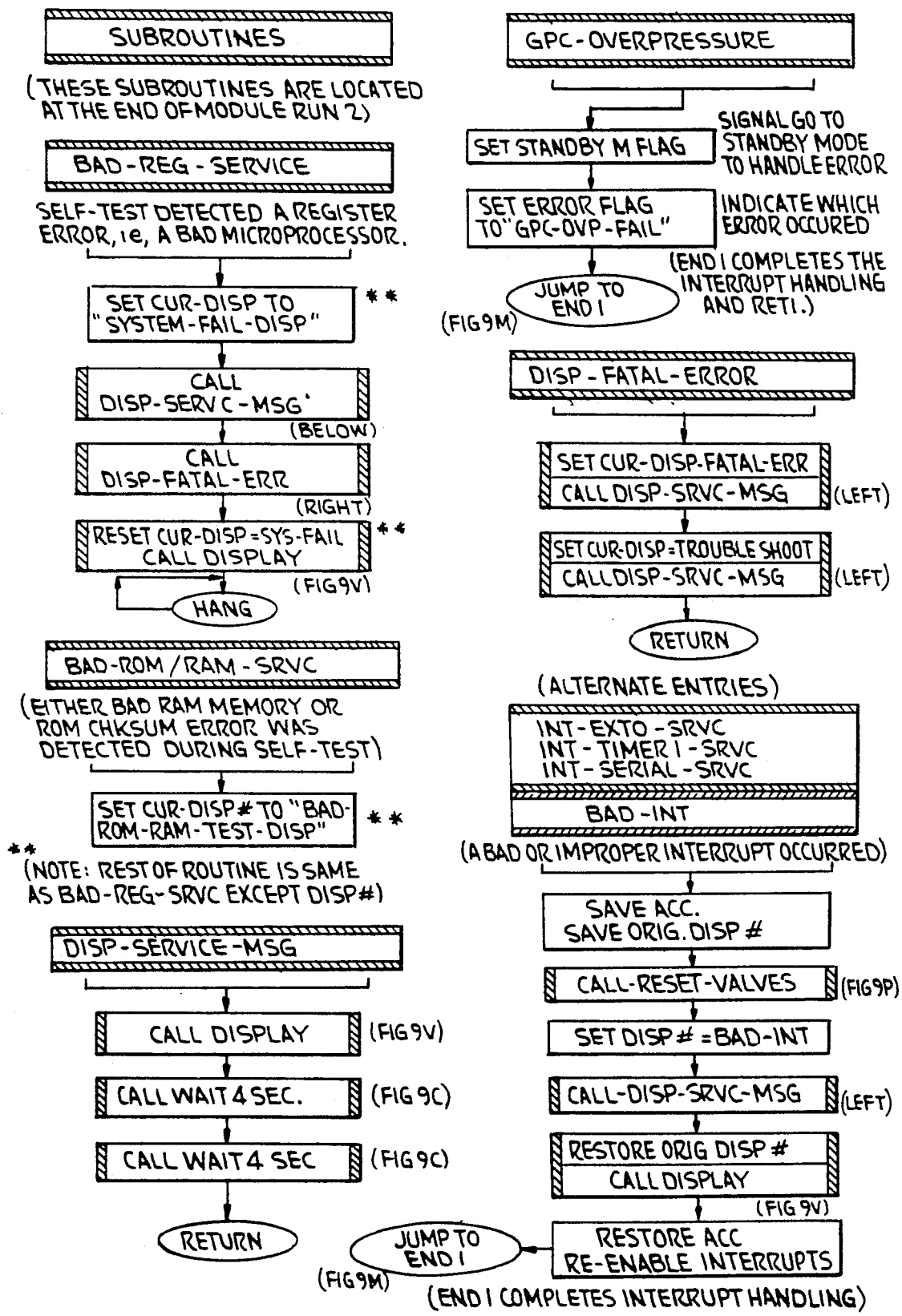
Figure 9L:
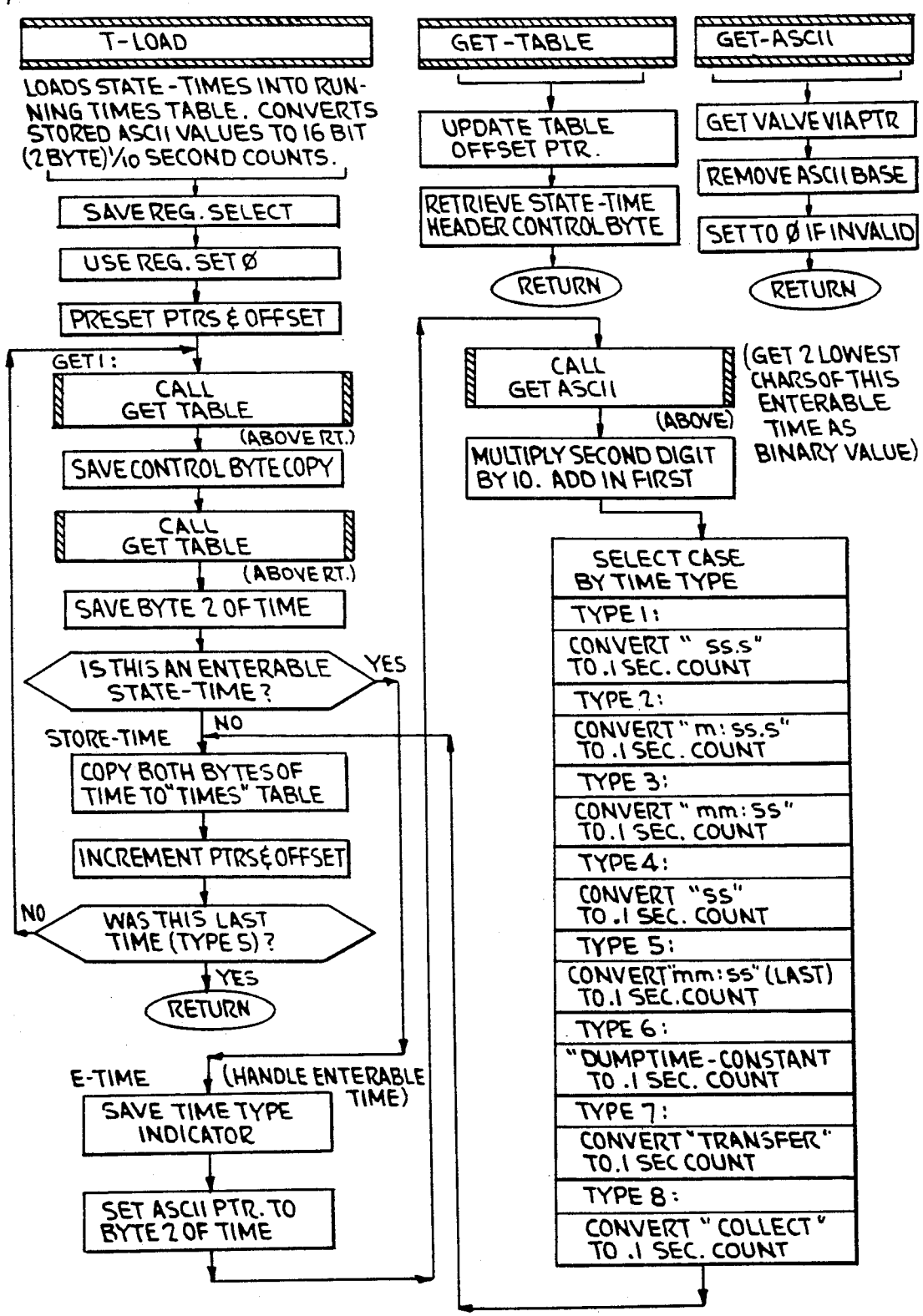
Figure 9M:
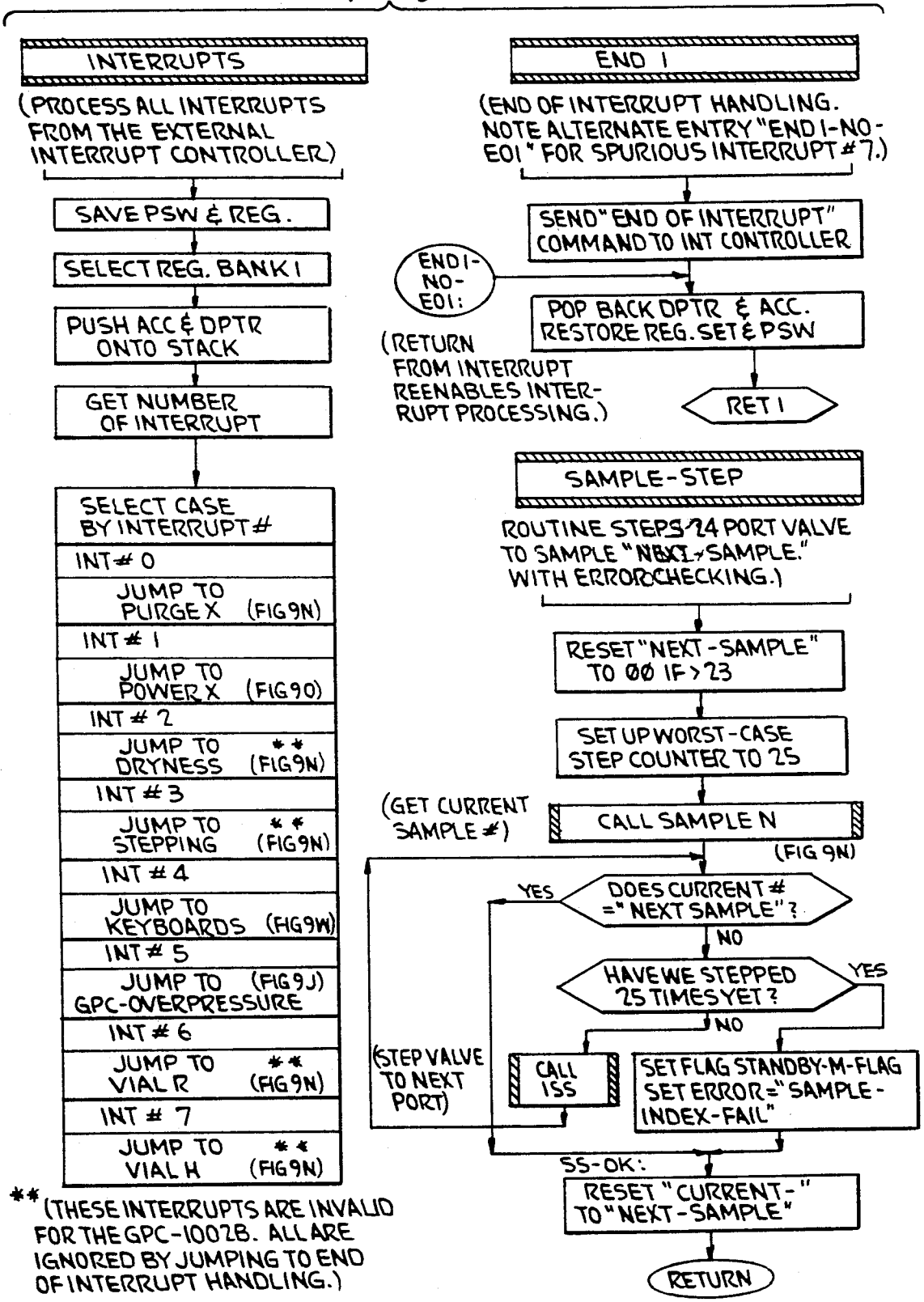
Figure 9N:
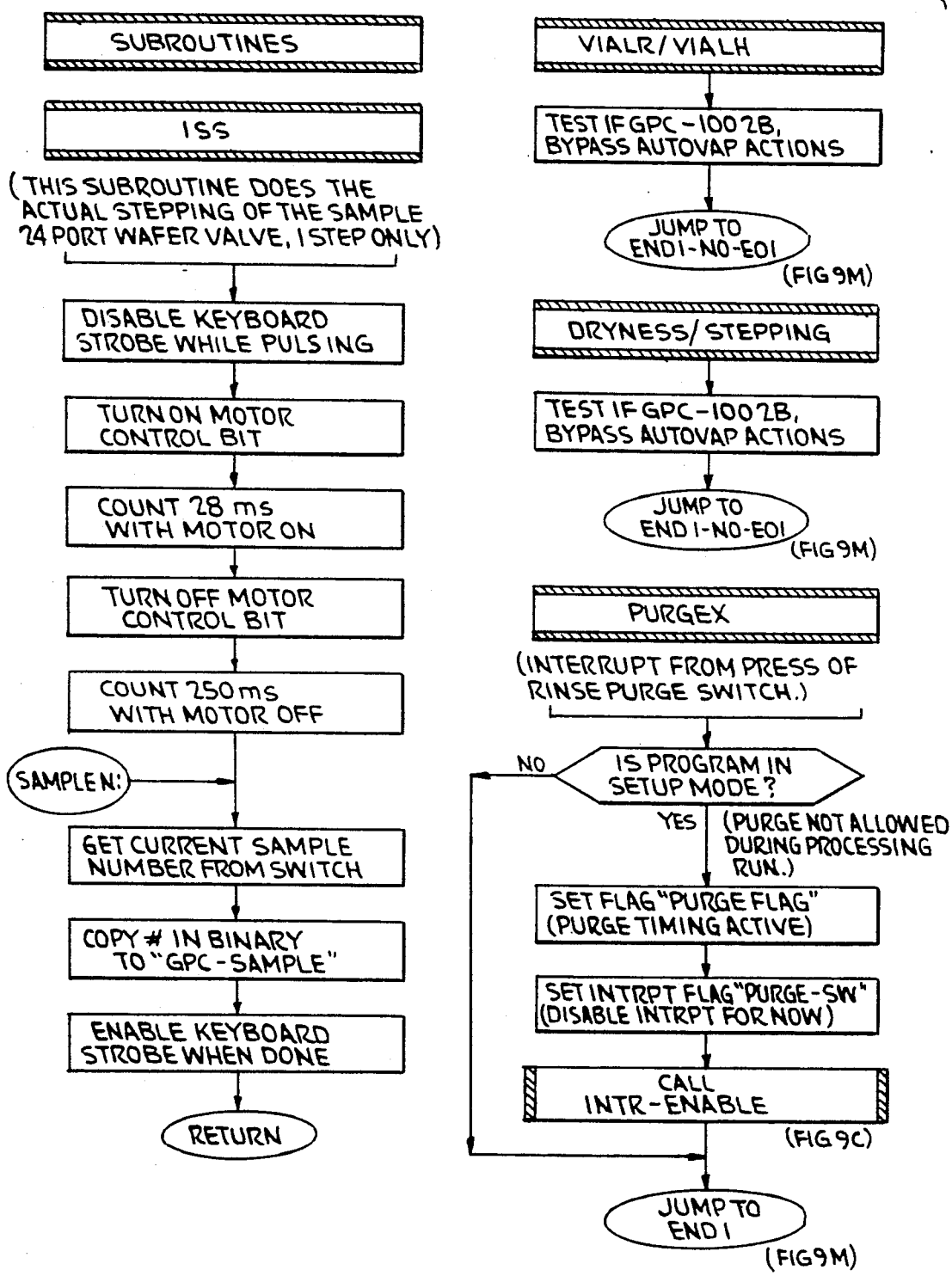
Figure 9Q:
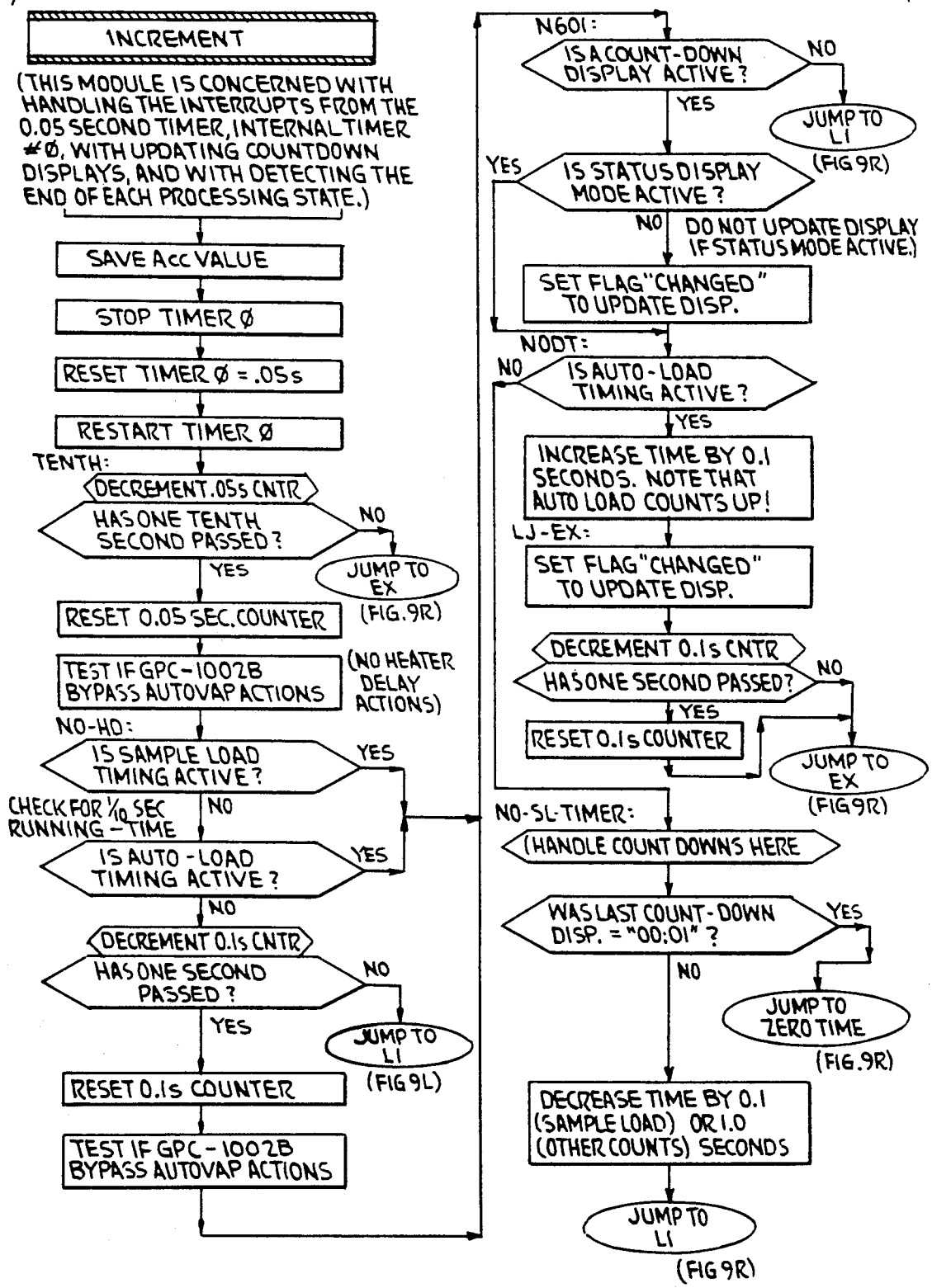
Figure 9R:
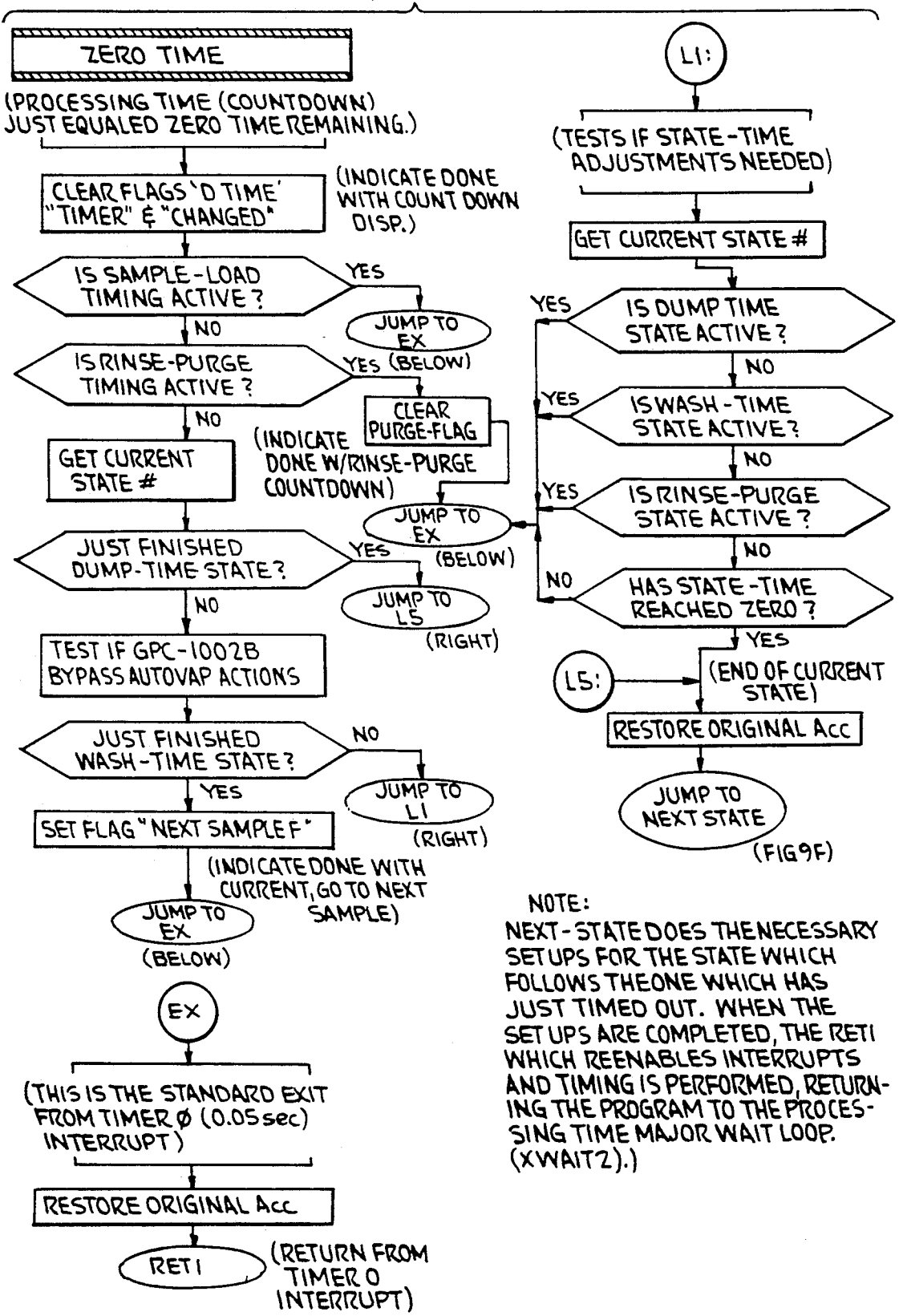
Figure 9S:
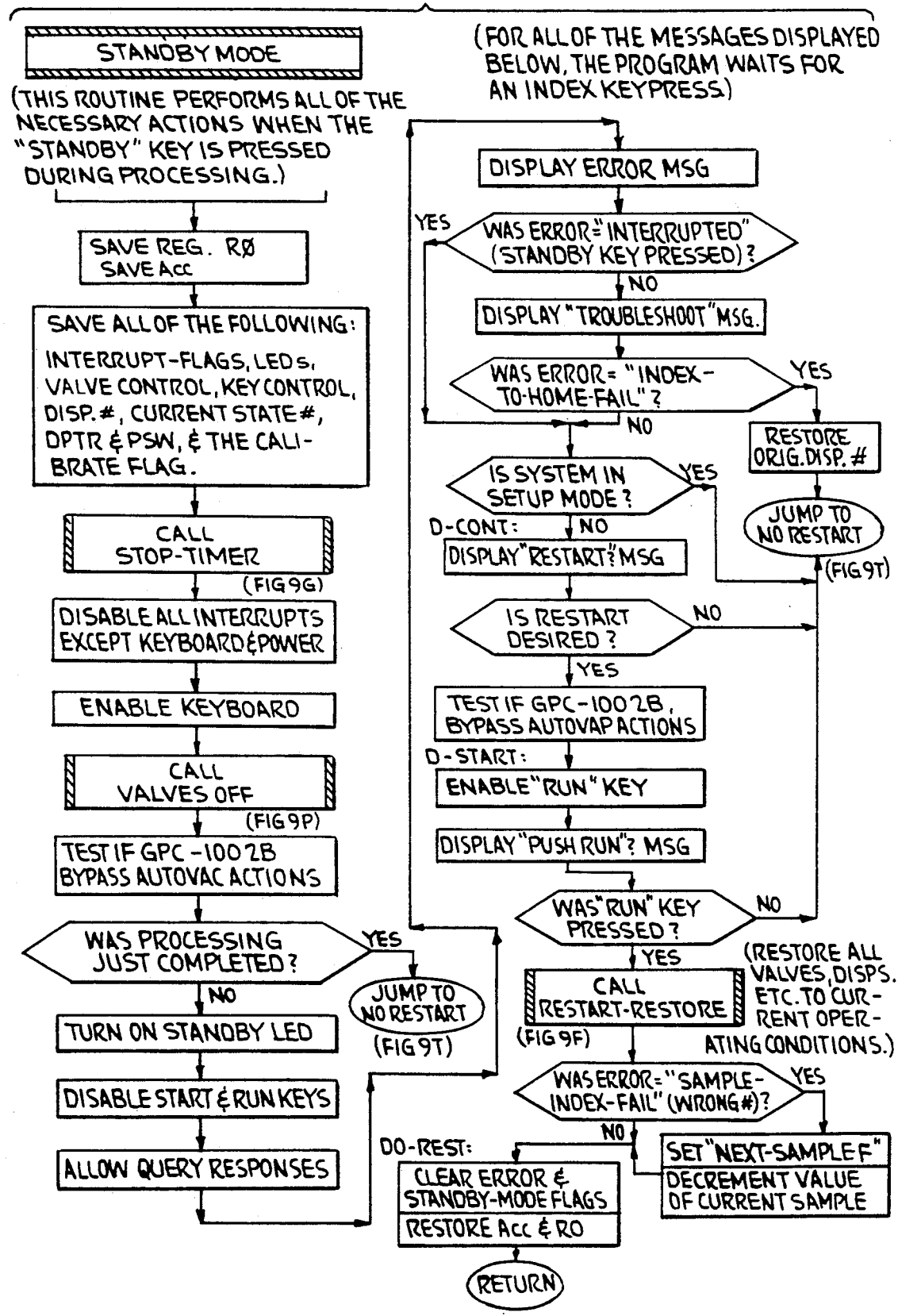
Figure 9T:
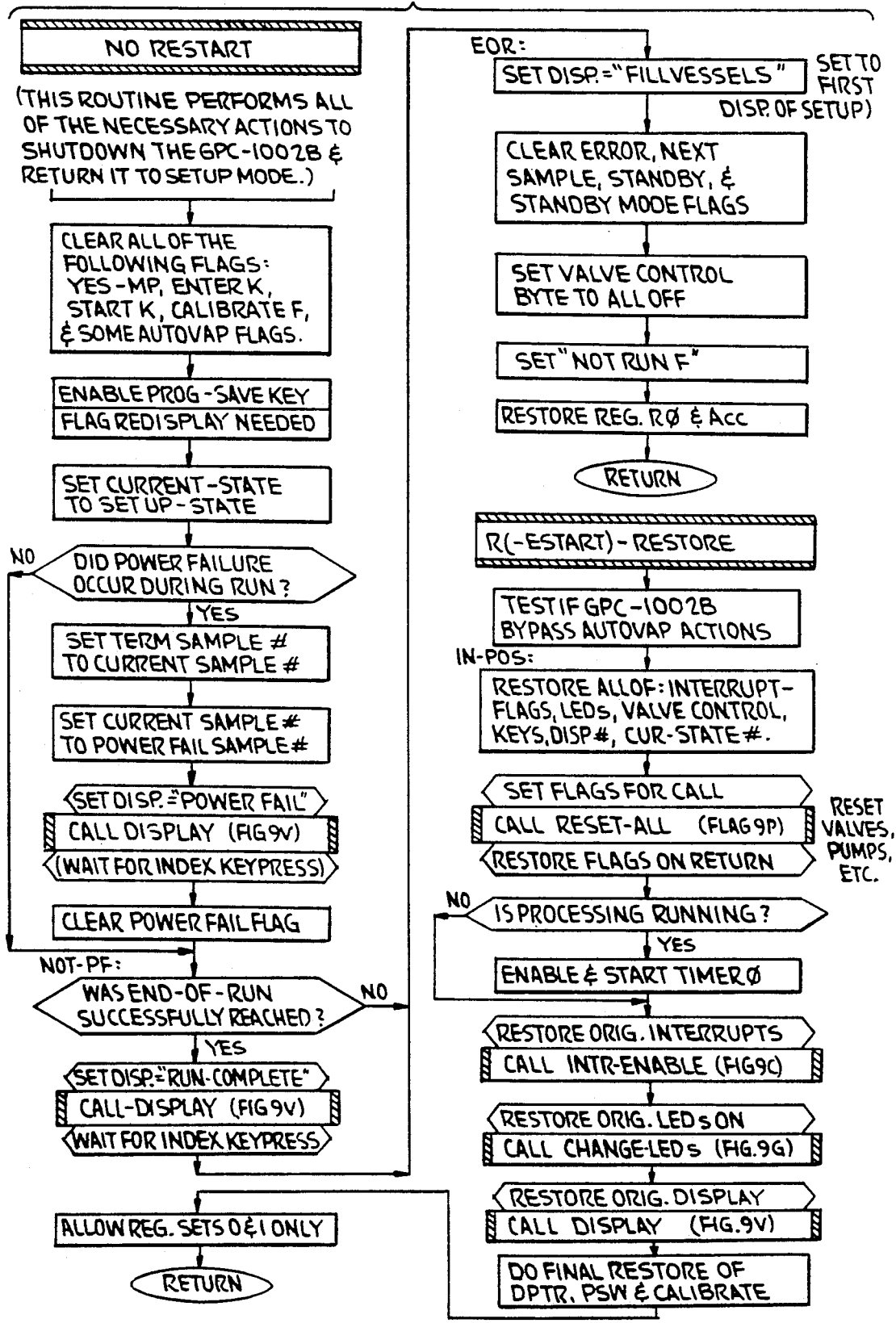
Figure 9U:
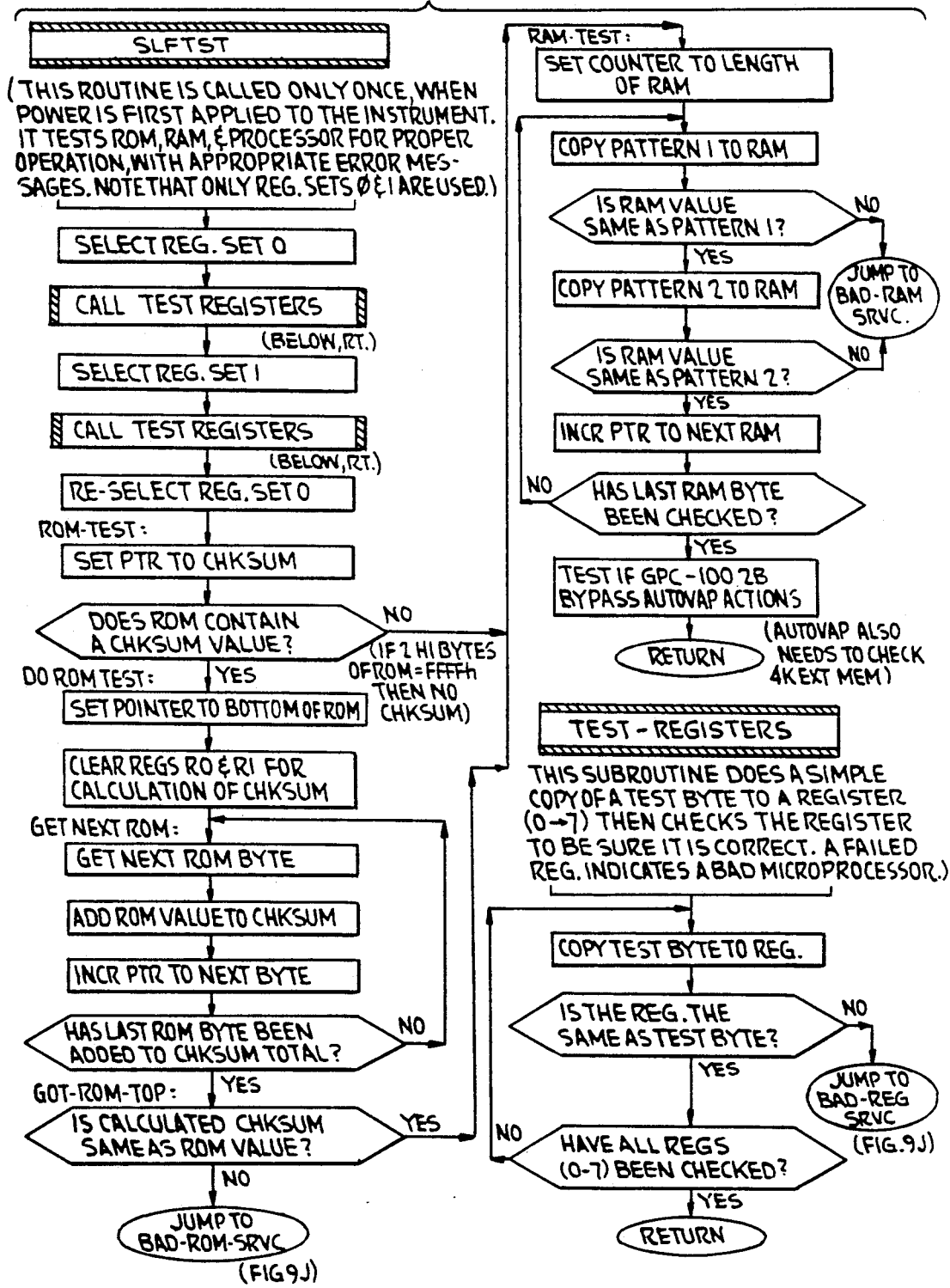
Figure 9W:
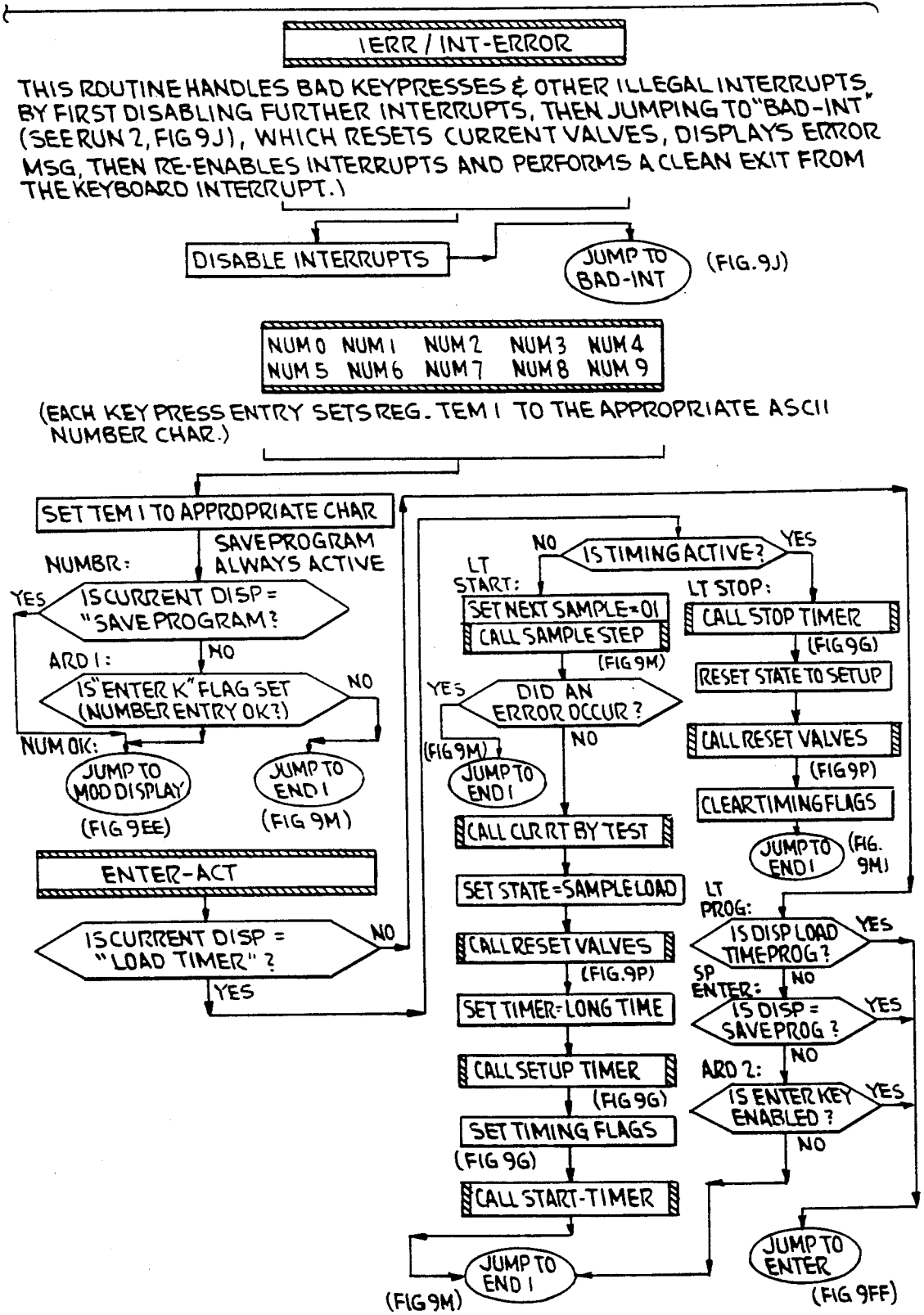
Figure 9X:
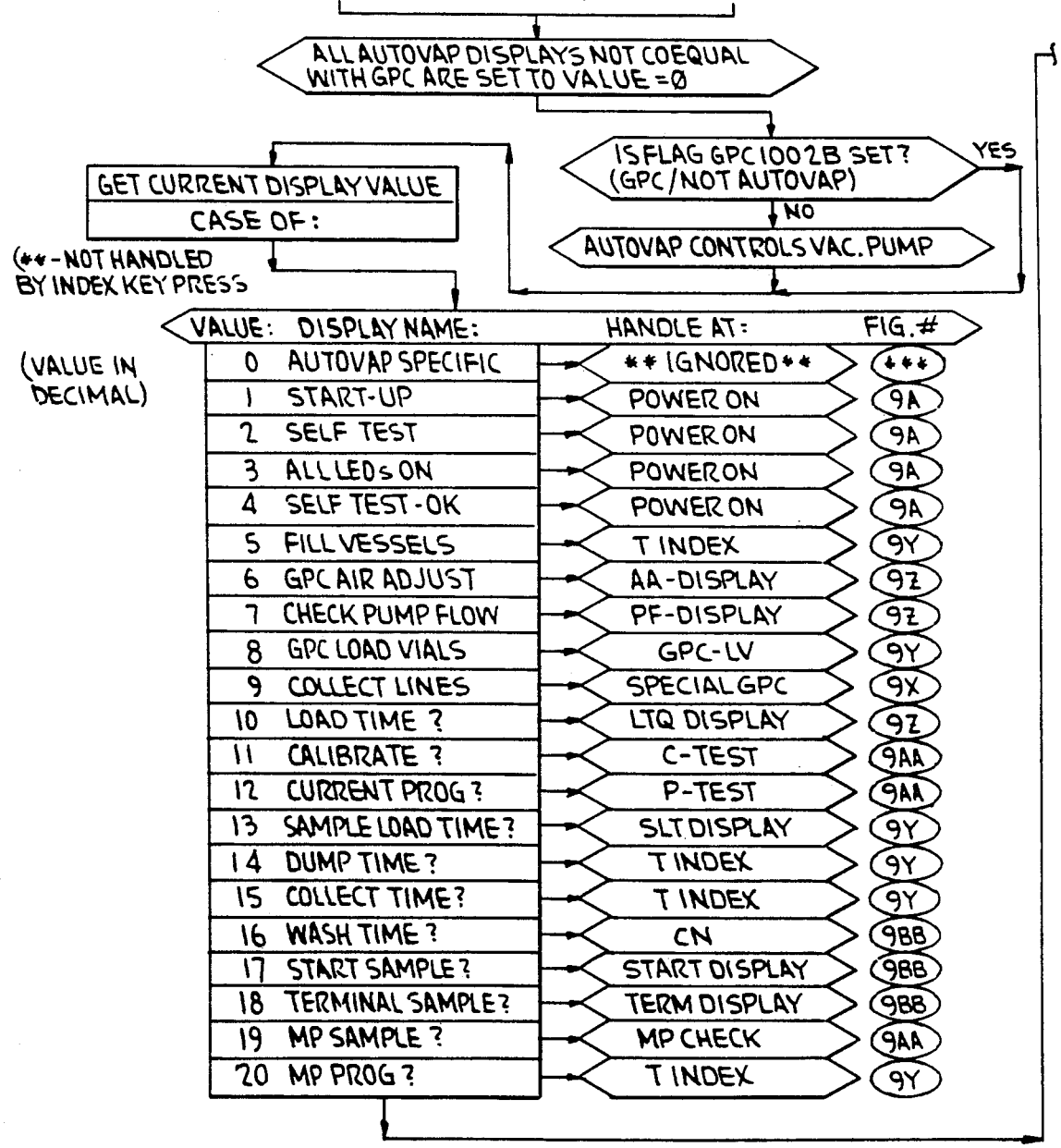
Figure 9Y:
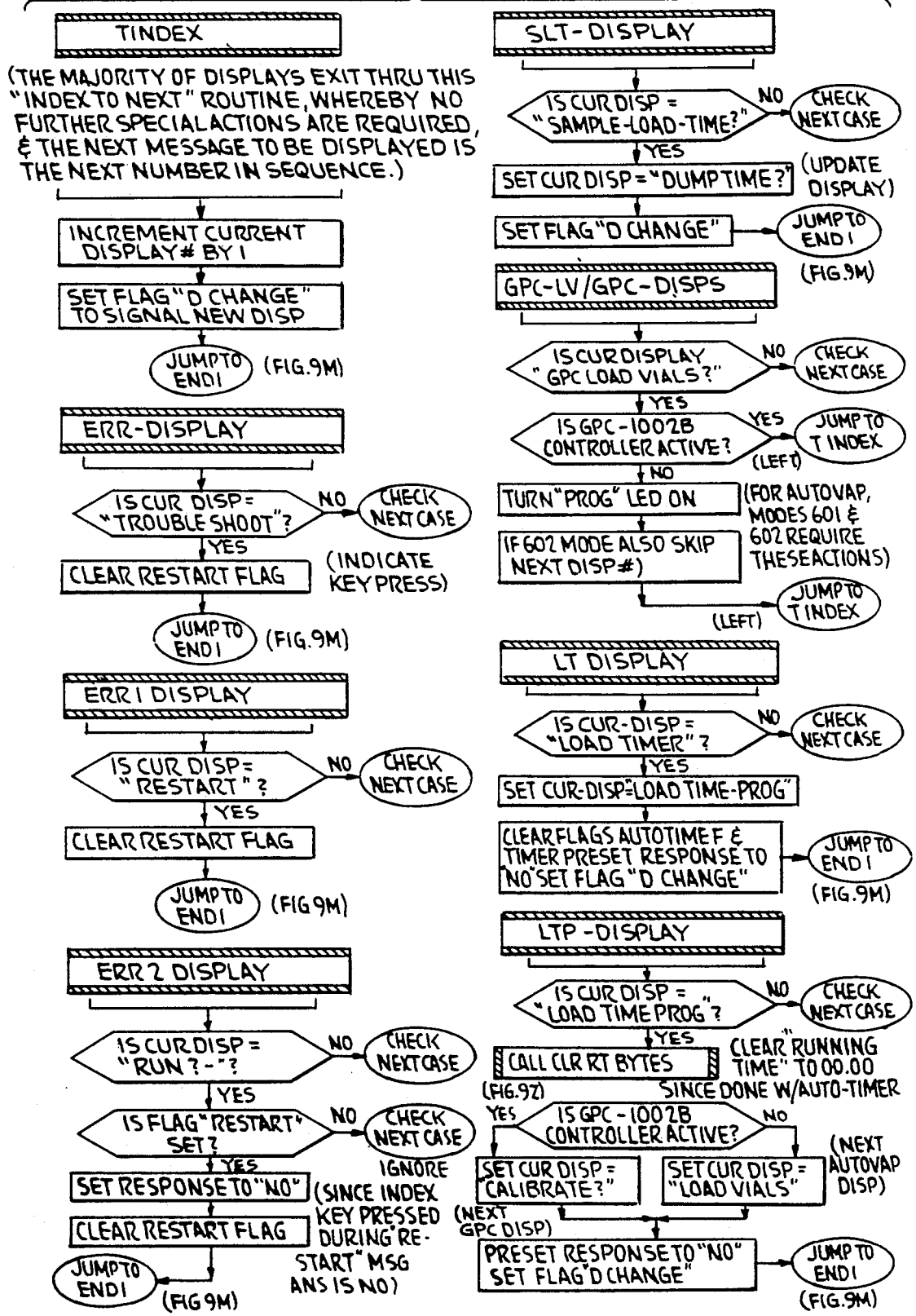
Figure 9Z:
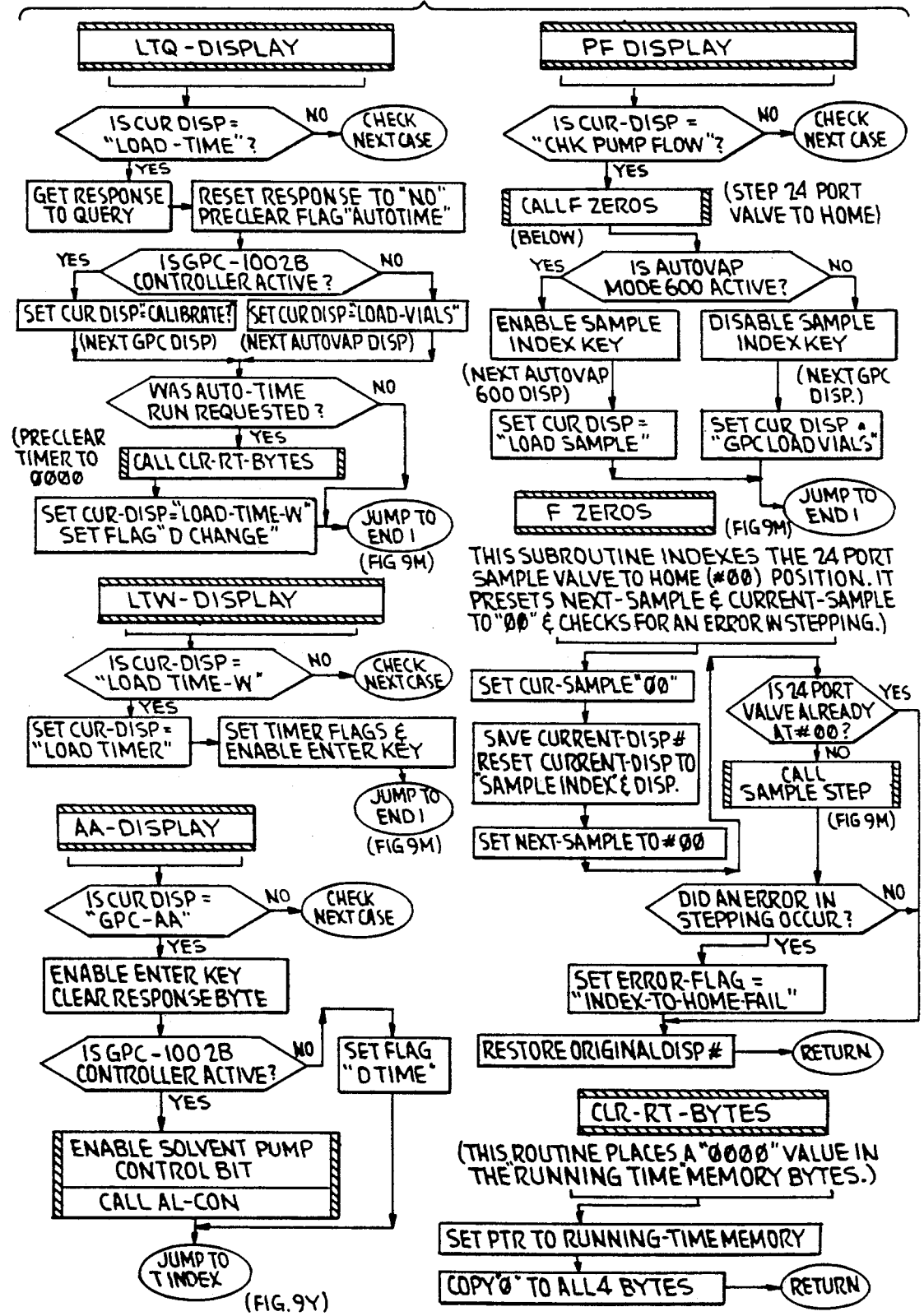
Figure 9A:
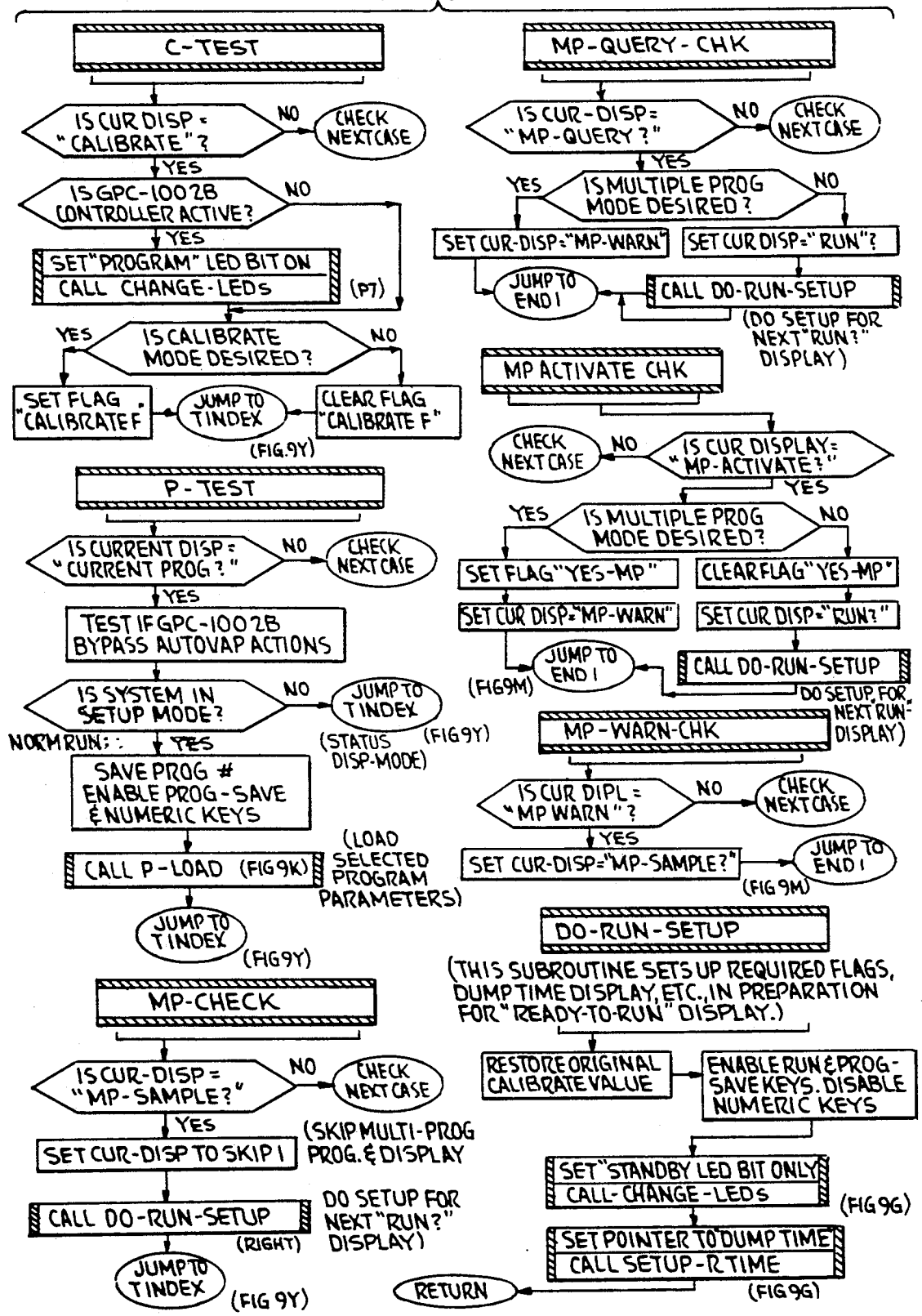
Figure 9B:
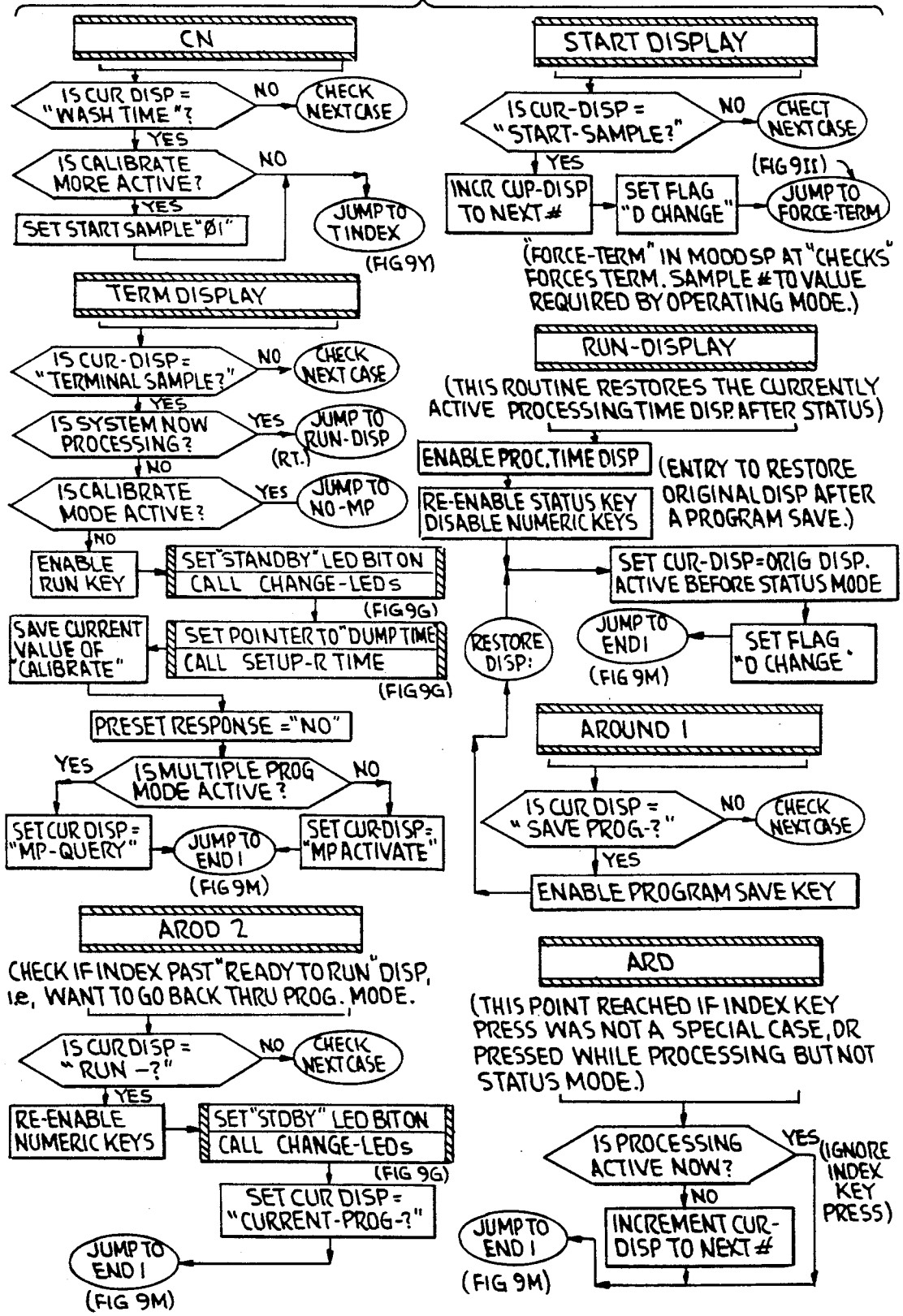
Figure 9C:
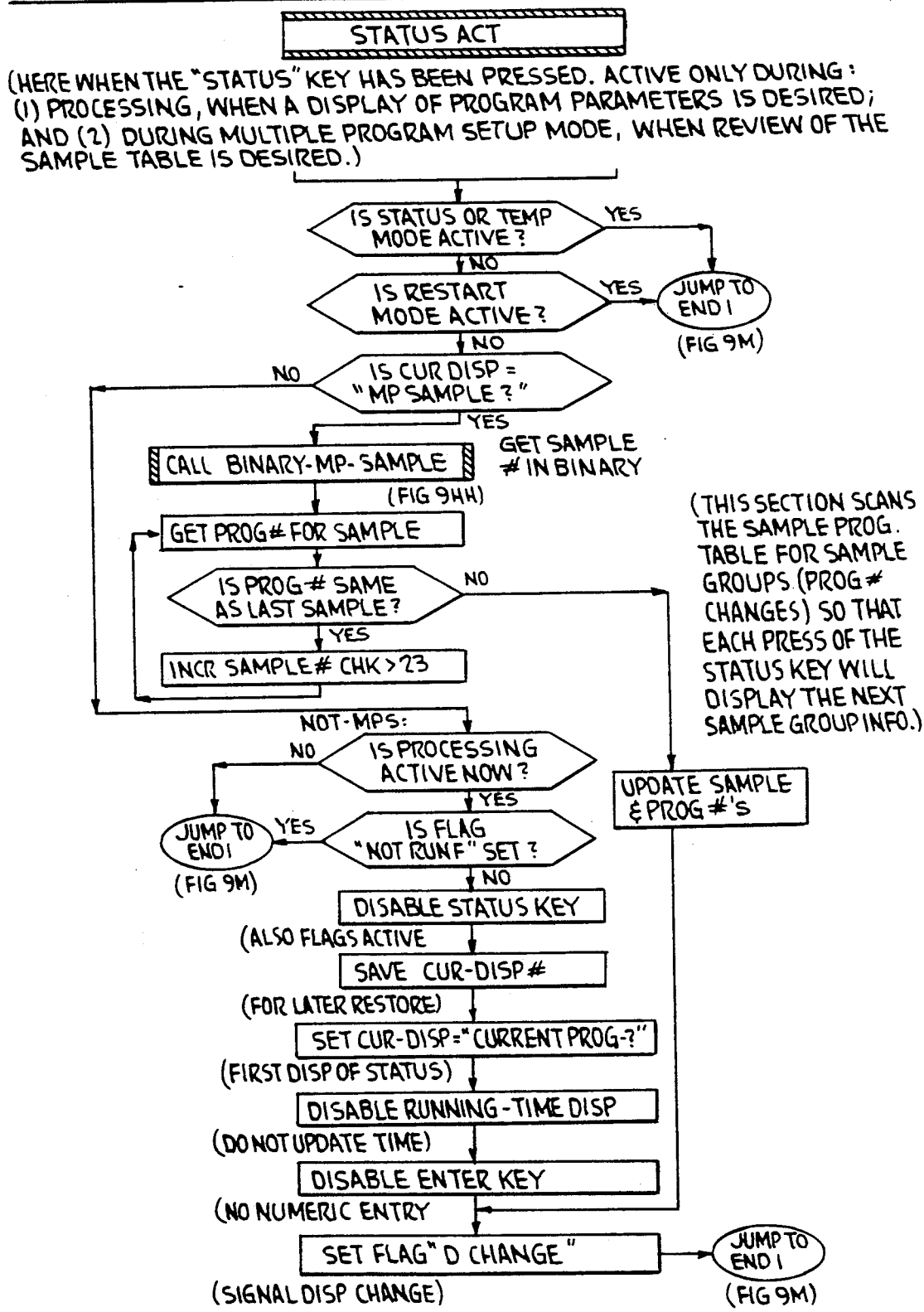
Figure 9D:
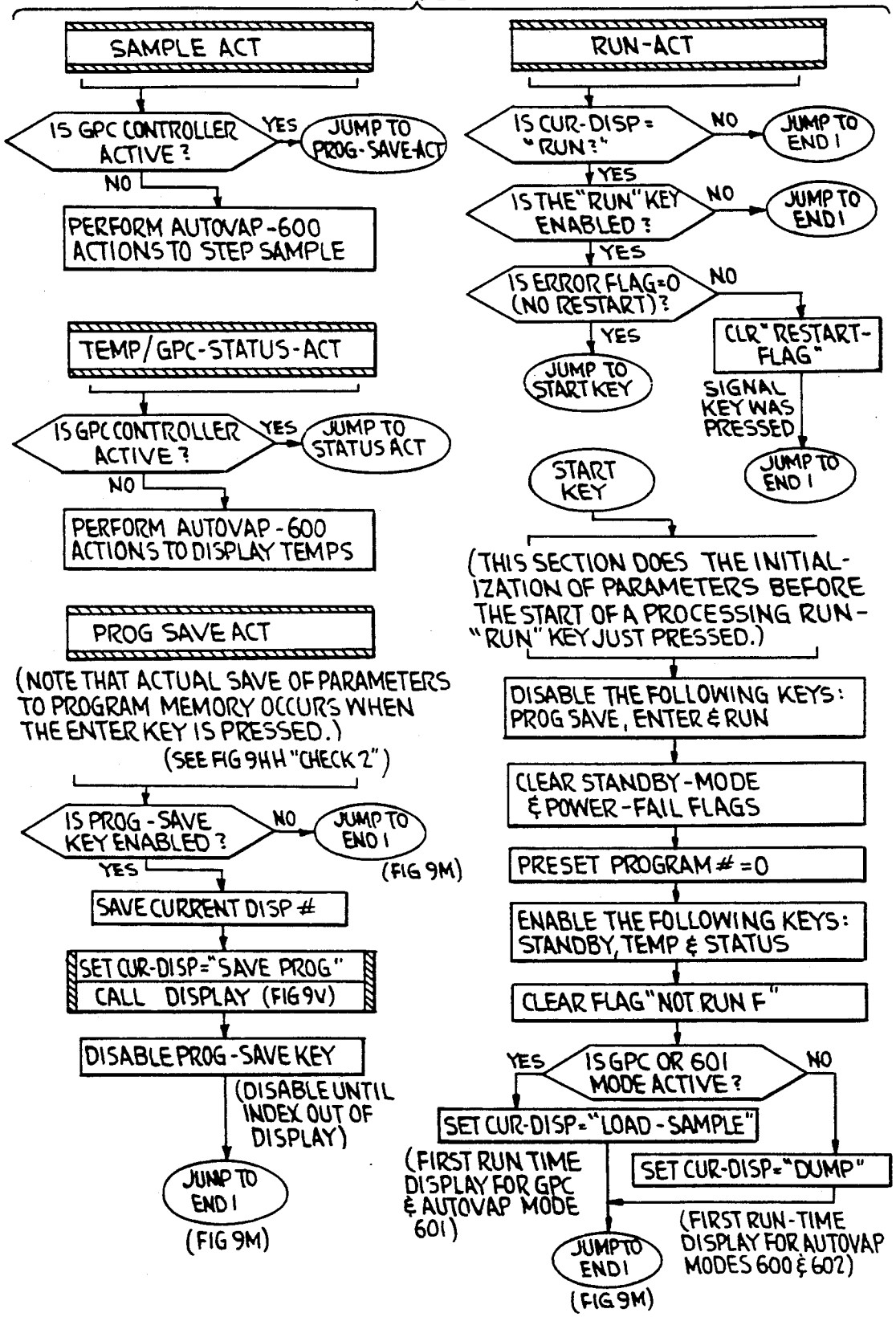
Figure 9E:
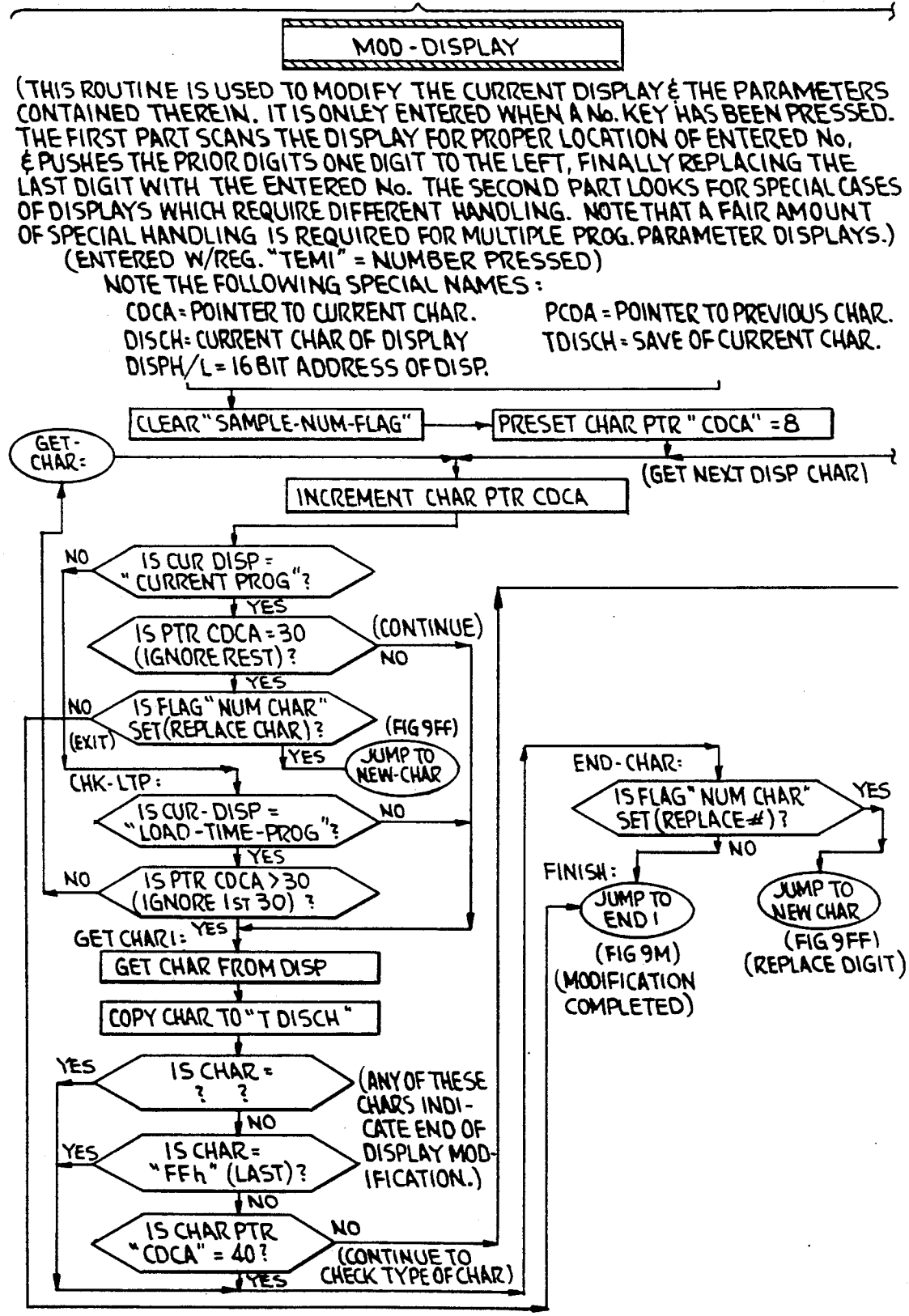
Figure 9E:
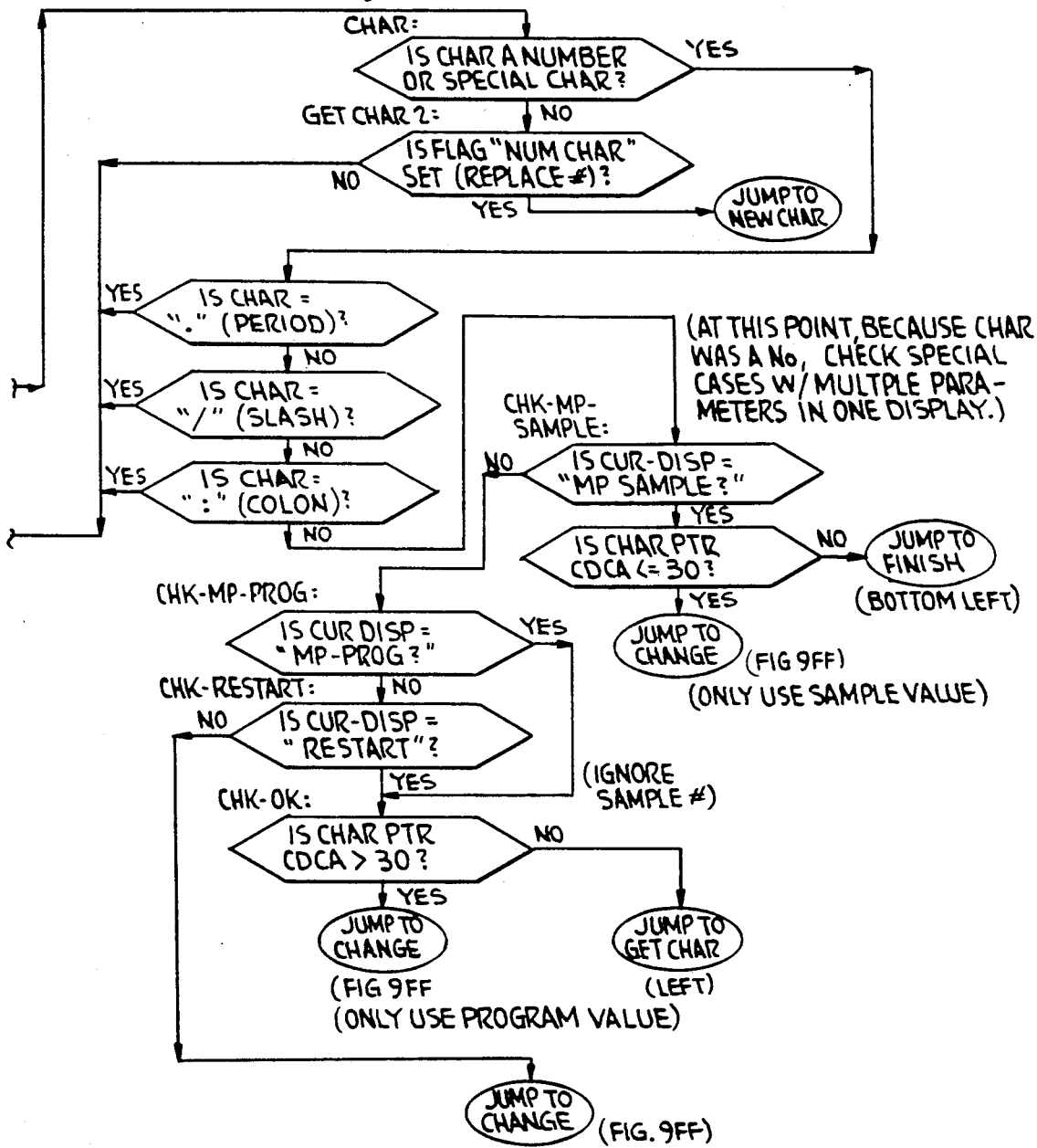
Figure 9F:
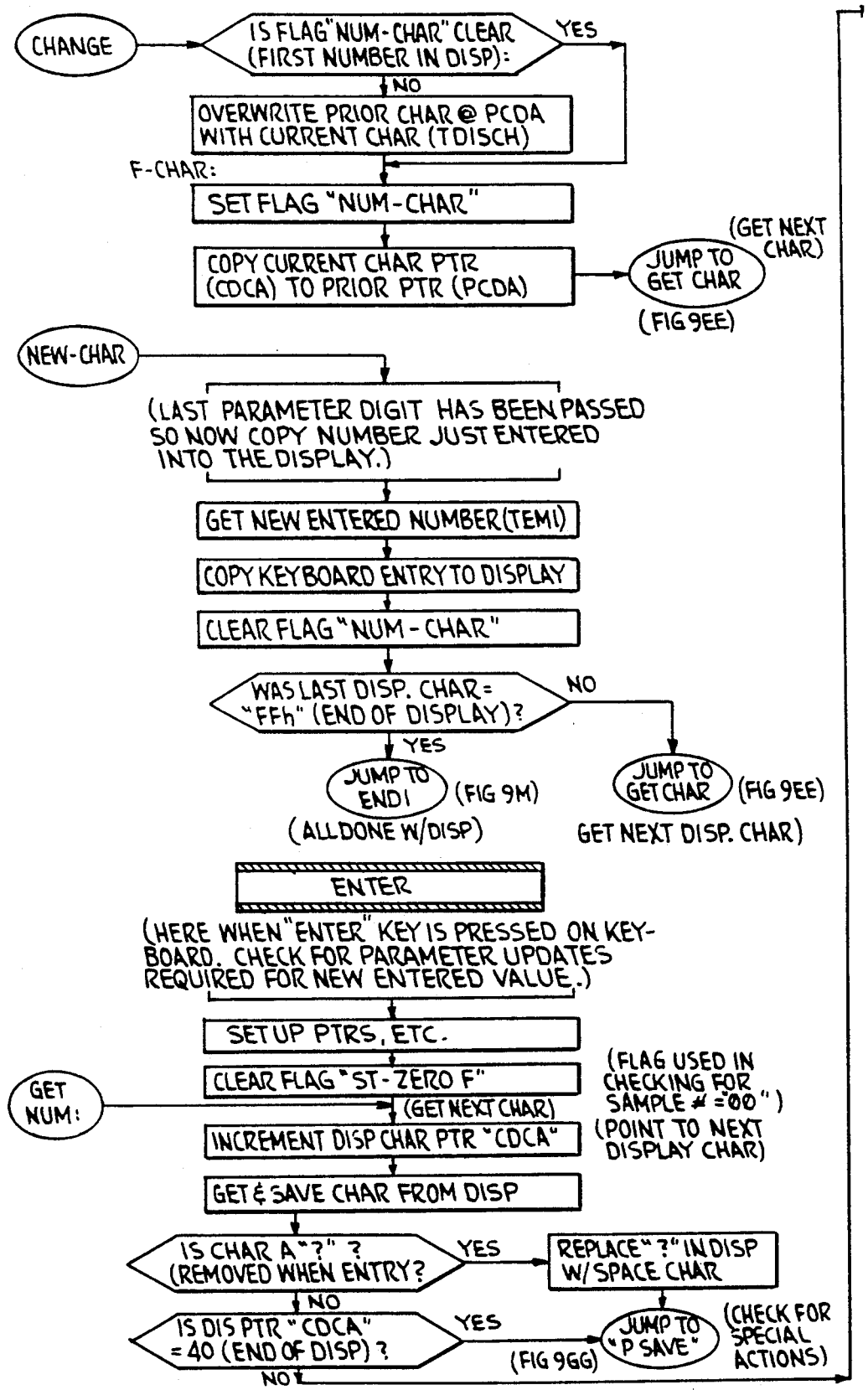
Figure 9G:
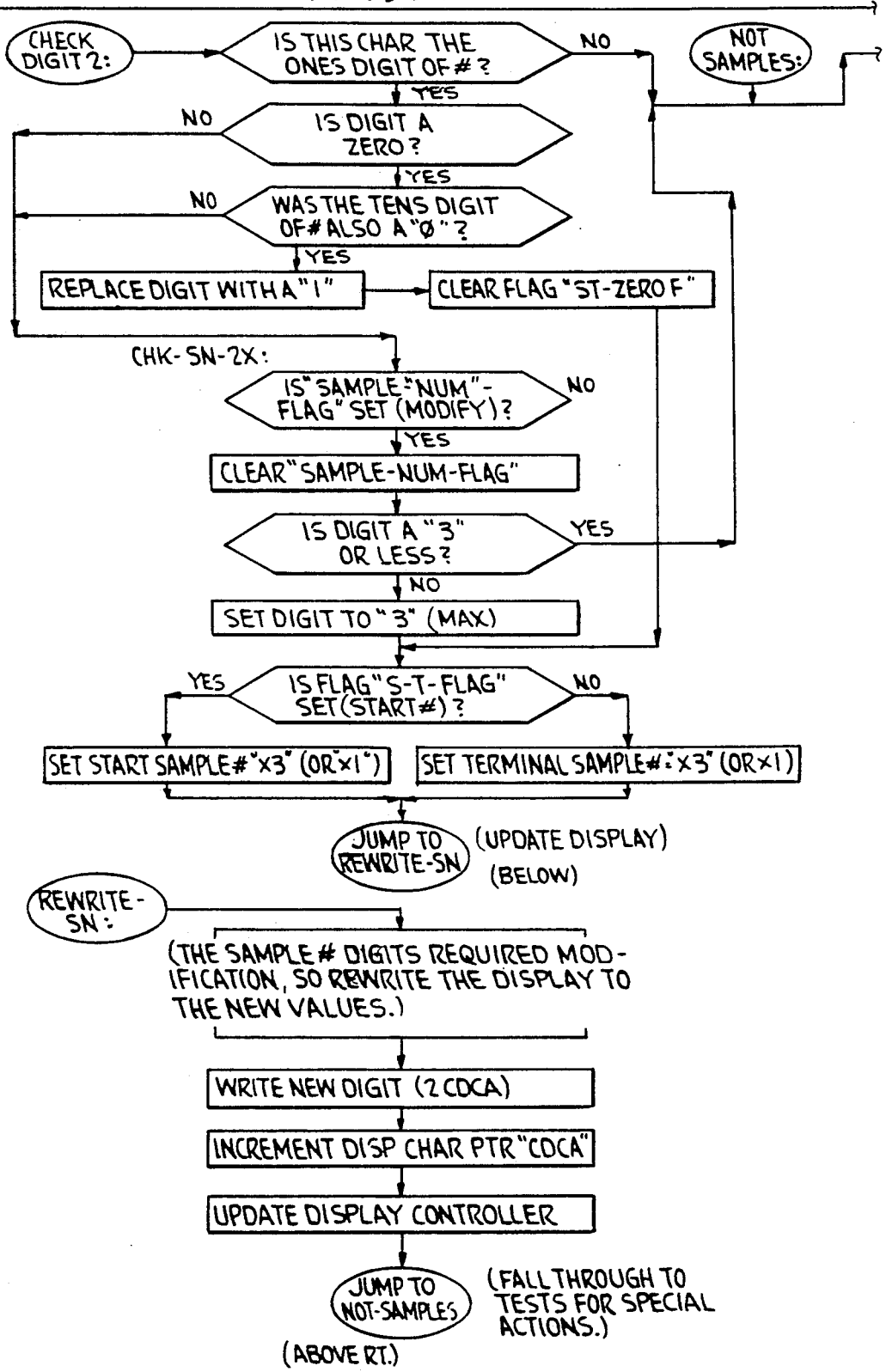
Figure 9G:
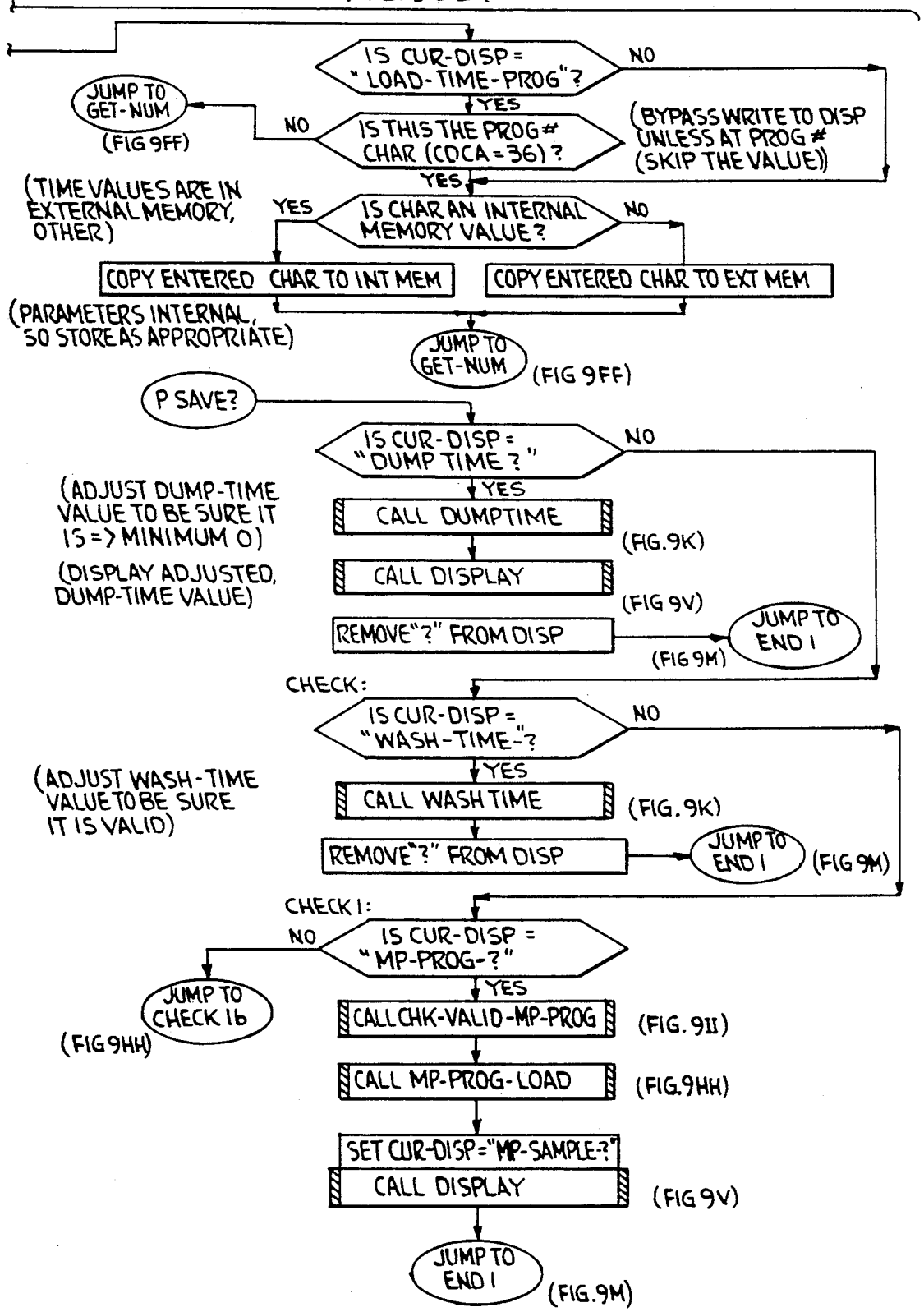
Figure 9H:
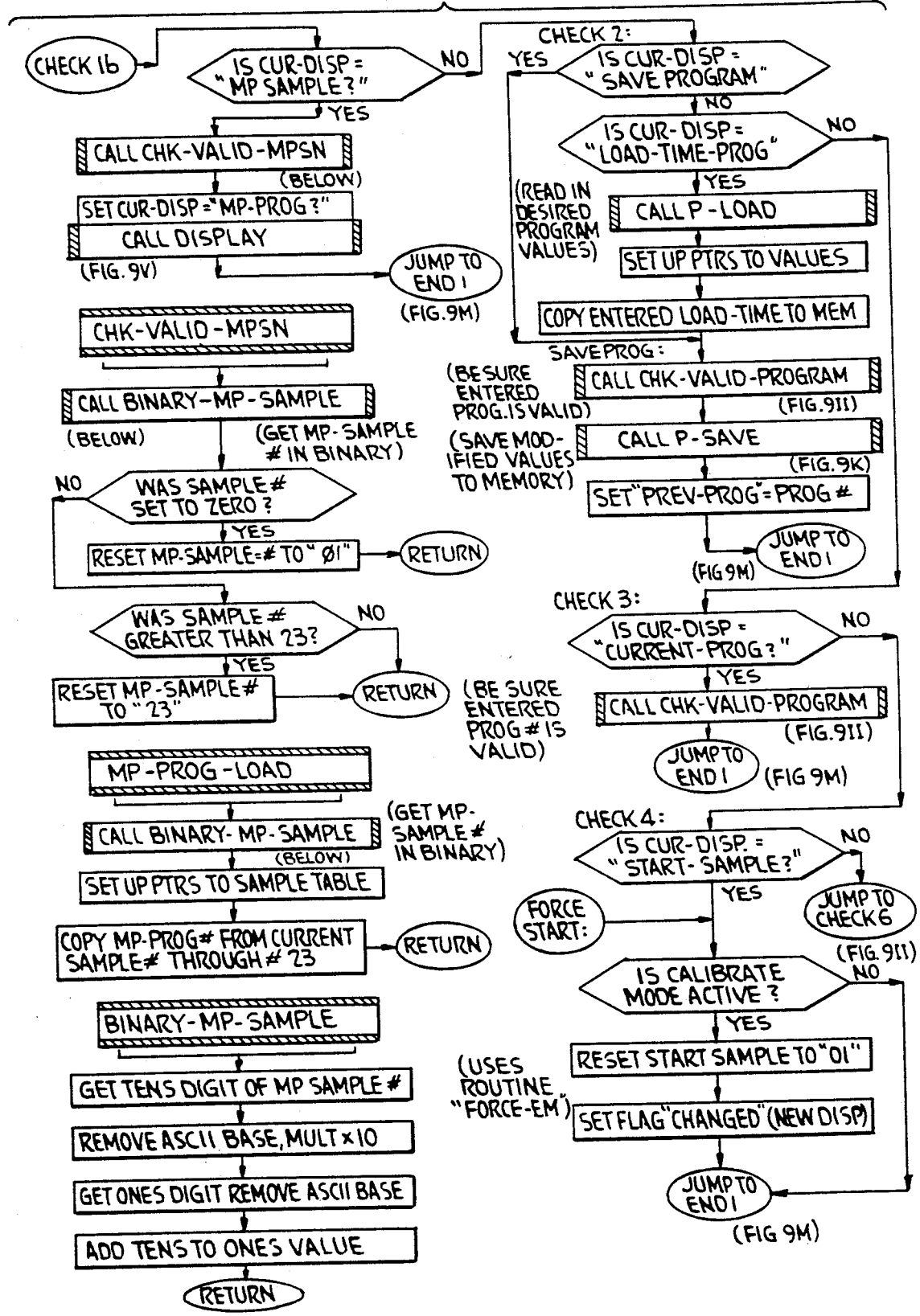
Figure 9I:
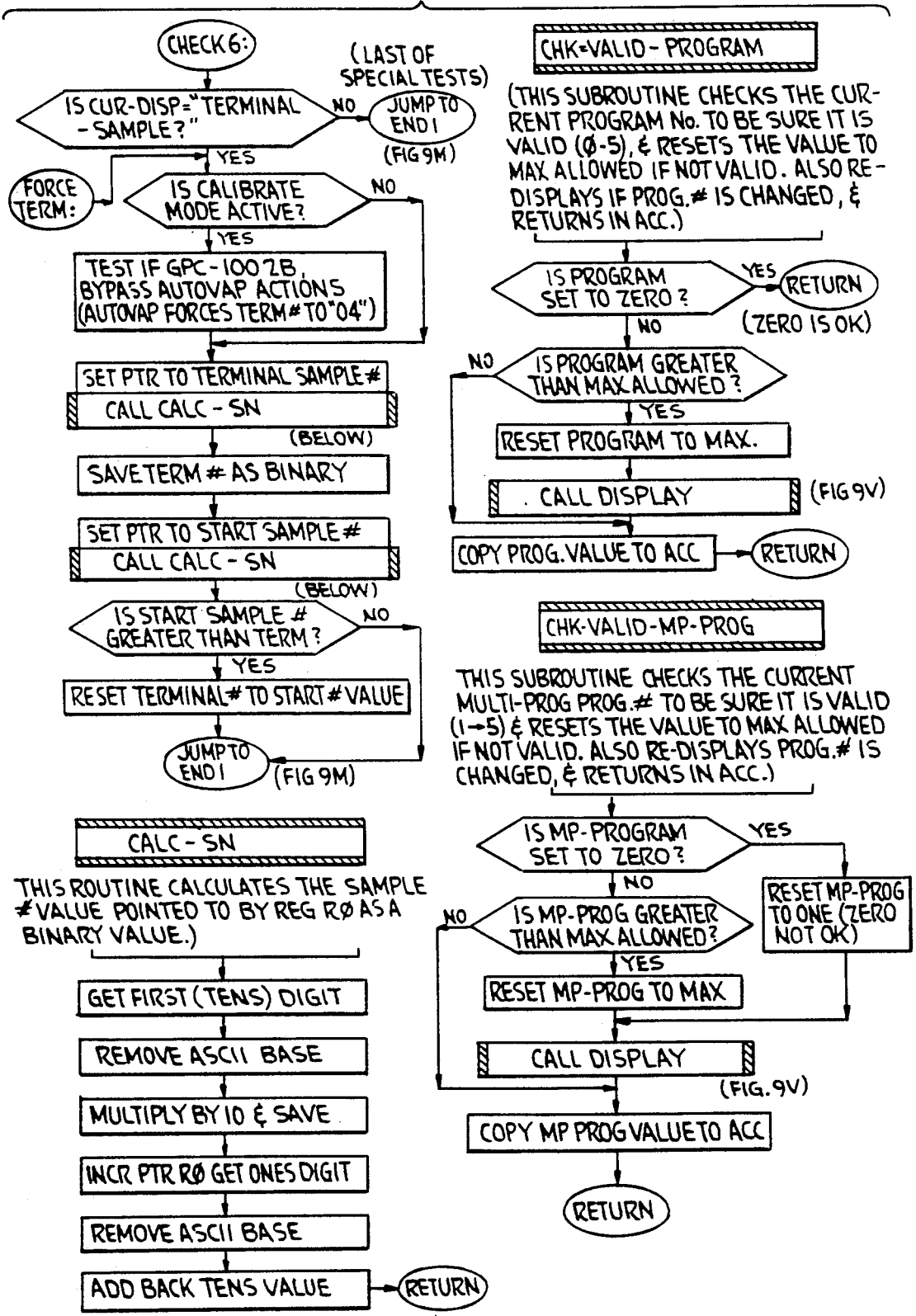

When power is first applied to the system, an initialization procedure is begun (see FIG. 9A) followed by a system self-test sub-routine (FIG. 9U). Thereafter the system proceeds to the set-up mode (FIG. 9B). In that mode the system may display various service prompt messages directing the operator to perform respective tasks. After performing the task described in the prompt, the operator presses the index key at the keyboard in order to cause the system to proceed to the next prompt message. To return to the first service prompt, the user may actuate the standby key. More particularly, for the set-up mode (FIG. 9B) the system enters the standby routine (FIG. 9S) if the standby key is actuated. As part of this routine, the system determines that it is in the set-up mode, causing the no-restart sub-routine (FIG. 9T) to be called. The "fill rinse and solvent vessels" prompt is displayed during this sub-routine (see display number five in the index-act routine, FIG. 9X). In conjunction with an instruction manual that accompanies the system, this prompt requests the operator to fill the sample solvent reservoir 15 and rinse solvent reservoir 11 with enough fluid for a process run. After this operation is performed, the operator is requested to actuate the index key to proceed to the next sequential service prompt. These service prompts are sequentially listed in the index-act routine illustrated in FIG. 9X.

The setting of the time interval required to load a given sample into sample loop 16 may be effected when the "sample load time" prompt (display number thirteen, FIG. 9X) is displayed. Actually, this prompt appears on the display as "run sample load auto timer (No.=0)—0". The "0" at the end of the display is a default entry which, if followed by actuation of the index key, bypasses the step of loading the sample load time into the system. However, entry of a "1" followed by index key actuation permits the load interval to be set by the operator. In such case, the system displays a warning that the auto timer uses sample number one. Accordingly, the operator must be sure that position one is provided with a flask containing a solution representative of samples to be processed and in a volume equal to the volume of sample to be processed. The system is ready to cause this fluid, from sample container number one, to be passed through the sample load flow path and dumped to vent via port E of sample inject valve V7. When the operator actuates the index key, the display reads "enter to start/stop timer 0:00:0". Actuation of the enter key causes the valve V12 to assume its number one position, and pressurized gas is delivered to the accessed sample container 13 via its delivery tube 23. Sample fluid is driven through the pick-up tube 22 of the accessed container 13 and into valve section 12A to the sample loop 16 via ports D and C of valve V7. A timer also starts when the enter key is actuated, thereby causing the displayed time to increment as a measure of elapsed time. When the sample fluid in sample container 13 drops to below the mouth of pick-up tube 22, the operator must actuate the enter key once again to stop the timer. The displayed time is the sample load time that will be used by the autotimer. The elapsed time may be checked by loading another sample at position number one and using the enter key to start and stop the timer as described above. When a reliable time is obtained, the operator actuates the index key, resulting in the display of an inquiry as to which of the five possible programs should be loaded with the measured time. Entry of the program number(s) at the keyboard, followed by actuation of the entry key, effects loading of the measured load time into the appropriate programs. If the index key is actuated without actuation of the enter key, the measured load time is not saved. After the measured load time is saved, the operator actuates the index key to proceed with the set-up operation. Assignment of different sample positions to one of the five possible stored load times is effected by means of the multiple program check (MP-Check) subroutine (FIG. 9AA).

In order to determine the correct dump and collect time intervals for analytes to be recovered quantitatively and separated from the sample matrix, the elution profiles of the sample matrix and analytes must be known. To accomplish this, a fractionation of the column eluent must be performed. Ideally, the sample to be fractionated will be a solution of a sample matrix and representative analytes in the column eluting solvent. The concentration of the sample matrix should be the same as the usual samples to be analyzed (e.g., 1 gm per 5 mLs). To facilitate detection in the beginning and ending fraction, the concentration of analytes should be ten times the amount expected in routine samples.

In order to program the system for autofractionation, the operator must actuate the numeral "1" at the keyboard, followed by actuation of the enter key, in response to a prompt requesting whether or not the calibration mode is desired. This causes the prompt message "CURRENT PROGRAM=*?" to be displayed, where * is the current program number. The operator must enter the desired program number (one through five) to be used for the fractionation. This is followed by actuation of the enter key and the index key in sequence. When the message "SAMPLE LOAD TIME=*:**.*?" is displayed, the operator must press the index key to utilize the displayed time and proceed to the next prompt. The time displayed corresponds to the time measured and saved during the sample load interval procedure described above. The next prompt appearing on the display is the "DUMP TIME=:?", where the : portion of the display is the last dump interval that was stored for the current program. The operator must then enter the correct dump interval to be employed followed by actuation of the enter and index keys. The dump interval is the time during which there will be no compounds of interest in the column effluent.

The next prompt to appear on the display is "COLLECT TIME=:?", where ":" is the last collect interval that was stored for the current program. The operator must enter the desired collect time interval followed by the enter and index keys. The collect interval determines the volume of the fractions that are to be collected. A pump flow rate set at 5 mL per minute a collect time of two minutes results in ten mL fractions.

The next message displayed is "WASH TIME=:?", where : is the last wash time interval that was stored for the current program. For the present it is assumed that the wash interval is zero and, accordingly, 00:00 is entered followed by actuation of the enter and index keys.

When the message "START WITH SAMPLE #=?" is displayed (where  is the last starting sample that was stored for the current program), the operator enters "01" followed by actuation of the enter and index keys. When the message "TERMINAL SAMPLE #=?" is displayed (where  is the last terminal sample that was stored for the current program), the operator enters the desired number of fractions for the calibration followed by actuation of the enter and index keys.

The next message displayed is "PROCESS WITH MULT PROGRAMS (NO=0)−0?". The operator actuates the index key to respond "no"; the multiple program mode cannot be utilized during calibration. When the display reads "LAST SAMPL=−TIME=:−PUSH RUN?" (where  is the number of fractions and : is the dump time interval), the operator actuates the program save key. When 22 the message "SAVE AS PROGRAM *?" is displayed (where * is the current program), the operator actuates the enter key to save the program values to the current program which is the program chosen for fractionation. Thereafter, the index key must be actuated to terminate fractionation programming.

In order to start a fractionation process, when the message "LAST SAMPL−−TIME=:−PUSH RUN?" is displayed (where  is the number of fractions and : is the dump time interval), the operator may actuate the run key. If that message is not displayed, the operator may actuate the index key repetitively until that message is displayed.

During the sample load interval of a fractionation operation, the twenty-four port valve V12 is stepped to the first position and the corresponding sample is loaded into sample loop 16. At the end of the sample loading time, the sample inject valve V7 is switched to its run position and the dump interval begins. The sample is injected into the column 21 followed by sample solvent from reservoir 15. In addition, during the first portion of the dump interval, the sample container 13 is rinsed with solvent from the rinse loop 12, the rinse solvent is then being directed to a waste container. During the dump interval the effluent from column 21 is also directed through dump/collect valve V6 to a waste container.

During the collect interval (first fraction), the dump/collect valve is energized and column effluent is directed to the first sample collection flask 14. When the collect time interval terminates, the twenty-four port valve V12 is stepped to its next sample position, the collect interval is reset to the programmed value, and the second fraction is directed to the second sample collection flask 14. This process is repeated until all fractions are collected and the fractionation process is completed.

In programming the system for sample processing, the first step is selecting an appropriate program. When the message "CURRENT PROGRAM=*?" is displayed (where * is the current program number), the operator enters the desired program number to be utilized for sample processing, followed by actuation of the enter key and the index key. To enter the sample load time interval, when the message "SAMPLE LOAD TIME *:**.*?" is displayed, the operator actuates the index key to utilize the displayed time and proceed to the next message. The time displayed should correspond to the time measured and saved when the sample load timer was set in the manner described above. Thereafter, in order to enter the dump time, when the message "DUMP TIME=:?" is displayed (where : is the last dump interval that has been stored for the current program), the operator enters the correct dump interval followed by actuation of the enter and index keys. The dump interval is the time during which there will be no compounds of interest in the column effluent.

The next prompt to appear on the display is "COLLECT TIME=:?", where ":" is the last collect interval that was stored for the current program. The operator must enter the desired collect time interval followed by the enter and index keys. The collect interval determines the volume of the fractions that are to be collected.

The next message displayed is "WASH TIME=:?", where : is the last wash time interval that was stored for the current program. The operator enters the desired wash time interval followed by actuation of the enter and index keys.

When the message "START WITH SAMPLE#=?" is displayed (where  is the last starting sample that was stored for the current program), the operator enters the desired starting sample number followed by actuation of the enter and index keys. When the message "TERMINAL SAMPLE #=?" is displayed (where  is the last terminal sample that was stored for the current program), the operator enters the desired number of the last sample to be processed followed by actuation of the enter and index keys.

Program changes may be saved at any time during the programming operation by actuating the program save key (PS). When this key is actuated the message "SAVE AS PROGRAM *?" is displayed (where * is the number of the last program selected). To save program changes, the operator enters one of numerals one through five followed by actuation of the enter key. When the enter key is actuated the parameters are saved for the corresponding program number, replacing any existing parameters stored in that program. When the index key is actuated, the same message that was displayed when the program save key was actuated will be re-displayed.

In the single program mode, all samples are processed utilizing program 0, which is the program selected during normal processing when multiple programs are not employed, with changes being made during subsequent program displays. If the changes made are not saved to a program numbered one through five using the program save key, the changes are lost should programs one through five be later selected.

Before selecting a multiple program mode, all programs to be utilized must be entered and saved as one of programs one through five. Program zero is not utilized for the multi-program mode; therefore, changes must be saved using the program save key. Programs can be created by selecting an existing program, by changing parameters as required, and saving the changes under a different program number which is not already utilized. In addition, an unused program number can be selected, the parameters entered, and the program saved under that number utilizing the program save key.

In operation during typical sample processing, when the run key is actuated, the twenty-four port valve V12 is stepped to the starting sample position. The message: "WAIT--INDEXING TO SAMPLE " is displayed (where  is the starting sample number). When valve V12 reaches the starting sample position, the sample load interval is initiated. If the valve does not index properly, the message "ERR--SAMPLE # FAILED TO INDEX" is displayed (where  is the sample to be processed). During the sample load interval, the sample is loaded into sample loop 16. The message "SAMPLE=** LOADING TIME=*:**.*" is displayed (where ** is the number of the sample being processed and *:**.* is the time remaining in the sample load interval).

When the sample load time interval counts down to zero, the dump interval begins and the sample input valve is switched to the run position. The message "SAMPLE= DUMP TIME=:*" is displayed (where  is the sample being processed and :** is the dump time remaining in the interval). The accessed sample is injected into column 21 followed by sample solvent from solvent reservoir 15. Effluent from column 21 is directed through the dump/collect valve V6 to a waste container.

During the first minute of the dump interval, the accessed sample container 13 is rinsed with rinse solvent from rinse solvent loop 12, after which the loop is automatically refilled When the dump interval expires, the collect interval begins. The dump/collect valve V6 is energized and column effluent is directed to the appropriate collection flask 14 selected by the valve section V12C. The message "SAMPLE= COLLECT TIME :" is displayed (where  is the number of the sample being processed and : is the time remaining in the collect interval). Upon termination of the collect interval, wash time begins. The sample inject valve V7 is switched to its load position and the dump/collect valve is deenergized. Column effluent is directed to the waste container. The message "SAMPLE  WASH TIME=:" is displayed (where  is the number of the sample being processed and : is the time remaining in the wash interval). When the wash interval expires and more samples remain to be processed, the twenty-four port valve V12 is stepped to the next sample position and the process is repeated, beginning with the sample load interval. When all samples are processed, the solvent pump is deactivated and the message "SAMPLE= PROCESSING COMPLETED" is displayed (where  is the number of the last sample to be processed).

The system is designed to operate during power failures of up to thirty minutes when the batteries are fully charged. When a power failure occurs, all program parameters and current processing information are saved. When power is restored, sample processing resumes at the point where the power failure occurred. When sample processing is completed, the message "ERR-POWER FAILURE AT SAMPLE=, LS=XX" is displayed (where  is the number of the sample being processed when the power failure occurred and XX is the last sample to be processed). If multiple power failures occur, only the earliest processed sample number is displayed. Actuation of the index key causes the system to proceed to the first service prompt message.

If the system pressure exceeds the stated maximum (i.e., typically 20 psi) sample processing is halted. The message "ERR GPC OVRPRESS . . . PROCESS STOPPED=" is displayed (where  is the number of the sample being processed when the failure occurred).

From the foregoing description it will be appreciated that the present invention makes available a novel single-loop chromatography method and apparatus wherein a technique for automatically loading samples into a common sample sizing loop significantly reduces the time required for loading the system and initiating operation as compared to prior art systems. Operation of the system can be initiated immediately after the first sample is loaded into the sample sizing loop, while leakage and other hazards associated with syringe loading have been eliminated by the automatic loading approach. Plural operating programs are provided to permit processing of various sample types, and carry-over contamination from sample to sample is eliminated with an automatic rinsing process. The common sample sizing loop allows for greater precision and samples may be added to the system while another sample is being processed. A unique sealing arrangement is provided for each storage sample container suspended from a support arm so as to prevent leakage when the sample container is pressurized during loading and rinsing procedures.

Having described a preferred embodiment of a new and improved single-loop chromatography method and apparatus, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed:

1. A chromatography system comprising:
 a chromatography column;
 multiple storage containers each storing in excess of a predetermined volume of a respective sample fluid to be chromatographically treated in said column to obtain qualitative components for analysis;
 a common sample sizing container having a capacity of said predetermined volume;
 loading means for automatically loading and filling said sizing container with individual samples of sample fluid from respective containers of said multiple storage containers via a common flow path in a selected sequence;
 means for automatically passing each of said individual samples from said common sizing container through said column;
 collection means for storing at least one of said qualitative components from each of said individual samples passed through said column;
 a system housing;
 multiple support arms each having a proximal end secured to said housing and a distal end remove from said housing, said distal end having a top side and an underside;
 attachment means for suspending each sample storage container from the distal end of a respective support arm, said attachment means comprising:
  a closure member having top and bottom surfaces and an axially-extending closure bore defined therein between said top and bottom surfaces, wherein said closure bore includes a top section diametrically enlarged relative to a bottom section to thereby define an upwardly-facing annular shoulder at the juncture between the top and bottom sections, and wherein said bottom section is sized to receive and engage an upper end of a respective sample storage container;
 a closure insert having an axial length substantially equal to the axial length of the top section of said closure bore and radially dimensioned to correspond to the top section of the closure bore so that the closure insert fits snugly in the top section of the closure bore with the top of said closure insert substantially flush with the top surface of said closure member;
 wherein said closure insert has an axial insert bore defined therethrough in coaxial alignment with the closure bore, said insert bore having two axial portions, namely an upper threaded portion of relatively small diameter and a lower portion of relatively large diameter, the upper and lower portions joining one another at a downwardly-facing annular shoulder;
 an O-ring disposed in said lower portion of said insert bore and contained between said upwardly-facing shoulder and said downwardly-facing shoulder;
 wherein each support arm has an access hole defined through from said top side to said underside;
 means securing said closure member to said respective support arm with the top surface of the closure member flush against said underside and with said access hole aligned with said insert and closure bores to permit conduction of fluid between said each sample storage container and a location above the top side of said respective support arm;
 connector means disposed proximate the top side of said respective support arm and having a hollow body, a bottom male fitting extending through said access hole and threaded to engage the upper threaded bore section of said closure insert, and first and second top fittings;
 a first tube extending through said top fitting, the hollow connector body, the bottom male fitting and the aligned insert and closure bores to approximately the bottom of said sample storage container; and
 fluid conduit means secured to said second top fitting in flow communication with the upper end of said sample storage container via the hollow connector body and an annular flow path disposed about said first tube through said bottom fitting and said insert and closure bores;
 wherein said first tube is part of said loading means and conducts fluid out of said sample storage container; and
 wherein said fluid conduit means is arranged to deliver fluid under pressure to said sample storage container to force fluid out of said sample storage container via said first tube.

2. A chromatography system comprising:
 a chromatography column;
 multiple storage containers each storing in excess of a predetermined volume of a respective sample fluid to be chromatographically treated in said column to obtain qualitative components for analysis;
 a common sample sizing container having a capacity of said predetermined volume;
 loading means for automatically loading and filling said sizing container with individual samples of sample fluid from respective containers of said multiple storage containers via a common flow path in a selected sequence, said loading means comprising a source of pressurized purge fluid and means for selectively pressurizing each of said storage containers with said purge fluid to force sample fluid through said common flow path to said sizing container;

means for automatically passing each of said individual samples from said common sizing container through said column;

collection means for storing at least one of said qualitative components from each of said individual samples passed through said column;

cleansing means for cleansing said common flow path, said common sizing container and said column of sample fluid before loading each of said individual samples into said sizing container; and a multiple port valve having at least first and second commonly actuated valve sections, said first and second valve sections each including a common port and multiple individually accessible ports equal in number to at least a number of said multiple storage containers, wherein flow communication is provided between the common port and only the currently accessed port;

wherein said loading means includes:

multiple pick-up tubes, each connected from a respective storage container to a respective accessible port of the first valve section to deliver sample fluid to the common port of said first valve section when said respective storage container is pressurized;

multiple delivery tubes, each connected from a respective storage container to a respective accessible port of the second valve section, for delivering pressurized fluid from the common port of said second valve section to pressurize said respective storage container;

selectively actuable purge control means for selectively delivering pressurized purge fluid to the common port of said second valve section; and selectively actuable selection means for selectively providing flow communication between the common port of said first valve section and said common sizing container.

3. The chromatography system according to claim 2 wherein said cleansing means comprises selectively actuable rinse control means for selectively delivering rinse solvent fluid under pressure to the common port of said second valve section, wherein said sample fluid dissolves in said rinse solvent.

4. The chromatography system according to claim 3 further comprising:

flow regulator means for supplying said purge gas at a known pressure and flow rate;

a rinse solvent container for temporarily storing a predetermined volume of said rinse solvent; and individually actuable vent, purge and rinse valves, each having a common port, a normally open port in flow communication with said common port only when the valve is not actuated, and a normally closed port in flow communication with said common port only when the valve is actuated;

wherein said purge control means includes: conduit means connecting purge gas from said flow regulator means to the normally closed port of said purge valve; conduit means connecting the common port of said purge valve to the normally open port of said rinse valve; and conduit means connecting the common port of said rinse valve to the common port of said first section of said multiple port valve;

wherein said rinse control means comprises: conduit means connecting said purge gas from said flow regulator to the normally closed port of said vent valve; conduit means connecting the common port of said vent valve to said rinse solvent container to permit purge gas passing through the vent valve common port to pressurize the rinse solvent container; and rinse solvent flow means for delivering rinse solvent from said rinse solvent container, when pressurized, to the normally closed port of said rinse valve;

wherein said loading means includes means for selectively actuating said purge valve while maintaining said vent and rinse valves unactuated; and wherein said cleansing means includes means for selectively actuating said vent and rinse valves while maintaining said purge valve unactuated.

5. The chromatography system according to claim 4 wherein said cleansing means comprises: a reservoir for said rinse solvent; a selectively actuable loop fill valve having a normally closed port, a normally open port and a common port in flow communication with said normally closed port when the loop fill valve is actuated and in flow communication with said normally open port when the loop fill valve is unactuated; conduit means connecting the rinse solvent reservoir to the normally open port of said loop fill valve; and conduit means incorporated as part of said rinse solvent flow means connected between the common port of said loop fill valve and the rinse solvent container to conduct rinse solvent to and from the rinse solvent container in accordance with the pressure conditions in the rinse solvent container;

wherein said rinse solvent flow means further includes conduit means providing flow communication between the normally closed port of said loop fill valve and the normally closed port of said rinse valve; an wherein said loop fill valve is only actuated by said cleansing means while said vent and rinse valves are actuated and said purge valve is unactuated.

6. The chromatography system according to claim 4 further comprising:

a sample inject valve having six ports A, B, C, D, E and F, and selectively actuable between first and second positions;

wherein at said first position flow communication is provided between ports A and B, between ports C and D and between ports E and F;

wherein for said second position fluid communication is provided between ports A and F, between ports B and C and between ports D and E;

wherein said common sizing container is a length of tubing having a first end connected to port C and a second end connected to port F;

wherein said loading means includes a conduit connected with substantially no slack between the common port of the first section of said multiple port valve and port D;

wherein said means for automatically passing includes a source of sample solvent in which said one qualitative component may be analyzed as a solute, and means for delivering said sample solvent under pressure to port B;

conduit means providing flow communication between port A and one end of said chromatography column;

means for venting port E; and control means for automatically actuating the sample inject valve to its first position in order to load an individual sample into said common sizing container and to its second position to pass the individual sample located in the common sizing container through said column.

7. The chromatography system according to claim 6 further comprising:
a selectively actuable dump/collect valve having a normally closed port, a vented normally open port and a common port in fluid communication with the normally open port when the dump/collect valve is unactuated and in flow communication with said normally closed port when said dump/collect valve is actuated;
conduit means providing fluid communication between the second end of said chromatography column and the common port of said dump/collect valve;
multiple sample collection containers, one for each of said sample storage containers;
a third valve section of said multiple port valve actuable with said first and second sections of said multiple port valve and including: a common port connected in fluid communication with the normally closed port of said dump/collect valve; and plural individually-accessible ports each connected in flow communication with a respective sample collection container; and
means for selectively actuating said dump/collect valve at a selected time after actuation of said sample inject valve to permit collection in a respective sample collection container of only sample fluid egressing from said chromatography column after said selected time 8. The chromatography system according to claim 2 further comprising:
a sample inject valve having six ports A, B, C, D, E and F, and selectively actuable between first and second positions;
wherein at said first position flow communication is provided between ports A and B, between ports C and D and between ports E and F;
wherein for said second position fluid communication is provided between ports A and F, between ports B and C and between ports D and E;
wherein said common sizing container is a length of tubing having a first end connected to port C and a second end connected to port F;
wherein said loading means includes a conduit connected with substantially no slack between the common port of the first section of said multiple port valve and port D;
wherein said means for automatically passing includes a source of sample solvent in which said one qualitative component may be analyzed as a solute, and means for delivering said sample solvent under pressure to port B;
conduit means providing flow communication between port A and one end of said chromatographic column;
means for venting port E; and
control means for automatically actuating the sample inject valve to its first position in order to load an individual sample into said common sizing container and to its second position to pass the individual sample located in the common sizing container through said column.

9. The chromatography system according to claim 8 further comprising:

a selectively actuable dump/collect valve having a normally closed port, a vented normally open port and a common port in fluid communication with the normally open port when the dump/collect valve is unactuated and in flow communication with said normally closed port when said dump/collect valve is actuated;
conduit means providing fluid communication between the second end of said chromatographic column and the common port of said dump/collect valve;
multiple sample collection containers, one for each of said sample storage containers;
a third valve section of said multiple port valve actuable with said first and second sections of said multiple port valve and including a common port connected in fluid communication with the normally closed port of said dump/collect valve; and plural individually-accessible ports each being connected in flow communication with a respective sample collection container; and
means for selectively actuating said dump/collect valve at a selected time after actuation of said sample inject valve to permit collection in a respective sample collection container of only sample fluid egressing from said chromatographic column after said selected time.

10. The chromatography system according to claim 9 further comprising:
a system housing;
multiple support arms each having a proximal end secured to said housing and a distal end remote from said housing, said distal end having a top side and an underside;
attachment means for suspending each sample storage container from the distal end of a respective support arm, said attachment means comprising:
a closure member having top and bottom surfaces and an axially-extending closure bore defined therein between said top and bottom surfaces, wherein said closure bore includes a top section diametrically enlarged relative to a bottom section to thereby define an upwardly-facing annular shoulder at the juncture between the top and bottom sections, and wherein said bottom section is sized to receive and engage an upper end of a respective sample storage container;
a closure insert having an axial length substantially equal to the axial length of the top section of said closure bore and radially dimensioned to correspond to the top section of the closure bore so that the closure insert fits snugly in the top section of the closure bore with the top of said closure insert substantially flush with the top surface of said closure member;
wherein said closure insert has an axial insert bore defined therethrough in coaxial alignment with the closure bore, said insert bore having two axial portions, namely an upper threaded portion of relatively small diameter and a lower portion of relatively large diameter, the upper and lower portions joining one another at a downwardly-facing annular shoulder;
an O-ring disposed in said lower portion of said insert bore and contained between said upwardly-facing shoulder and said downwardly-facing shoulder;
wherein each support arm has an access hole defined through from said top side to said underside;

means securing said closure member to said respective support arm with the top surface of the closure member flush against said underside and with said access hole aligned with said insert and closure bores to permit conduction of fluid between said each sample storage container and a location above the top side of said respective support arm;

connector means disposed proximate the top side of said respective support arm and having a hollow body, a bottom male fitting extending through said access hole and threaded to engage the upper threaded bore portion of said closure insert, and first and second top fittings:

a first tube extending through said first top fitting, the hollow connector body, the bottom male fitting and the aligned insert and closure bores to approximately the bottom of said sample storage container; and fluid conduit means secured to said second top fitting in flow communication with the upper end of said sample storage container via the hollow connector body and an annular flow path disposed about said first tube through said bottom fitting and said insert and closure bores;

wherein said first tube corresponds to said pick-up tube, and said fluid conduit means corresponds to said delivery tube.

11. The chromatography system comprising:
a chromatography column;
multiple storage containers each storing in excess of a predetermined volume of a respective sample fluid to be chromatographically treated in said column to obtain qualitative components for analysis;
a common sample sizing container having a capacity of said predetermined volume;
a common flow path;
load means for automatically loading and filling said sizing container with individual samples of said sample fluid from respective containers of said multiple storage containers via said common flow path in a selected sequence;
a container of sample solvent liquid;
a sample solvent flow path for conducting the sample solvent liquid from said container of sample solvent liquid to said chromatography column;
pump means for substantially continuously pressurizing said sample solvent liquid to cause it to flow through said sample solvent flow path and said chromatography column;
valve means for temporarily inserting said sizing container into said sample solvent flow path for a period of time sufficient to permit the flowing sample solvent liquid to pass the loaded individual sample from said sizing container to and through said chromatography column;
a source of rinse solvent liquid;
rinse means operative when said sizing container is inserted into said sample solvent flow path for flowing said rinse solvent liquid through said common flow path and through the storage container from which the current sample in the sizing container was loaded; and
collection means for storing at least one of said qualitative components from each of said individual samples passes through said column.

12. The chromatography system according to claim 11 wherein said loading means comprises:
a source of pressurized purge gas; and
means for selectively pressurizing each of said storage containers in sequence with said purge gas to force the sample fluid from each container through said common flow path and into said common sizing loop.

13. The chromatography system according to claim 11 wherein said loading means further comprises:
a multiple port valve having at least first and second commonly actuated valve sections, said first and second valve sections each including a common port and multiple individually accessible ports equal in number to at least a plurality of said multiple storage containers, wherein flow communication is provided between the common port and only the currently accessed port;
multiple pick-up tubes, each connected from a respective storage container to a respective accessible port in the first valve section to deliver sample fluid to the common port of said first valve section when said respective storage container is pressurized;
multiple delivery tubes, each connected from a respective storage container to a respective accessible port of the second valve section, for delivering pressurized fluid from the common port of said second valve section to pressurize said respective storage section; and
selectively actuable selection means for selectively providing flow communication between the common port of said first valve section and said common sizing container.

14. The chromatography system according to claim 13 wherein said rinse means comprises selectively actuable rinse control means for selectively delivering rinse solvent fluid under pressure to the common port of said second valve section.

15. The chromatography system according to claim 14 further comprising:
flow regulator means for supplying said purge gas at a known pressure and flow rate;
a rinse solvent container for temporarily storing a predetermined volume of said rinse solvent; and
individually actuable vent, purge and rinse valves, each having a common port, a normally open port in flow communication with said common port only when the valve is not actuated, and a normally closed port in flow communication with said common port only when the valve is actuated;
wherein said purge control means includes: conduit means connecting purge gas from said flow regulator means to the normally closed port of said purge valve; conduit means connecting the common port of said purge valve to the normally open port of said rinse valve; and conduit means connecting the common port of said rinse valve to the common port of said first section of said multiple port valves;
wherein said rinse control means comprises: conduit means connecting said purge gas from said flow regulator to the normally closed port of said vent valve; conduit means connecting the common port of said vent valve to the rinse solvent container to permit purge gas passing through the vent valve common port to pressurize the rinse solvent container; and rinse solvent flow means for delivering rinse solvent from said rinse solvent container, when pressurized, to the normally closed port of said rinse valve;

wherein said loading means further includes means for selectively actuating said purge valve while maintaining said vent and rinse valves unactuated; and means for selectively actuating said vent and rinse valves while maintaining said purge valve unactuated.

16. The chromatography system according to claim 11 further comprising:

a system housing;

multiple support arms each having a proximal end secured to said housing and a distal end remote from said housing, said distal end having a top side and an underside;

attachment means for suspending each sample storage container from the distal end of a respective support arm, said attachment means comprising:

a closure member having top and bottom surfaces and an axially-extending closure bore defined therein between said top and bottom surfaces, wherein said closure bore includes a top section diametrically enlarged relative to a bottom section to thereby define an upwardly-facing annular shoulder at the juncture between the top and bottom sections, and wherein said bottom section is sized to receive and engage an upper end of a respective sample storage container;

a closure insert having an axial length substantially equal to the axial length of the top section of said closure bore and radially dimensioned to correspond to the top section of the closure bore so that the closure insert fits snugly in the top section of the closure bore with the top of said closure insert substantially flush with the top surface of said closure member;

wherein said closure insert has an axial insert bore defined therethrough in coaxial alignment wit the closure bore, said insert bore having two axial portions, namely an upper threaded portion of relatively small diameter and a lower portion of relatively large diameter, the upper and lower portions joining one another at a downwardly-facing annular shoulder;

an O-ring disposed in the lower portion of said insert bore and container between said upwardly-facing shoulder and said downwardly-facing shoulder;

wherein each support arm has an access hole defined through from said top side to said underside;

means securing said closure member to said respective support arm with the top surface of the closure member flush against said underside and with said access hole aligned with said insert and closure bores to permit conduction of fluid between said each sample storage container and a location above the top side of said respective support arm;

connector means disposed proximate the top side of said respective support arm and having a hollow body, a bottom male fitting extending through said access hole and threaded to engage the upper threaded bore section of said closure insert, and first and second top fittings;

a first tube extending through said top fitting, the hollow connector body, the bottom male fitting and the aligned insert and closure bores to approximately the bottom of said sample storage container; and fluid conduit means secured to said second top fitting in flow communication with the upper end of said sample storage container via the follow connector body and an annular flow path disposed about said first tube through said bottom fitting and said insert and closure bores;

wherein said first tube corresponds to a pick-up tube, and said fluid conduit means corresponds to a delivery tube.

17. The chromatography system according to claim 11 wherein said valve means comprises:

a sample inject valve having six ports A, B, C, D, E and F, and selectively actuable between first and second positions;

wherein at said first position flow communication is provided between ports A and B, between ports C and D, and between ports E and F;

wherein for said second position fluid communication is provided between ports A and F, between ports B and C and between ports D and E;

wherein said common sizing container is a length of tubing having a first end connected to port C and a second end connected to port F;

wherein said loading means includes a conduit connected with substantially no slack between port D and the common port of the first section of said multiple port valve;

wherein said one qualitative component may be analyzed as a solute in said sample solvent;

conduit means providing flow communication between port A and one end of said chromatography column;

means for venting port E; and control means for automatically actuating the sample object valve to its first position in order to load an individual sample into said common sizing container, and to its second position to pass the individual sample located in the common sizing container through said column.

18. The chromatography system according to claim 17 further comprising:

a selectively actuable dump/collect valve having a normally closed port, a vented normally open Port and a common port in fluid communication with the normally open port when the dump/collect valve is unactuated, and in flow communication with said normally closed port when said dump/collect valve is actuated;

conduit means providing fluid communication between the second end of said chromatography column and the common port of said dump/collect valve;

multiple sample collection containers, one for each of said sample storage containers;

a third valve section of said multiple port valve actuable with said first and second sections of said multiple port valve and including: a common port connected in fluid communication with the normally closed port of said dump/collect valve; and plural individually-accessible ports each connected in flow communication with a respective sample collection container; and means for selectively actuating said dump/collect valve at a selected time after actuation of said sample inject valve to permit collection in a respective sample collection container of only sample fluid egressing from said chromatography column after said selected time.

19. A method for processing multiple samples of fluid in order to chromatography separate components within individual samples, said method comprising the steps of:

storing, in multiple respective storage containers, an amount in excess of a predetermined volume of multiple respective samples to be chromatographically treated in a column to obtain qualitative components for analysis;

automatically loading and filling a common sample sizing container with said individual samples in a selected sequence and via a common flow path, said common sample sizing container having a capacity of said predetermined volume;

substantially continuously flowing a sample solvent fluid from a sample solvent container to said column via a sample solvent flow path;

temporarily inserting said sizing container into said sample solvent flow path for a period of time sufficient to permit the flowing sample solvent liquid to pass the individual sample from said sizing container to and through said column;

during insertion of said sizing container into said sample solvent flow path, flowing rinse solvent liquid from a source thereof through said common flow path and through the storage container from which the sample currently in the sizing container was loaded; and storing at least one of said qualitative components from each of said individual samples passed through said column.

20. The method according to claim 19 wherein the step of automatically loading comprises selectively pressurizing each of said storage containers with a pressurized purge gas to force the sample fluid from said each container through said common flow path and into said common sizing loop.

21. The method according to claim 20 wherein said step of automatically loading includes delivering pressurized fluid from a common port of a second of two commonly actuable valve sections to pressurize said storage containers in a prescribed sequence;

delivering sample fluid to the common port of a first of said valve sections from the pressurized storage container via a respective one of multiple pick-up tubes;

selectively delivering pressurized purge gas to the common port of said second valve section; and selectively providing flow communication between the common port of said first valve section and said common sizing container.

* * * * *